United States Patent
Tanikawa et al.

(10) Patent No.: US 6,486,178 B1
(45) Date of Patent: Nov. 26, 2002

(54) INDANE DERIVATIVES

(75) Inventors: Keizo Tanikawa, Funabashi (JP); Kazuhiko Ohrai, Funabashi (JP); Masayuki Sato, Funabashi (JP); Kazufumi Yanagihara, Funabashi (JP); Yukihiro Shigeta, Funabashi (JP); Toru Yamashita, Minamisaitama-gun (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 09/701,281
(22) PCT Filed: Jun. 2, 1999
(86) PCT No.: PCT/JP99/02935
§ 371 (c)(1), (2), (4) Date: Nov. 28, 2000
(87) PCT Pub. No.: WO99/62867
PCT Pub. Date: Dec. 9, 1999

(30) Foreign Application Priority Data

Jun. 3, 1998 (JP) .............................. 10-154325
Apr. 15, 1999 (JP) .............................. 11-107647

(51) Int. Cl.$^7$ .................. A61K 31/4418; C07D 211/26
(52) U.S. Cl. ................. 514/319; 514/219; 514/428; 514/475; 514/539; 514/617; 514/622; 546/205; 548/568; 549/545; 558/414; 560/8; 564/342
(58) Field of Search ................ 514/617, 475, 514/539, 622, 319, 428; 564/342; 549/545; 560/8; 546/205; 548/568; 558/414

(56) References Cited

U.S. PATENT DOCUMENTS

| | | | |
|---|---|---|---|
| 4,788,130 A | * | 11/1988 | Oshiro et al. |
| 5,097,037 A | | 3/1992 | Matsumoto et al. |
| 5,420,314 A | | 5/1995 | Katsuki et al. |

FOREIGN PATENT DOCUMENTS

| | | |
|---|---|---|
| EP | 0 409 165 A2 | 1/1991 |
| EP | 0 535 377 A2 | 4/1993 |
| JP | 56-57785 | 5/1981 |
| JP | 56-57786 | 5/1981 |
| JP | 58-67683 | 4/1983 |
| JP | 58-188880 | 11/1983 |
| JP | 58-201776 | 11/1983 |
| JP | 63-26445 | 2/1988 |
| JP | 2-141 | 1/1990 |
| JP | 3-141286 | 6/1991 |
| JP | 5-301878 | 11/1993 |
| JP | 7-285983 | 10/1995 |
| WO | WO 91/14694 | 10/1991 |

OTHER PUBLICATIONS

Buckle, D.R. et al., J. Med. Chem. Soc., 34, 919–926, 1991.

* cited by examiner

Primary Examiner—T. A. Solola
Assistant Examiner—Sonya Wright
(74) Attorney, Agent, or Firm—Oliff & Berridge, PLC

(57) ABSTRACT

The present invention provides medicines for treating cardiac insufficiency which contain as an active ingredient indane derivatives of formula (I)

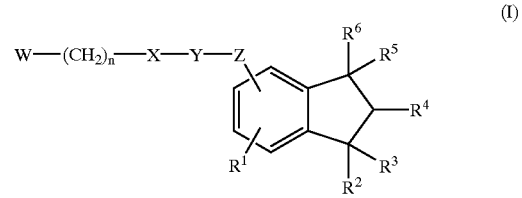

wherein $R^1$ represents hydrogen atom, nitro group, cyano group, $C_{1-6}$ alkylcarbonylamino, $R^2$ and $R^3$ each independently represent $C_{1-6}$ alkyl group, $R^4$ represents hydroxyl group or $C_{1-6}$ alkylcarbonyloxy group or represents a bond or oxygen atom together with $R^5$, $R^5$ represents hydrogen atom or represents a bond or oxygen atom together with $R^4$, $R^6$ represents hydrogen atom, hydroxyl group or $NR^7R^8$, n means 0 or an integer of 1 to 4, X represents C=O, $CH_2$, $SO_2$ or $NR^{16}$, Y represents $NR^{17}$ when X is C=O, $CH_2$ or $SO_2$ and represents C=O when X is $NR^{16}$, Z is absent when Y represents $NR^{17}$ or represents $NR^{18}$ when Y is C=O, W represents aromatic groups or lactam rings, or pharmaceutically acceptable salt thereof.

12 Claims, No Drawings

INDANE DERIVATIVES

This application is a 371 of PCT/JP99/02935 filed Jun. 2, 1999.

TECHNICAL FIELD

The present invention relates to an indane derivative having bradycardia activity and is used for treating cardiac insufficiency in mammals inclusive of human being.

BACKGROUND OF THE TECHNOLOGY

Japanese Patent Application Laid-open No. Sho 63-264445 discloses that an indane derivative have strong affinity to an opiate-acceptor, especially κ-acceptor and have neutral sadation property. Japanese Patent Application Laid-open No. Hei 2-141 discloses a certain kind of indane derivative which has an activity of loosing smooth muscle. However, the both publications do not refer to the possibility of treating the cardiac insufficiency on the basis of bradycardia activity.

The cardiac insufficiency which is in a state of insufficient function of heart is a disease which is based on the depression of contraction of heart muscles. As a treatment therefor, it has been clinically used medicines for reinforcing the contraction of cardiac muscles. However, these medicines have such a problem that heart muscles energy is excessively consumed on the basis of the increase of the heart rate and thus, they have had problems to be solved with respect to effects to improve life recuperation after administration of these medicines in a long period of time. It has been, therefore, desired to develop medicines which reduce load in consumption of heart muscle energy by reducing heart rate (i.e., bradycardia activity).

DISCLOSURE OF THE INVENTION

As a result that the present inventors have intensively studied indane derivatives, they found out that the compounds of the following formula (I) have strong bradycardia activity and they are useful as a medicine for treating insufficient cardiac disorders, whereby completing the present invention.

The present invention relates to indane derivatives of formula (I):

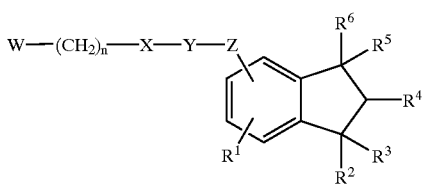

(I)

(wherein $R^1$ represents hydrogen atom, halogen atom, $C_{1-6}$ alkyl group (said alkyl group is unsubstituted or substituted by halogen atom, carboxyl group, $C_{1-6}$ alkoxy group, $C_{2-6}$ alkoxycarbonyl group, hydroxyl group, formyl group, cyano group or nitro group), $C_{1-6}$ alkoxy group {said alkoxy group is unsubstituted or substituted by halogen atom, carboxyl group, $C_{2-6}$ alkoxycarbonyl group, hydroxyl group, formyl group, phenyl group (said phenyl group is unsubstituted or substituted by halogen atom, hydroxyl group, $C_{1-4}$ alkyl group or $C_{1-4}$ alkoxy group), formyl group, cyano group or nitro group}, $C_{3-6}$ cycloalkyl group {said cycloalkyl group is unsubstituted or substituted by halogen atom, carboxyl group, $C_{2-6}$ alkoxycarbonyl group, hydroxyl group, $C_{1-6}$ alkoxy group, phenyl group (said phenyl group is unsubstituted or substituted by halogen atom, hydroxyl group, $C_{1-4}$ alkyl group or $C_{1-4}$ alkoxy group), formyl group, cyano group or nitro group}, nitro group, cyano group, formyl group, carboxyl group, hydroxyl group, formamide group, cyanamide group, amino group, $C_{1-6}$ alkylamino group, di $C_{1-6}$ alkylamino group (said alkylamino group and di $C_{1-6}$ alkylamino group is unsubstituted or substituted by halogen atom, carboxyl group, $C_{2-6}$ alkoxycarbonyl group, hydroxyl group, formyl group, cyano group or nitro group), $C_{1-6}$ alkylcarbonylamino group, $C_{1-6}$ alkylsulfonylamino group, aminocarbonyl group, $C_{1-6}$ alkylaminocarbonyl group, di $C_{1-6}$ alkylaminocarbonyl group, $C_{1-6}$ alkylcarbony group, $C_{1-6}$ alkoxycarbonyl group, $C_{1-6}$ alkylcarbonyloxy group, $C_{1-6}$ alkylurea group, $C_{1-6}$ alkylthiourea group, aryl $C_{1-6}$ alkylamino group, di(aryl $C_{1-6}$ alkyl)amino group, arylcarbonylamino group, aryl $C_{1-6}$ alkylcarbonylamino group, arylsulfonylamino group, aryl $C_{1-6}$ alkylsulfonylamino group, aryl $C_{1-6}$ alkylaminocarbonyl group, di(aryl $C_{1-6}$ alkyl)aminocarbonyl group, arylcarbonyl group, aryl $C_{1-6}$ alkylcarbonyl group, aryloxycarbonyl group, aryl $C_{1-6}$ alkyloxycarbonyl group, arylcarbonyloxy group, aryl $C_{1-6}$ alkylcarbonyloxy group, arylurea group, aryl $C_{1-6}$ alkylurea group, arylthiourea group or aryl $C_{1-6}$ alkylthiourea group {all of said aryl $C_{1-6}$ alkylamino group, di(aryl $C_{1-6}$ alkyl) amino group, arylcarbonylamino group, aryl $C_{1-6}$ alkylcarbonylamino group, arylsulfonylamino group, aryl $C_{1-6}$ alkylsulfonylamino group, aryl $C_{1-6}$ alkylaminocarbonyl group, di(aryl $C_{1-6}$ alkyl)aminocarbonyl group, arylcarbonyl group, aryl $C_{1-6}$ alkylcarbonyl group, aryloxycarbonyl group, aryl $C_{1-6}$ alkyloxycarbonyl group, arylcarbonyloxy group, aryl $C_{1-6}$ alkylcarbonyloxy group, arylurea group, aryl $C_{1-6}$ alkylurea group, arylthiourea group and aryl $C_{1-6}$ alkylthiourea group are unsubstituted or substituted by halogen atom, carboxyl group, $C_{2-6}$ alkoxycarbonyl group, hydroxyl group, $C_{1-6}$ alkoxy group, phenyl group (said phenyl group is unsubstituted or substituted by halogen atom, hydroxyl group, $C_{1-4}$ alkyl group or $C_{1-4}$ alkoxy group), formyl group, cyano group or nitro group};

$R^2$ and $R^3$ each independently represent $C_{1-6}$ alkyl group (said alkyl group is unsubstituted or substituted by halogen atom, $C_{1-6}$ alkoxy group or hydroxyl group), or $R^2$ and $R^3$ taken together with the carbon atom to which they are bonded form $C_{3-6}$ cycloalkyl group;

$R^4$ represents hydroxyl group or $C_{1-6}$ alkylcarbonyloxy group, or form a bond together with $R^5$, or represents oxygen atom together with $R^5$;

$R^5$ represents hydrogen atom, or forms a bond together with $R^4$, or represents oxygen atom together with $R^4$;

$R^6$ represents hydrogen atom, hydroxyl group, $C_{1-6}$ alkoxy group, $C_{1-6}$ alkylcarbonyloxy group or $NR^7R^8$ {said $R^7$ and $R^8$ each independently represent hydrogen atom, $C_{1-6}$ alkyl group, $C_{2-6}$ alkenyl group, $C_{2-6}$ alkynyl group, $C_{3-6}$ cycloalkyl group (all of said alkyl group, alkenyl group, alkynyl group and cycloalkyl group are unsubstituted or substituted by halogen atom, carboxyl group, $C_{2-6}$ alkoxycarbonyl group, hydroxyl group, $C_{1-6}$ alkoxy group, phenyl group (said phenyl group is unsubstituted or substituted by halogen atom, hydroxyl group, $C_{1-4}$ alkyl group, $C_{1-4}$ alkoxy group, formyl group, cyano group, nitro group, amino group, $C_{1-6}$ alkylamino group or di $C_{1-6}$ alkylamino group)) or phenyl group (said phenyl group is unsubstituted or substituted by halogen atom, hydroxyl group, $C_{1-4}$ alkyl group or $C_{1-4}$ alkoxy group), or $R^7$ and $R^8$ taken together represents 1,4-butylene, 1,5-pentylene (said butylene and pentylene are each unsubstituted or substituted by C$_{1-4}$ alkyl group, phenyl group (said phenyl group is unsubstituted or substituted by halogen atom, hydroxyl group, C$_{1-4}$ alkyl group or C$_{1-4}$ alkoxy group), halogen atom, hydroxyl group, C$_{1-4}$ alkoxy group or C$_{1-6}$ alkylcarbonyloxy group) or (CH$_2$)$_1$X$^1$(CH$_2$)$_p$ (1 and p mean each 1, 2 or 3 while the sum of them becomes 3, 4 or 5; X$^1$ represents oxygen atom, sulfur atom or NR$^{14}$ (R$^{14}$ is unsubstituted or substituted by hydrogen atom, C$_{1-4}$ alkyl group or phenyl group (said phenyl group is unsubstituted or substituted by halogen atom, hydroxyl group, C$_{1-4}$ alkyl group or C$_{1-4}$ alkoxy group)), or R$^7$ and R$^8$ taken together with nitrogen atom to which they are bonded form pyrrolyl group, pyrazolyl group, imidazolyl group, 1,2,3-triazolyl group, 1,2,4-triazolyl group or 1,2,3,4-tetrazolyl group which is unsubstituted or substituted by R$^{15}$ (R$^{15}$ has the same meanings as defined in R$^{10}$};

n means 0 or an integer of 1 to 4;

X represents C=O, CH$_2$, SO$_2$ or NR$^{16}$ (R$^{16}$ has the same meanings as defined in R$^{14}$);

Y represents NR$^{17}$ (R$^{17}$ has the same meanings as defined in R$^{14}$) when X is C=O, CH$_2$ or SO$_2$ and represents C=O when X is NR$^{16}$;

Z is absent when Y represents NR$^{17}$ or represents NR$^{18}$ (R$^{18}$ has the same meanings as defined in R$^{14}$) when Y is C=O;

W represents

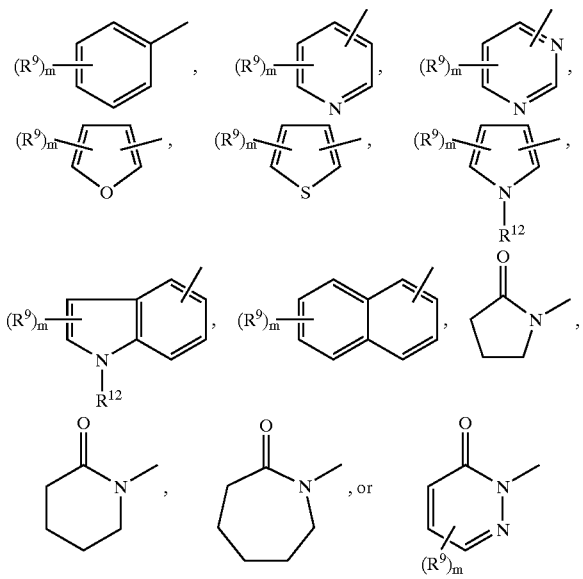

{wherein R$^9$ represents hydrogen atom, halogen atom, C$_{1-6}$ alkyl group (said alkyl group is unsubstituted or substituted by halogen atom or C$_{1-6}$ alkoxy group), C$_{1-6}$ alkoxy group (said alkoxy group is unsubstituted or substituted by halogen atom), phenyl group (said phenyl group is unsubstituted or substituted by halogen atom, hydroxyl group, C$_{1-4}$ alkyl group or C$_{1-4}$ alkoxy group), hydroxyl group, nitro group, cyano group, formyl group, formamide group, amino group, C$_{1-6}$ alkylamino group, di C$_{1-6}$ alkylamino group, C$_{1-6}$ alkylcarbonylamino group, C$_{1-6}$ alkylsulfonylamino group, aminocarbonyl group, C$_{1-6}$ alkylaminocarbonyl group, di C$_{1-6}$ alkylaminocarbonyl group, C$_{1-6}$ alkylcarbony group, C$_{1-6}$ alkoxycarbonyl group, aminosulfonyl group, C$_{1-6}$ alkylsulfonyl group, carboxyl group or arylcarbonyl group;

m is an integer of 1 to 3; and R$^9$ may be the same or different when m is 2 or 3;

R$^{12}$ represents hydrogen atom or C$_{1-4}$ alkyl group}], or pharmaceutically acceptable salt thereof.

The compounds of the present invention have strong activity of reducing the heart rate and are useful for improving cardiac functions and therefore, they are usable as medicines for treating cardiac insufficiency.

The substituents in the compounds of the formula (I) will be explained in more detail hereunder.

In this specification, "n" means normal, "i" does iso, "s" does secondary, "t" does tertiary, "c" does cyclo, "o" does ortho, "m" does meta, and "p" does para.

The halogen atom includes, for example, fluorine atom, chlorine atom, bromine atom and iodine atom. Of these halogen atoms, fluorine atom, chlorine atom and bromine atom are preferable.

The C$_{1-6}$ alkyl group includes, for example, methyl, ethyl, n-propyl, i-propyl, n-butyl, i-butyl, s-butyl, t-butyl, 1-pentyl, 2-pentyl, 3-pentyl, i-pentyl, neopentyl, 2,2-dimethylpropyl, 1-hexyl, 2-hexyl, 3-hexyl, 1-methyl-n-pentyl, 1,1,2-trimethyl-n-propyl, 1,2,2-trimethyl-n-propyl, 3,3-dimethyl-n-butyl, trifluoromethyl, trifluoroethyl, pentafluoroethyl, cyanomethyl and hydroxymethyl. Of these C$_{1-6}$ alkyl groups, methy, ethyl, n-propyl, i-propyl and n-butyl are preferable.

The C$_{1-6}$ alkoxy group includes, for example, methoxy, trifluoromethoxy, ethoxy, n-propoxy, i-propoxy, n-butoxy, i-butoxy, s-butoxy, t-butoxy, 1-pentyloxy, 2-pentyloxy, 3-pentyloxy, i-pentyloxy, neopentyloxy, 2,2-dimethylpropoxy, 1-hexyloxy, 2-hexyloxy, 3-hexyloxy, 1-methyl-n-pentyloxy, 1,1,2-trimethyl-n-propoxy, 1,2,2-trimethyl-n-propoxy and 3,3-dimethyl-n-butoxy. Of these C$_{1-6}$ alkoxy groups, methoxy, ethoxy, n-propoxy and i-propoxy are preferable.

The aryl group includes, for example, phenyl, biphenyl, naphthyl, anthryl and phenanthryl. Of these aryl groups, phenyl, biphenyl and naphthyl are preferable.

The C$_{3-6}$ cycloalkyl group includes, for example, cyclopropyl, cyclobutyl, cyclopentyl, cyclohexyl, cycloheptyl and cyclooctyl. Of these C$_{3-6}$ cycloalkyl groups, cyclopropyl, cyclobutyl and cyclohexyl are preferable.

The C$_{1-6}$ alkylamino group includes, for example, methylamino, ethylamino, n-propylamino, i-propylamino, c-propylamino, n-butylamino, i-butylamino, s-butylamino, t-butylamino, c-butylamino, 1-pentylamino, 2-pentylamino, 3-pentylamino, i-pentylamino, neopentylamino, t-pentylamino, c-pentylamino, 1-hexylamino, 2-hexylamino, 3-hexylamino, c-hexylamino, 1-methyl-n-pentylamino, 1,1,2-trimethyl-n-propylamino, 1,2,2-trimethyl-n-propylamino and 3,3-dimethyl-n-butylamino. Of these C$_{1-6}$ alkylamino groups, methylamino, ethylamino, n-propylamino, i-propylamino and n-butylamino are preferable.

The di C$_{1-6}$ alkylamino group includes, for example, dimethylamino, diethylamino, di-n-propylamino, di-i-propylamino, di-c-propylamino, di-n-butylamino, di-i-butylamino, di-s-butylamino, di-t-butylamino, di-c-butylamino, di-1-pentylamino, di-2-pentylamino, di-3-pentylamino, di-i-pentylamino, di-neopentylamino, di-t-pentylamino, di-c-pentylamino, di-1-hexylamino, di-2-hexylamino, di-3-hexylamino, di-c-hexylamino, di-(1-methyl-n-pentyl)amino, di-(1,1,2-trimethyl-n-propyl)amino, di-(1,2,2-trimethyl-n-propyl)amino, di-(3,3- dimethyl-n-butyl)amino, methyl(ethyl)amino, methyl(n-propyl)amino, methyl(i-propyl)amino, methyl(c-propyl)amino, methyl(n-butyl)amino, methyl(i-butyl)amino, methyl(s-butyl)amino, methyl(t-butyl)amino, methyl(c-butyl)amino, ethyl(n-propyl)amino, ethyl(i-propyl)amino, ethyl(c-propyl)amino, ethyl(n-butyl)amino, ethyl(i-butyl)amino, ethyl(s-butyl)amino, ethyl(t-butyl)amino, ethyl(c-butyl)amino, n-propyl(i-propyl)amino, n-propyl(c-propyl)amino, n-propyl(n-butyl)amino, n-propyl(i-butyl)amino, n-propyl(s-butyl)amino, n-propyl(t-butyl)amino, n-propyl(c-butyl)amino, i-propyl(c-propyl)amino, i-propyl(n-butyl)amino, i-propyl(i-butyl)amino, i-propyl(s-butyl)amino, i-propyl(t-butyl)amino, i-propyl(c-butyl)amino, c-propyl(n-butyl)amino, c-propyl(i-butyl)amino, c-propyl(s-butyl)amino, c-propyl(t-butyl)amino, c-propyl(c-butyl)amino, n-butyl(i-butyl)amino, n-butyl(s-butyl)amino, n-butyl(t-butyl)amino, n-butyl(c-butyl)amino, i-butyl(s-butyl)amino, i-butyl(t-butyl)amino, i-butyl(c-butyl)amino, s-butyl(t-butyl)amino, s-butyl(c-butyl)amino and t-butyl(c-butyl)amino. Of these di $C_{1-6}$ alkylamino groups, dimethylamino, diethylamino, di-n-propylamino, di-i-propylamino and di-n-butylamino are preferable.

The aryl $C_{1-6}$ alkylamino group includes, for example, benzylamino, o-methylbenzylamino, m-methylbenzylamino, p-methylbenzylamino, o-chlorobenzylamino, m-chlorobenzylamino, p-chlorobenzylamino, o-fluorobenzylamino, p-fluorobenzylamino, o-methoxybenzylamino, p-methoxybenzylamino, p-nitrobenzylamino, p-cyanobenzylamino, phenethylamino, o-methylphenethylamino, m-methylphenethylamino, p-methylphenethylamino, o-chlorophenethylamino, m-chlorophenethylamino, p-chlorophenethylamino, o-fluorophenethylamino, p-fluorophenethylamino, o-methoxyphenethylamino, p-methoxyphenethylamino, p-nitrophenethylamino, p-cyanophenethylamino, phenylpropylamino, phenylbutylamino, phenylpentylamino, phenylhexylamino, naphthylamino, biphenylamino, anthrylamino and phenanthrylamino. Of these aryl $C_{1-6}$ alkylamino groups, benzylamino, p-methylbenzylamino, phenethylamino-p-methoxyphenethylamino and phenylpropylamino are preferable.

The $C_{1-6}$ alkylcarbonylamino group includes, for example, methylcarbonylamino, ethylcarbonylamino, n-propylcarbonylamino, i-propylcarbonylamino, n-butylcarbonylamino, i-butylcarbonylamino, s-butylcarbonylamino, t-butylcarbonylamino, 1-pentylcarbonylamino, 2-pentylcarbonylamino, 3-pentylcarbonylamino, i-pentylcarbonylamino, neopentylcarbonylamino, t-pentylcarbonylamino, 1-hexylcarbonylamino, 2-hexylcarbonylamino and 3-hexylcarbonylamino. Of these $C_{1-6}$ alkylcarbonylamino groups, methylcarbonylamino, ethylcarbonylamino, n-propylcarbonylamino, i-propylcarbonylamino and n-butylcarbonylamino are preferable.

The arylcarbonylamino group includes, for example, benzoylamino, 1-naphthylcarbonylamino, 2-naphthylcarbonylamino, o-methylbenzoylamino, m-methylbenzoylamino, p-methylbenzoylamino, o-chlorobenzoylamino, p-chlorobenzoylamino, o-fluorobenzoylamino, p-fluorobenzoylamino, o-methoxybenzoylamino, p-methoxybenzoylamino, p-nitrobenzoylamino, p-cyanobenzoylamino and p-phenylbenzoylamino. Of these arylcarbonylamino groups, benzoylamino and p-fluorobenzoylamino are preferable.

The aryl $C_{1-6}$ alkylcarbonylamino group includes, for example, phenylacetylamino, o-methylphenylacetylamino, m-methylphenylacetylamino, p-methylphenylacetylamino, o-chlorophenylacetylamino, p-chlorophenylacetylamino, p-fluorophenylacetylamino, o-methoxyphenylacetylamino, p-methoxyphenylacetylamino, p-nitrophenylacetylamino, p-cyanophenylacetylamino, 2-phenylethylcarbonylamino, 3-phenylpropylcarbonylamino, 4-phenylbutylcarbonylamino, 5-phenylpentylcarbonylamino and 6-phenylhexylcarbonylamino. Of these aryl $C_{1-6}$ alkylcarbonylamino groups, phenylacetylamino and 2-phenylethylcarbonylamino are preferable.

The $C_{1-6}$ alkylsulfonylamino group includes, for example, methylsulfonylamino, ethylsulfonylamino, n-propylsulfonylamino, i-propylsulfonylamino, n-butylsulfonylamino, i-butylsulfonylamino, s-butylsulfonylamino, t-butylsulfonylamino, 1-pentylsulfonylamino, 2-pentylsulfonylamino, 3-pentylsulfonylamino, i-pentylsulfonylamino, neopentylsulfonylamino, t-pentylsulfonylamino, 1-hexylsulfonylamino, 2-hexylsulfonylamino and 3-hexylsulfonylamino. Of these $C_{1-6}$ alkylsulfonylamino groups, methylsulfonylamino, ethylsulfonylamino, n-propylsulfonylamino, i-propylsulfonylamino and n-butylsulfonylamino are preferable.

The arylsulfonylamino group includes, for example, benzenesulfonylamino and p-toluenesulfonylamino.

The $C_{1-6}$ alkylaminocarbonyl group includes, for example, methylaminocarbonyl, ethylaminocarbonyl, n-propylaminocarbonyl, i-propylaminocarbonyl, n-butoxylaminocarbonyl, i-butoxylaminocarbonyl, s-butoxylaminocarbonyl, t-butoxylaminocarbonyl, 1-pentylaminocarbonyl, 2-pentylaminocarbonyl, 3-pentylaminocarbonyl, i-pentylaminocarbonyl, neopentylaminocarbonyl, t-pentylaminocarbonyl, 1-hexylaminocarbonyl, 2-hexylaminocarbonyl and 3-hexylaminocarbonyl. Of these $C_{1-6}$ alkylaminocarbonyl groups, methylaminocarbonyl, ethylaminocarbonyl, n-propylaminocarbonyl, i-propylaminocarbonyl and n-butoxylaminocarbonyl are preferable.

The di $C_{1-6}$ alkylaminocarbonyl group includes, for example, dimethylaminocarbonyl, diethylaminocarbonyl, di-n-propylaminocarbonyl, di-i-propylaminocarbonyl, di-c-propylaminocarbonyl, di-n-butoxylaminocarbonyl, di-i-butoxylaminocarbonyl, di-s-butoxylaminocarbonyl, di-t-butoxylaminocarbonyl, di-c-butoxylaminocarbonyl, di-1-pentylaminocarbonyl, di-2-pentylaminocarbonyl, di-3-pentylaminocarbonyl, di-i-pentylaminocarbonyl, di-neopentylaminocarbonyl, di-t-pentylaminocarbonyl, di-c-pentylaminocarbonyl, di-1-hexylaminocarbonyl, di-2-hexylaminocarbonyl and di-3-hexylaminocarbonyl.

Of these di $C_{1-6}$ alkylaminocarbonyl groups, dimethylaminocarbonyl, diethylaminocarbonyl, di-n-propylaminocarbonyl, di-i-propylaminocarbonyl, di-c-propylaminocarbonyl and di-n-butoxylaminocarbonyl are preferable.

The aryl $C_{1-6}$ alkylaminocarbonyl group includes, for example, benzylaminocarbonyl, o-methylbenzylaminocarbonyl, m-methylbenzylaminocarbonyl, p-methylbenzylaminocarbonyl, o-chlorobenzylaminocarbonyl, p-chlorobenzylaminocarbonyl, o-fluorobenzylaminocarbonyl, p-fluorobenzylaminocarbonyl, o-methoxybenzylaminocarbonyl, p-methoxybenzylaminocarbonyl, p-nitrobenzylaminocarbonyl, p-cyanobenzylaminocarbonyl, p-fluorophenethylaminocarbonyl, phenethylaminocarbonyl, p-methylphenethylaminocarbonyl, p-chlorophenethylaminocarbonyl, p-cyanophenethylaminocarbonyl, phenethylaminocarbonyl, 3-phenylpropylaminocarbonyl, 4-phenylbutylaminocarbonyl, 5-phenylpentylaminocarbonyl and 6-phenylhexylaminocarbonyl.

Of these aryl $C_{1-6}$ alkylaminocarbonyl groups, benzylaminocarbony, p-methyl benzylaminocarbonyl, p-chlorobenzylaminocarbonyl, p-fluorobenzylaminocarbonyl and phenethylaminocarbonyl are preferable.

The $C_{1-6}$ alkylcarbonyl group includes, for example, methylcarbonyl, ethylcarbonyl, n-propylcarbonyl, i-propylcarbonyl, n-butylcarbonyl, i-butylcarbonyl, s-butylcarbonyl, t-butylcarbonyl, 1-pentylcarbonyl, 2-pentylcarbonyl, 3-pentylcarbonyl, i-pentylcarbonyl, neopentylcarbonyl, t-pentylcarbonyl, 1-hexylcarbonyl, 2-hexylcarbonyl and 3-hexylcarbonyl. Of these $C_{1-6}$ alkylcarbonyl groups, methylcarbonyl, ethylcarbonyl, n-propylcarbonyl, i-propylcarbonyl and n-butylcarbonyl are preferable.

The arylcarbonyl group includes, for example, benzoyl, p-methylbenzoyl, p-t-butylbenzoyl, p-methoxybenzoyl, p-chlorobenzoyl, p-nitrobenzoyl and p-cyanobenzoyl. Of these arylcarbonyl groups, benzoyl, p-nitrobenzoyl and p-cyanobenzoyl are preferable.

The aryl $C_{1-6}$ alkylcarbonyl group includes, for example, phenylacetyl, p-methylphenylacetyl, p-t-butylphenylacetyl, p-methoxyphenylacetyl, p-chlorophenylacetyl, p-nitrophenylacetyl, p-cyanophenylacetyl, phenethylcarbonyl, 3-phenylpropyl, 4-phenylbutyl, 5-phenylpentyl and 6-phenylhexyl. Of these aryl $C_{1-6}$ alkylcarbonyl groups, phenylacetyl and phenethylcarbonyl are preferable.

The $C_{1-6}$ alkoxycarbonyl group includes, for example, methoxycarbonyl, ethoxycarbonyl, n-propoxycarbonyl, i-propoxycarbonyl, n-butoxycarbonyl, i-butoxycarbonyl, s-butoxycarbonyl, t-butoxycarbonyl, 1-pentyloxycarbonyl, 2-pentyloxycarbonyl, 3-pentyloxycarbonyl, i-pentyloxycarbonyl, neopentyloxycarbonyl, t-pentyloxycarbonyl, 1-hexyloxycarbonyl, 2-hexyloxycarbonyl and 3-hexyloxycarbonyl. Of these $C_{1-6}$ alkoxycarbonyl groups, methoxycarbonyl, ethoxycarbonyl, n-propoxycarbonyl, i-propoxycarbonyl, n-butoxycarbonyl, i-butoxycarbonyl, s-butoxycarbonyl and t-butoxycarbonyl are preferable.

The aryloxycarbonyl group includes, for example, phenoxycarbonyl, o-methylphenoxycarbonyl, p-methylphenoxycarbonyl, p-chlorophenoxycarbonyl, p-fluorophenoxycarbonyl, p-methoxyphenoxycarbonyl, p-nitrophenoxycarbonyl, p-cyanophenoxycarbonyl, 1-naphthoxycarbonyl and 2-naphthoxycarbonyl.

The aryl $C_{1-6}$ alkyloxycarbonyl group includes, for example, benzyloxycarbonyl, o-methylbenzyloxycarbonyl, p-methylbenzyloxycarbonyl, p-chlorobenzyloxycarbonyl, p-fluorobenzyloxycarbonyl, p-methoxybenzyloxycarbonyl, p-nitrobenzyloxycarbonyl, p-cyanobenzyloxycarbonyl, 1-naphthoxymethylcarbonyl, 2-naphthoxymethylcarbonyl and pyridylmethyloxycarbonyl.

The $C_{1-6}$ alkylcarbonyloxy group includes, for example, methylcarbonyloxy, ethylcarbonyloxy, n-propylcarbonyloxy, i-propylcarbonyloxy, n-butylcarbonyloxy, i-butylcarbonyloxy, s-butylcarbonyloxy, t-butylcarbonyloxy, 1-pentylcarbonyloxy, 2-pentylcarbonyloxy, 3-pentylcarbonyloxy, i-pentylcarbonyloxy, neopentylcarbonyloxy, t-pentylcarbonyloxy, 1-hexylcarbonyloxy, 2-hexylcarbonyloxy, 3-hexylcarbonyloxy, 1-methyl-n-pentylcarbonyloxy, 1,1,2-trimethyl-n-propylcarbonyloxy, 1,2,2-trimethyl-n-propylcarbonyloxy and 3,3-dimethyl-n-butylcarbonyloxy.

Of these $C_{1-6}$ alkylcarbonyloxy groups, methylcarbonyloxy, ethylcarbonyloxy, n-propylcarbonyloxy, i-propylcarbonyloxy, n-butylcarbonyloxy and t-butylcarbonyloxy are preferable.

The arylcarbonyloxy group includes, for example, benzoyloxy, o-methylbenzoyloxy, p-methylbenzoyloxy, p-chlorobenzoyloxy, p-fluorobenzoyloxy, p-methoxybenzoyloxy, p-nitrobenzoyloxy, p-cyanobenzoyloxy, 1-naphthylcarbonyloxy and 2-naphthylcarbonyloxy.

The aryl $C_{1-6}$ alkylcarbonyloxy group includes, for example, benzylcarbonyloxy, o-methylbenzylcarbonyloxy, p-methylbenzylcarbonyloxy, p-chlorobenzylcarbonyloxy, p-fluorobenzylcarbonyloxy, p-methoxybenzylcarbonyloxy, p-nitrobenzylcarbonyloxy, p-cyanobenzylcarbonyloxy, 1-naphthoxymethylcarbonyloxy, 2-naphthoxymethylcarbonyloxy and pyridylmethyloxycarbonyloxy.

The $C_{1-6}$ alkylurea group includes, for example, methylurea, ethylurea, n-propylurea, i-propylurea, n-butylurea, i-butylurea, s-butylurea, t-butylurea, 1-pentylurea, 2-pentylurea, 3-pentylurea, i-pentylurea, neopentylurea, t-pentylurea, 1-hexylurea, 2-hexylurea, 3-hexylurea, 1-methyl-n-pentylurea, 1,1,2-trimethyl-n-propylurea, 1,2,2-trimethyl-n-propylurea and 3,3-dimethyl-n-butylurea.

The arylurea group includes, for example, phenylurea, o-methylphenylurea, p-methylphenylurea, p-chlorophenylurea, p-fluorophenylurea, p-methoxyphenylurea, p-nitrophenylurea, p-cyanophenylurea, 1-naphthylurea and 2-naphthylurea.

The aryl $C_{1-6}$ alkylurea group includes, for example, benzylurea, o-methylbenzylurea, p-methylbenzylurea, p-chlorobenzylurea, p-fluorobenzylurea, p-methoxybenzylurea, p-nitrobenzylurea, p-cyanobenzylurea, 1-naphthylmethylurea, 2-naphthylmethylurea and pyridylmethylurea.

The $C_{1-6}$ alkylthiourea group includes, for examples, methylthiourea, ethylthiourea, n-propylthiourea, i-propylthiourea, n-butylthiourea, i-butylthiourea, s-butylthiourea, t-butylthiourea, 1-pentylthiourea, 2-pentylthiourea, 3-pentylthiourea, i-pentylthiourea, neopentylthiourea, t-pentylthiourea, 1-hexylthiourea, 2-hexylthiourea, 3-hexylthiourea, 1-methyl-n-pentylthiourea, 1,1,2-trimethyl-n-propylthiourea, 1,2,2-trimethyl-n-propylthiourea and 3,3-dimethyl-n-butylthiourea.

The arylthiourea group includes, for example, phenylthiourea, o-methylphenylthiourea, p-methylphenylthiourea, p-chlorophenylthiourea, p-fluorophenylthiourea, p-methoxyphenylthiourea, p-nitrophenylthiourea, p-cyanophenylthiourea, 1-naphthylthiourea and 2-naphthylthiourea.

The aryl $C_{1-6}$ alkylthiourea group includes, for example, benzylthiourea, o-methylbenzylthiourea, p-methylbenzylthiourea, p-chlorobenzylthiourea, p-fluorobenzylthiourea, p-methoxybenzylthiourea, p-nitrobenzylthiourea, p-cyanobenzylthiourea, 1-naphthyltmethylthiourea, 2-naphthylmethylthiourea and pyridylmethylthiourea.

Preferable compounds usable for the present invention are as follows.

(1) Indane derivatives of the formula (I) wherein both $R^2$ and $R^3$ represent methyl group and the combination of —X—Y—Z— is —C(O)—NH—, —C(O)—NMe—, —CH$_2$—NH—, —SO$_2$—NH— or —NH—C(O)—NH—, or pharmaceutically acceptable salt thereof.

(2) Indane derivatives or pharmaceutically acceptable salt thereof as described in the above-item (1), wherein W represents

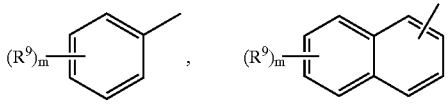

$R^9$ represents hydrogen atom, halogen atom, $C_{1-6}$ alkyl group, $C_{1-6}$ alkoxy group (said alkoxy group is unsubstituted or substituted by halogen atom), hydroxyl group, nitro group, cyano group, formyl group, amino group, $C_{1-6}$ alkylamino group, di $C_{1-6}$ alkylamino group, $C_{1-6}$ alkylcarbonylamino group, $C_{1-6}$ alkylsulfonylamino group, aminocarbonyl group, $C_{1-6}$ alkylaminocarbonyl group, di $C_{1-6}$ alkylaminocarbonyl group, $C_{1-6}$ alkylcarbonyl group, $C_{1-6}$ alkoxycarbonyl group, aminosulfonyl group, $C_{1-6}$ alkylsulfonyl group or carboxyl group.

(3) Indane derivatives or pharmaceutically acceptable salt thereof as described in the above-item (2), wherein $R^1$ represents hydrogen atom or nitro group.

(4) Indane derivatives or pharmaceutically acceptable salt thereof as described in the above-item (3), wherein $R^4$ forms a bond together with $R^5$; or $R^4$ represents oxygen atom together with $R^5$; or $R^4$ represents hydroxyl group, $R^5$ represents hydrogen atom and $R^6$ represents amino group, $C_{1-6}$ alkylamino group, di $C_{1-6}$ alkylamino group {said alkylamino group and di $C_{1-6}$ alkylamino group are unsubstituted or substituted by halogen atom, carboxyl group, $C_{2-6}$ alkoxycarbonyl group, hydroxyl group, formyl group, cyano group or nitro group}, $C_{1-6}$ cycloalkylamino group, aryl $C_{1-6}$ alkylamino group, di(aryl $C_{1-6}$ alkyl)amino group {both said aryl $C_{1-6}$ alkylamino group and di(aryl $C_{1-6}$ alkyl)amino group are unsubstituted or substituted by $R^{19}$ (said $R^{19}$ is unsubstituted or substituted by halogen atom, carboxyl group, $C_{2-6}$ alkoxycarbonyl group, hydroxyl group, $C_{1-6}$ alkoxy group, phenyl group (said phenyl group is unsubstituted or substituted by halogen atom, hydroxyl group, $C_{1-4}$ alkyl group or $C_{1-4}$ alkoxy group), formyl group, cyano group or nitro group)}, 1-pyrrolidinyl group, 1-imidazolidinyl group, 1-piperidyl group, 1-piperazinyl group or 1-morpholino group.

(5) Indane derivatives or pharmaceutically acceptable salt thereof as described in the above-item (4), wherein $R^9$ represents hydrogen atom, halogen atom, $C_{1-6}$ alkyl group, $C_{1-6}$ alkoxy group (said alkoxy group is unsubstituted or substituted by halogen atom), hydroxyl group, nitro group, cyano group, formyl group, amino group, $C_{1-6}$ alkylamino group, di $C_{1-6}$ alkylamino group, $C_{1-6}$ alkylcarbonyl group, $C_{1-6}$ alkoxycarbonyl group or carboxyl group.

(6) Indane derivatives or pharmaceutically acceptable salt thereof as described in the above-item (5), wherein $R^4$ forms a bond together with $R^5$.

(7) Indane derivatives or pharmaceutically acceptable salt thereof as described in the above-item (5), wherein $R^4$ represents hydroxyl group, $R^5$ represents hydrogen atom and $R^6$ represents amino group, $C_{1-6}$ alkylamino group, di $C_{1-6}$ alkylamino group {said alkylamino group and di $C_{1-6}$ alkylamino group are unsubstituted or substituted by halogen atom, carboxyl group, $C_{2-6}$ alkoxycarbonyl group, hydroxyl group, formyl group, cyano group or nitro group} or $C_{1-6}$ cycloalkylamino group.

(8) Indane derivatives or pharmaceutically acceptable salt thereof as described in the above-item (6), wherein W represents 4-methoxyphenyl group.

(9) Indane derivatives or pharmaceutically acceptable salt thereof as described in the above-item (7), wherein $R^6$ represents isopropylamino group or cyclopropylamino group, and W represents 4-methoxyphenyl group.

Concrete examples of compounds usable in the present invention are shown below. However, the present invention is not to be limited thereby. In the specification, "Me" means methyl group, "Et" does ethyl group, "Pr" does propyl group, "Bu" does butyl group, "Ac" does acetyl group (COCH$_3$) and "—" does a bond.

TABLE 1

Example of Compounds

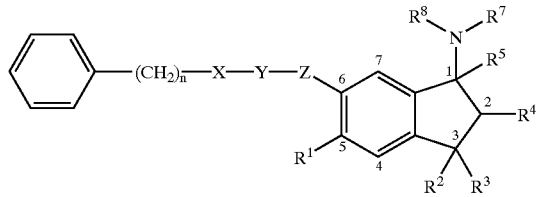

| $R^1$ | $R^2$ | $R^3$ | $R^4$ | $R^5$ | $R^7$ | $R^8$ | n | X | Y | Z |
|---|---|---|---|---|---|---|---|---|---|---|
| H | Me | Me | OH | H | —(CH$_2$)$_4$— | | 1 | CO | NH | — |
| F | Me | Me | OH | H | —(CH$_2$)$_4$— | | 1 | CO | NH | — |
| Br | n-Pr | n-Pr | OH | H | —(CH$_2$)$_4$— | | 1 | CO | NH | — |
| Me | Me | Me | OH | H | Et | H | 1 | CO | NH | — |
| CF$_3$ | Me | Et | OH | H | —(CH$_2$)$_4$— | | 2 | CO | NH | CH$_2$ |
| CH$_2$CF$_3$ | Et | Me | OH | H | —(CH$_2$)$_4$— | | 1 | CO | NH | — |
| C$_2$F$_5$ | Me | Me | — | | Me | H | 1 | CO | NH | — |
| OMe | Me | Me | OH | H | —(CH$_2$)$_4$— | | 2 | CO | NH | — |
| OCF$_3$ | Me | Me | OH | H | —(CH$_2$)$_4$— | | 1 | CO | NH | — |
| CH$_2$OMe | Me | Me | OH | H | —(CH$_2$)$_4$— | | 1 | CO | NH | — |
| c-Pr | Me | Me | OH | H | —(CH$_2$)$_4$— | | 3 | CO | NH | — |

TABLE 1-continued

Example of Compounds

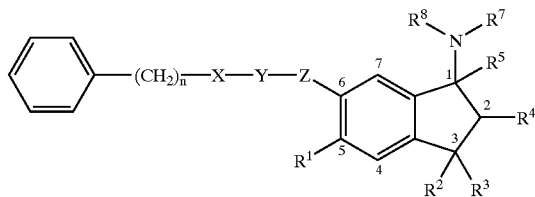

| R¹ | R² | R³ | R⁴ | R⁵ | R⁷ | R⁸ | n | X | Y | Z |
|---|---|---|---|---|---|---|---|---|---|---|
| NO₂ | Me | Me | OH | H | —(CH₂)₄— | | 1 | CO | NH | — |
| CN | Me | Me | OH | H | —(CH₂)₄— | | 1 | CO | NH | — |
| CHO | Me | Me | OH | H | —(CH₂)₄— | | 1 | CH₂ | NH | — |
| CO₂H | Me | Me | OH | H | —(CH₂)₄— | | 1 | CO | NH | — |
| OH | Me | Me | OH | H | —(CH₂)₄— | | 1 | CH₂ | NH | CH₂ |
| CH₂OH | Me | Me | — | | —(CH₂)₄— | | 1 | CO | NH | — |
| NHCHO | Me | Me | OH | H | —(CH₂)₄— | | 1 | NH | CO | NH |
| NHCN | Me | Me | OH | H | c-Pr | H | 1 | CO | NH | — |
| NH₂ | Me | Me | OAc | H | —(CH₂)₄— | | 1 | CO | NH | — |
| NHMe | Me | Me | OAc | H | —(CH₂)₄— | | 1 | CO | NH | — |
| NMe₂ | Me | Me | OAc | H | —(CH₂)₄— | | 1 | CO | NH | — |
| NHCOMe | Me | Me | OH | H | —(CH₂)₄— | | 1 | CO | NH | CH₂ |
| NHSO₂Me | Me | Me | OH | H | —(CH₂)₄— | | 1 | CO | NH | — |
| CONH₂ | Me | Me | OH | H | —(CH₂)₄— | | 4 | CO | NH | — |
| CONHMe | Me | Me | OH | H | —(CH₂)₄— | | 3 | CO | NH | — |
| CONMe₂ | Me | Me | OH | H | —(CH₂)₄— | | 2 | CO | NH | — |
| COMe | Me | Me | OH | H | Et | H | 1 | CO | NH | — |
| CO₂Me | Me | Me | OH | H | Me | H | 1 | CO | NH | — |
| CO₂Ph | Me | Me | OAc | H | i-Pr | H | 1 | CO | NH | — |
| CO₂CH₂Ph | Me | Me | OH | H | —(CH₂)₄— | | 1 | CO | NH | — |

TABLE 2

Example of Compounds

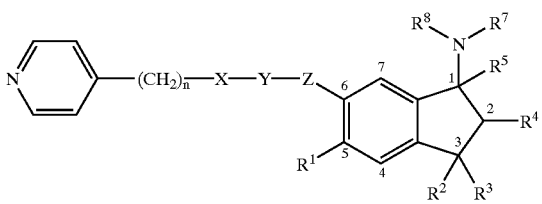

| R¹ | R² | R³ | R⁴ | R⁵ | R⁷ | R⁸ | n | X | Y | Z |
|---|---|---|---|---|---|---|---|---|---|---|
| H | Me | Me | OH | H | —(CH₂)₄— | | 1 | CO | NH | — |
| F | Me | Me | OH | H | —(CH₂)₄— | | 1 | CO | NH | — |
| Br | n-Pr | n-Pr | OH | H | —(CH₂)₄— | | 1 | CO | NH | — |
| Me | Me | Me | OH | H | Et | H | 1 | CO | NH | — |
| CF₃ | Me | Et | OH | H | —(CH₂)₄— | | 2 | CO | NH | CH₂ |
| CH₂CF₃ | Et | Me | OH | H | —(CH₂)₄— | | 1 | CO | NH | — |
| C₂F₅ | Me | Me | — | | Me | H | 1 | CO | NH | — |
| OMe | Me | Me | OH | H | —(CH₂)₄— | | 2 | CO | NH | — |
| OCF₃ | Me | Me | OH | H | —(CH₂)₄— | | 1 | CO | NH | — |
| CH₂OMe | Me | Me | OH | H | —(CH₂)₄— | | 1 | CO | NH | — |
| c-Pr | Me | Me | OH | H | —(CH₂)₄— | | 3 | CO | NH | — |
| NO₂ | Me | Me | OH | H | —(CH₂)₄— | | 1 | CO | NH | — |
| CN | Me | Me | OH | H | —(CH₂)₄— | | 1 | CO | NH | — |
| CHO | Me | Me | OH | H | —(CH₂)₄— | | 1 | CH₂ | NH | — |
| CO₂H | Me | Me | OH | H | —(CH₂)₄— | | 1 | CO | NH | — |
| OH | Me | Me | OH | H | —(CH₂)₄— | | 1 | CH₂ | NH | CH₂ |
| CH₂OH | Me | Me | — | | —(CH₂)₄— | | 1 | CO | NH | — |
| NHCHO | Me | Me | OH | H | —(CH₂)₄— | | 1 | NH | CO | NH |
| NHCN | Me | Me | OH | H | c-Pr | H | 1 | CO | NH | — |
| NH₂ | Me | Me | OAc | H | —(CH₂)₄— | | 1 | CO | NH | — |
| NHMe | Me | Me | OAc | H | —(CH₂)₄— | | 1 | CO | NH | — |
| NMe₂ | Me | Me | OAc | H | —(CH₂)₄— | | 1 | CO | NH | — |

TABLE 2-continued

Example of Compounds

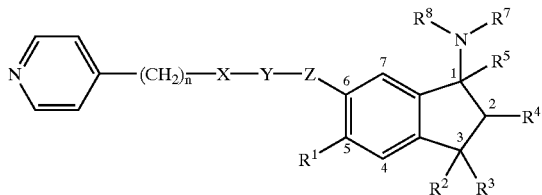

| R¹ | R² | R³ | R⁴ | R⁵ | R⁷ | R⁸ | n | X | Y | Z |
|---|---|---|---|---|---|---|---|---|---|---|
| NHCOMe | Me | Me | OH | H | —(CH₂)₄— | | 1 | CO | NH | CH₂ |
| NHSO₂Me | Me | Me | OH | H | —(CH₂)₄— | | 1 | CO | NH | — |
| CONH₂ | Me | Me | OH | H | —(CH₂)₄— | | 4 | CO | NH | — |
| CONHMe | Me | Me | OH | H | —(CH₂)₄— | | 3 | CO | NH | — |
| CONMe₂ | Me | Me | OH | H | —(CH₂)₄— | | 2 | CO | NH | — |
| COMe | Me | Me | OH | H | Et | H | 1 | CO | NH | — |
| CO₂Me | Me | Me | OH | H | Me | H | 1 | CO | NH | — |
| CO₂Ph | Me | Me | OAc | H | i-Pr | H | 1 | CO | NH | — |
| CO₂CH₂Ph | Me | Me | OH | H | —(CH₂)₄— | | 1 | CO | NH | — |

TABLE 3

Example of Compounds

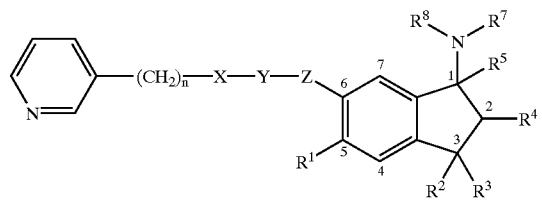

| R¹ | R² | R³ | R⁴ | R⁵ | R⁷ | R⁸ | n | X | Y | Z |
|---|---|---|---|---|---|---|---|---|---|---|
| H | Me | Me | OH | H | —(CH₂)₄— | | 1 | CO | NH | — |
| F | Me | Me | OH | H | —(CH₂)₄— | | 1 | CO | NH | — |
| Br | n-Pr | n-Pr | OH | H | —(CH₂)₄— | | 1 | CO | NH | — |
| Me | Me | Me | OH | H | Et | H | 1 | CO | NH | — |
| CF₃ | Me | Et | OH | H | —(CH₂)₄— | | 2 | CO | NH | CH₂ |
| CH₂CF₃ | Et | Me | OH | H | —(CH₂)₄— | | 1 | CO | NH | — |
| C₂F₅ | Me | Me | — | | Me | H | 1 | CO | NH | — |
| OMe | Me | Me | OH | H | —(CH₂)₄— | | 2 | CO | NH | — |
| OCF₃ | Me | Me | OH | H | —(CH₂)₄— | | 1 | CO | NH | — |
| CH₂OMe | Me | Me | OH | H | —(CH₂)₄— | | 1 | CO | NH | — |
| c-Pr | Me | Me | OH | H | —(CH₂)₄— | | 3 | CO | NH | — |
| NO₂ | Me | Me | OH | H | —(CH₂)₄— | | 1 | CO | NH | — |
| CN | Me | Me | OH | H | —(CH₂)₄— | | 1 | CO | NH | — |
| CHO | Me | Me | OH | H | —(CH₂)₄— | | 1 | CH₂ | NH | — |
| CO₂H | Me | Me | OH | H | —(CH₂)₄— | | 1 | CO | NH | — |
| OH | Me | Me | OH | H | —(CH₂)₄— | | 1 | CH₂ | NH | CH₂ |
| CH₂OH | Me | Me | — | | —(CH₂)₄— | | 1 | CO | NH | — |
| NHCHO | Me | Me | OH | H | —(CH₂)₄— | | 1 | NH | CO | NH |
| NHCN | Me | Me | OH | H | c-Pr | H | 1 | CO | NH | — |
| NH₂ | Me | Me | OAc | H | —(CH₂)₄— | | 1 | CO | NH | — |
| NHMe | Me | Me | OAc | H | —(CH₂)₄— | | 1 | CO | NH | — |
| NMe₂ | Me | Me | OAc | H | —(CH₂)₄— | | 1 | CO | NH | — |
| NHCOMe | Me | Me | OH | H | —(CH₂)₄— | | 1 | CO | NH | CH₂ |
| NHSO₂Me | Me | Me | OH | H | —(CH₂)₄— | | 1 | CO | NH | — |
| CONH₂ | Me | Me | OH | H | —(CH₂)₄— | | 4 | CO | NH | — |
| CONHMe | Me | Me | OH | H | —(CH₂)₄— | | 3 | CO | NH | — |
| CONMe₂ | Me | Me | OH | H | —(CH₂)₄— | | 2 | CO | NH | — |
| COMe | Me | Me | OH | H | Et | H | 1 | CO | NH | — |
| CO₂Me | Me | Me | OH | H | Me | H | 1 | CO | NH | — |
| CO₂Ph | Me | Me | OAc | H | i-Pr | H | 1 | CO | NH | — |
| CO₂CH₂Ph | Me | Me | OH | H | —(CH₂)₄— | | 1 | CO | NH | — |

TABLE 4

Example of Compounds

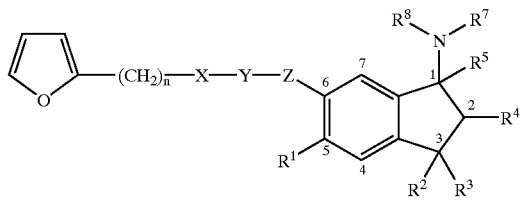

| R¹ | R² | R³ | R⁴ | R⁵ | R⁷ | R⁸ | n | X | Y | Z |
|---|---|---|---|---|---|---|---|---|---|---|
| H | Me | Me | OH | H | —(CH$_2$)$_4$— | | 1 | CO | NH | — |
| F | Me | Me | OH | H | —(CH$_2$)$_4$— | | 1 | CO | NH | — |
| Br | n-Pr | n-Pr | OH | H | —(CH$_2$)$_4$— | | 1 | CO | NH | — |
| Me | Me | Me | OH | H | Et | H | 1 | CO | NH | — |
| CF$_3$ | Me | Et | OH | H | —(CH$_2$)$_4$— | | 2 | CO | NH | CH$_2$ |
| CH$_2$CF$_3$ | Et | Me | OH | H | —(CH$_2$)$_4$— | | 1 | CO | NH | — |
| C$_2$F$_5$ | Me | Me | — | | Me | H | 1 | CO | NH | — |
| OMe | Me | Me | OH | H | —(CH$_2$)$_4$— | | 2 | CO | NH | — |
| OCF$_3$ | Me | Me | OH | H | —(CH$_2$)$_4$— | | 1 | CO | NH | — |
| CH$_2$OMe | Me | Me | OH | H | —(CH$_2$)$_4$— | | 1 | CO | NH | — |
| c-Pr | Me | Me | OH | H | —(CH$_2$)$_4$— | | 3 | CO | NH | — |
| NO$_2$ | Me | Me | OH | H | —(CH$_2$)$_4$— | | 1 | CO | NH | — |
| CN | Me | Me | OH | H | —(CH$_2$)$_4$— | | 1 | CO | NH | — |
| CHO | Me | Me | OH | H | —(CH$_2$)$_4$— | | 1 | CH$_2$ | NH | — |
| CO$_2$H | Me | Me | OH | H | —(CH$_2$)$_4$— | | 1 | CO | NH | — |
| OH | Me | Me | OH | H | —(CH$_2$)$_4$— | | 1 | CH$_2$ | NH | CH$_2$ |
| CH$_2$OH | Me | Me | — | | —(CH$_2$)$_4$— | | 1 | CO | NH | — |
| NHCHO | Me | Me | OH | H | —(CH$_2$)$_4$— | | 1 | NH | CO | NH |
| NHCN | Me | Me | OH | H | c-Pr | H | 1 | CO | NH | — |
| NH$_2$ | Me | Me | OAc | H | —(CH$_2$)$_4$— | | 1 | CO | NH | — |
| NHMe | Me | Me | OAc | H | —(CH$_2$)$_4$— | | 1 | CO | NH | — |
| NMe$_2$ | Me | Me | OAc | H | —(CH$_2$)$_4$— | | 1 | CO | NH | — |
| NHCOMe | Me | Me | OH | H | —(CH$_2$)$_4$— | | 1 | CO | NH | CH$_2$ |
| NHSO$_2$Me | Me | Me | OH | H | —(CH$_2$)$_4$— | | 1 | CO | NH | — |
| CONH$_2$ | Me | Me | OH | H | —(CH$_2$)$_4$— | | 4 | CO | NH | — |
| CONHMe | Me | Me | OH | H | —(CH$_2$)$_4$— | | 3 | CO | NH | — |
| CONMe$_2$ | Me | Me | OH | H | —(CH$_2$)$_4$— | | 2 | CO | NH | — |
| COMe | Me | Me | OH | H | Et | H | 1 | CO | NH | — |
| CO$_2$Me | Me | Me | OH | H | Me | H | 1 | CO | NH | — |
| CO$_2$Ph | Me | Me | OAc | H | i-Pr | H | 1 | CO | NH | — |
| CO$_2$CH$_2$Ph | Me | Me | OH | H | —(CH$_2$)$_4$— | | 1 | CO | NH | — |

TABLE 5

Example of Compounds

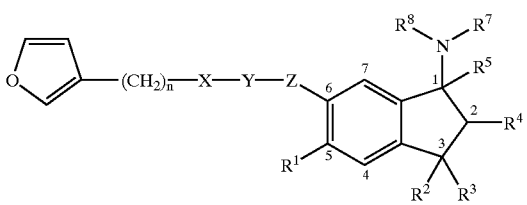

| R¹ | R² | R³ | R⁴ | R⁵ | R⁷ | R⁸ | n | X | Y | Z |
|---|---|---|---|---|---|---|---|---|---|---|
| H | Me | Me | OH | H | —(CH$_2$)$_4$— | | 1 | CO | NH | — |
| F | Me | Me | OH | H | —(CH$_2$)$_4$— | | 1 | CO | NH | — |
| Br | n-Pr | n-Pr | OH | H | —(CH$_2$)$_4$— | | 1 | CO | NH | — |
| Me | Me | Me | OH | H | Et | H | 1 | CO | NH | — |
| CF$_3$ | Me | Et | OH | H | —(CH$_2$)$_4$— | | 2 | CO | NH | CH$_2$ |
| CH$_2$CF$_3$ | Et | Me | OH | H | —(CH$_2$)$_4$— | | 1 | CO | NH | — |
| C$_2$F$_5$ | Me | Me | — | | Me | H | 1 | CO | NH | — |
| OMe | Me | Me | OH | H | —(CH$_2$)$_4$— | | 2 | CO | NH | — |
| OCF$_3$ | Me | Me | OH | H | —(CH$_2$)$_4$— | | 1 | CO | NH | — |

TABLE 5-continued

Example of Compounds

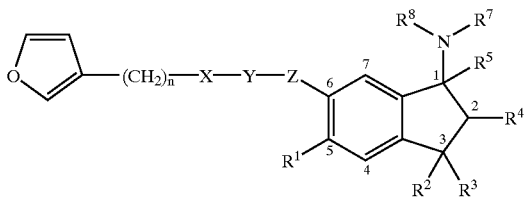

| R¹ | R² | R³ | R⁴ | R⁵ | R⁷ | R⁸ | n | X | Y | Z |
|---|---|---|---|---|---|---|---|---|---|---|
| CH₂OMe | Me | Me | OH | H | —(CH₂)₄— | | 1 | CO | NH | — |
| c-Pr | Me | Me | OH | H | —(CH₂)₄— | | 3 | CO | NH | — |
| NO₂ | Me | Me | OH | H | —(CH₂)₄— | | 1 | CO | NH | — |
| CN | Me | Me | OH | H | —(CH₂)₄— | | 1 | CO | NH | — |
| CHO | Me | Me | OH | H | —(CH₂)₄— | | 1 | CH₂ | NH | — |
| CO₂H | Me | Me | OH | H | —(CH₂)₄— | | 1 | CO | NH | — |
| OH | Me | Me | OH | H | —(CH₂)₄— | | 1 | CH₂ | NH | CH₂ |
| CH₂OH | Me | Me | — | | —(CH₂)₄— | | 1 | CO | NH | — |
| NHCHO | Me | Me | OH | H | —(CH₂)₄— | | 1 | NH | CO | NH |
| NHCN | Me | Me | OH | H | c-Pr | H | 1 | CO | NH | — |
| NH₂ | Me | Me | OAc | H | —(CH₂)₄— | | 1 | CO | NH | — |
| NHMe | Me | Me | OAc | H | —(CH₂)₄— | | 1 | CO | NH | — |
| NMe₂ | Me | Me | OAc | H | —(CH₂)₄— | | 1 | CO | NH | — |
| NHCOMe | Me | Me | OH | H | —(CH₂)₄— | | 1 | CO | NH | CH₂ |
| NHSO₂Me | Me | Me | OH | H | —(CH₂)₄— | | 1 | CO | NH | — |
| CONH₂ | Me | Me | OH | H | —(CH₂)₄— | | 4 | CO | NH | — |
| CONHMe | Me | Me | OH | H | —(CH₂)₄— | | 3 | CO | NH | — |
| CONMe₂ | Me | Me | OH | H | —(CH₂)₄— | | 2 | CO | NH | — |
| COMe | Me | Me | OH | H | Et | H | 1 | CO | NH | — |
| CO₂Me | Me | Me | OH | H | Me | H | 1 | CO | NH | — |
| CO₂Ph | Me | Me | OAc | H | i-Pr | H | 1 | CO | NH | — |
| CO₂CH₂Ph | Me | Me | OH | H | —(CH₂)₄— | | 1 | CO | NH | — |

TABLE 6

Example of Compounds

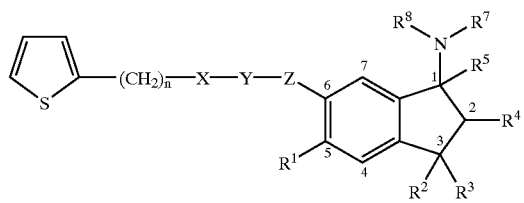

| R¹ | R² | R³ | R⁴ | R⁵ | R⁷ | R⁸ | n | X | Y | Z |
|---|---|---|---|---|---|---|---|---|---|---|
| H | Me | Me | OH | H | —(CH₂)₄— | | 1 | CO | NH | — |
| F | Me | Me | OH | H | —(CH₂)₄— | | 1 | CO | NH | — |
| Br | n-Pr | n-Pr | OH | H | —(CH₂)₄— | | 1 | CO | NH | — |
| Me | Me | Me | OH | H | Et | H | 1 | CO | NH | — |
| CF₃ | Me | Et | OH | H | —(CH₂)₄— | | 2 | CO | NH | CH₂ |
| CH₂CF₃ | Et | Me | OH | H | —(CH₂)₄— | | 1 | CO | NH | — |
| C₂F₅ | Me | Me | — | | Me | H | 1 | CO | NH | — |
| OMe | Me | Me | OH | H | —(CH₂)₄— | | 2 | CO | NH | — |
| OCF₃ | Me | Me | OH | H | —(CH₂)₄— | | 1 | CO | NH | — |
| CH₂OMe | Me | Me | OH | H | —(CH₂)₄— | | 1 | CO | NH | — |
| c-Pr | Me | Me | OH | H | —(CH₂)₄— | | 3 | CO | NH | — |
| NO₂ | Me | Me | OH | H | —(CH₂)₄— | | 1 | CO | NH | — |
| CN | Me | Me | OH | H | —(CH₂)₄— | | 1 | CO | NH | — |
| CHO | Me | Me | OH | H | —(CH₂)₄— | | 1 | CH₂ | NH | — |
| CO₂H | Me | Me | OH | H | —(CH₂)₄— | | 1 | CO | NH | — |
| OH | Me | Me | OH | H | —(CH₂)₄— | | 1 | CH₂ | NH | CH₂ |
| CH₂OH | Me | Me | — | | —(CH₂)₄— | | 1 | CO | NH | — |
| NHCHO | Me | Me | OH | H | —(CH₂)₄— | | 1 | NH | CO | NH |
| NHCN | Me | Me | OH | H | c-Pr | H | 1 | CO | NH | — |
| NH₂ | Me | Me | OAc | H | —(CH₂)₄— | | 1 | CO | NH | — |
| NHMe | Me | Me | OAc | H | —(CH₂)₄— | | 1 | CO | NH | — |
| NMe₂ | Me | Me | OAc | H | —(CH₂)₄— | | 1 | CO | NH | — |
| NHCOMe | Me | Me | OH | H | —(CH₂)₄— | | 1 | CO | NH | CH₂ |

TABLE 6-continued

Example of Compounds

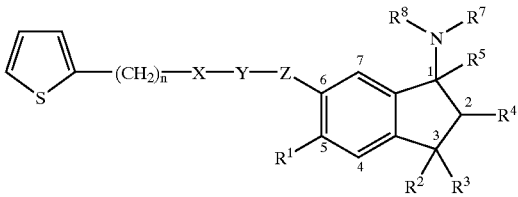

| $R^1$ | $R^2$ | $R^3$ | $R^4$ | $R^5$ | $R^7$ | $R^8$ | n | X | Y | Z |
|---|---|---|---|---|---|---|---|---|---|---|
| NHSO$_2$Me | Me | Me | OH | H | —(CH$_2$)$_4$— | | 1 | CO | NH | — |
| CONH$_2$ | Me | Me | OH | H | —(CH$_2$)$_4$— | | 4 | CO | NH | — |
| CONHMe | Me | Me | OH | H | —(CH$_2$)$_4$— | | 3 | CO | NH | — |
| CONMe$_2$ | Me | Me | OH | H | —(CH$_2$)$_4$— | | 2 | CO | NH | — |
| COMe | Me | Me | OH | H | Et | H | 1 | CO | NH | — |
| CO$_2$Me | Me | Me | OH | H | Me | H | 1 | CO | NH | — |
| CO$_2$Ph | Me | Me | OAc | H | i-Pr | H | 1 | CO | NH | — |
| CO$_2$CH$_2$Ph | Me | Me | OH | H | —(CH$_2$)$_4$— | | 1 | CO | NH | — |

TABLE 7

Example of Compounds

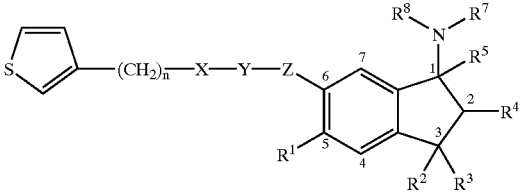

| $R^1$ | $R^2$ | $R^3$ | $R^4$ | $R^5$ | $R^7$ | $R^8$ | n | X | Y | Z |
|---|---|---|---|---|---|---|---|---|---|---|
| H | Me | Me | OH | H | —(CH$_2$)$_4$— | | 1 | CO | NH | — |
| F | Me | Me | OH | H | —(CH$_2$)$_4$— | | 1 | CO | NH | — |
| Br | n-Pr | n-Pr | OH | H | —(CH$_2$)$_4$— | | 1 | CO | NH | — |
| Me | Me | Me | OH | H | Et | H | 1 | CO | NH | — |
| CF$_3$ | Me | Et | OH | H | —(CH$_2$)$_4$— | | 2 | CO | NH | CH$_2$ |
| CH$_2$CF$_3$ | Et | Me | OH | H | —(CH$_2$)$_4$— | | 1 | CO | NH | — |
| C$_2$F$_5$ | Me | Me | — | | Me | H | 1 | CO | NH | — |
| OMe | Me | Me | OH | H | —(CH$_2$)$_4$— | | 2 | CO | NH | — |
| OCF$_3$ | Me | Me | OH | H | —(CH$_2$)$_4$— | | 1 | CO | NH | — |
| CH$_2$OMe | Me | Me | OH | H | —(CH$_2$)$_4$— | | 1 | CO | NH | — |
| c-Pr | Me | Me | OH | H | —(CH$_2$)$_4$— | | 3 | CO | NH | — |
| NO$_2$ | Me | Me | OH | H | —(CH$_2$)$_4$— | | 1 | CO | NH | — |
| CN | Me | Me | OH | H | —(CH$_2$)$_4$— | | 1 | CO | NH | — |
| CHO | Me | Me | OH | H | —(CH$_2$)$_4$— | | 1 | CH$_2$ | NH | — |
| CO$_2$H | Me | Me | OH | H | —(CH$_2$)$_4$— | | 1 | CO | NH | — |
| OH | Me | Me | OH | H | —(CH$_2$)$_4$— | | 1 | CH$_2$ | NH | CH$_2$ |
| CH$_2$OH | Me | Me | — | | —(CH$_2$)$_4$— | | 1 | CO | NH | — |
| NHCHO | Me | Me | OH | H | —(CH$_2$)$_4$— | | 1 | NH | CO | NH |
| NHCN | Me | Me | OH | H | c-Pr | H | 1 | CO | NH | — |
| NH$_2$ | Me | Me | OAc | H | —(CH$_2$)$_4$— | | 1 | CO | NH | — |
| NHMe | Me | Me | OAc | H | —(CH$_2$)$_4$— | | 1 | CO | NH | — |
| NMe$_2$ | Me | Me | OAc | H | —(CH$_2$)$_4$— | | 1 | CO | NH | — |
| NHCOMe | Me | Me | OH | H | —(CH$_2$)$_4$— | | 1 | CO | NH | CH$_2$ |
| NHSO$_2$Me | Me | Me | OH | H | —(CH$_2$)$_4$— | | 1 | CO | NH | — |
| CONH$_2$ | Me | Me | OH | H | —(CH$_2$)$_4$— | | 4 | CO | NH | — |
| CONHMe | Me | Me | OH | H | —(CH$_2$)$_4$— | | 3 | CO | NH | — |
| CONMe$_2$ | Me | Me | OH | H | —(CH$_2$)$_4$— | | 2 | CO | NH | — |
| COMe | Me | Me | OH | H | Et | H | 1 | CO | NH | — |
| CO$_2$Me | Me | Me | OH | H | Me | H | 1 | CO | NH | — |
| CO$_2$Ph | Me | Me | OAc | H | i-Pr | H | 1 | CO | NH | — |
| CO$_2$CH$_2$Ph | Me | Me | OH | H | —(CH$_2$)$_4$— | | 1 | CO | NH | — |

TABLE 8

Example of Compounds

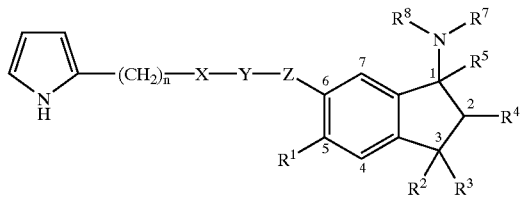

| R¹ | R² | R³ | R⁴ | R⁵ | R⁷ | R⁸ | n | X | Y | Z |
|---|---|---|---|---|---|---|---|---|---|---|
| H | Me | Me | OH | H | —(CH$_2$)$_4$— | | 1 | CO | NH | — |
| F | Me | Me | OH | H | —(CH$_2$)$_4$— | | 1 | CO | NH | — |
| Br | n-Pr | n-Pr | OH | H | —(CH$_2$)$_4$— | | 1 | CO | NH | — |
| Me | Me | Me | OH | H | Et | H | 1 | CO | NH | — |
| CF$_3$ | Me | Et | OH | H | —(CH$_2$)$_4$— | | 2 | CO | NH | CH$_2$ |
| CH$_2$CF$_3$ | Et | Me | OH | H | —(CH$_2$)$_4$— | | 1 | CO | NH | — |
| C$_2$F$_5$ | Me | Me | — | | Me | H | 1 | CO | NH | — |
| OMe | Me | Me | OH | H | —(CH$_2$)$_4$— | | 2 | CO | NH | — |
| OCF$_3$ | Me | Me | OH | H | —(CH$_2$)$_4$— | | 1 | CO | NH | — |
| CH$_2$OMe | Me | Me | OH | H | —(CH$_2$)$_4$— | | 1 | CO | NH | — |
| c-Pr | Me | Me | OH | H | —(CH$_2$)$_4$— | | 3 | CO | NH | — |
| NO$_2$ | Me | Me | OH | H | —(CH$_2$)$_4$— | | 1 | CO | NH | — |
| CN | Me | Me | OH | H | —(CH$_2$)$_4$— | | 1 | CO | NH | — |
| CHO | Me | Me | OH | H | —(CH$_2$)$_4$— | | 1 | CH$_2$ | NH | — |
| CO$_2$H | Me | Me | OH | H | —(CH$_2$)$_4$— | | 1 | CO | NH | — |
| OH | Me | Me | OH | H | —(CH$_2$)$_4$— | | 1 | CH$_2$ | NH | CH$_2$ |
| CH$_2$OH | Me | Me | — | | —(CH$_2$)$_4$— | | 1 | CO | NH | — |
| NHCHO | Me | Me | OH | H | —(CH$_2$)$_4$— | | 1 | NH | CO | NH |
| NHCN | Me | Me | OH | H | c-Pr | H | 1 | CO | NH | — |
| NH$_2$ | Me | Me | OAc | H | —(CH$_2$)$_4$— | | 1 | CO | NH | — |
| NHMe | Me | Me | OAc | H | —(CH$_2$)$_4$— | | 1 | CO | NH | — |
| NMe$_2$ | Me | Me | OAc | H | —(CH$_2$)$_4$— | | 1 | CO | NH | — |
| NHCOMe | Me | Me | OH | H | —(CH$_2$)$_4$— | | 1 | CO | NH | CH$_2$ |
| NHSO$_2$Me | Me | Me | OH | H | —(CH$_2$)$_4$— | | 1 | CO | NH | — |
| CONH$_2$ | Me | Me | OH | H | —(CH$_2$)$_4$— | | 4 | CO | NH | — |
| CONHMe | Me | Me | OH | H | —(CH$_2$)$_4$— | | 3 | CO | NH | — |
| CONMe$_2$ | Me | Me | OH | H | —(CH$_2$)$_4$— | | 2 | CO | NH | — |
| COMe | Me | Me | OH | H | Et | H | 1 | CO | NH | — |
| CO$_2$Me | Me | Me | OH | H | Me | H | 1 | CO | NH | — |
| CO$_2$Ph | Me | Me | OAc | H | i-Pr | H | 1 | CO | NH | — |
| CO$_2$CH$_2$Ph | Me | Me | OH | H | —(CH$_2$)$_4$— | | 1 | CO | NH | — |

TABLE 9

Example of Compounds

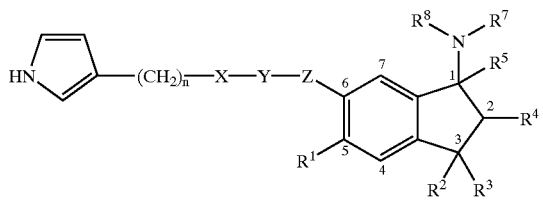

| R¹ | R² | R³ | R⁴ | R⁵ | R⁷ | R⁸ | n | X | Y | Z |
|---|---|---|---|---|---|---|---|---|---|---|
| H | Me | Me | OH | H | —(CH$_2$)$_4$— | | 1 | CO | NH | — |
| F | Me | Me | OH | H | —(CH$_2$)$_4$— | | 1 | CO | NH | — |
| Br | n-Pr | n-Pr | OH | H | —(CH$_2$)$_4$— | | 1 | CO | NH | — |
| Me | Me | Me | OH | H | Et | H | 1 | CO | NH | — |
| CF$_3$ | Me | Et | OH | H | —(CH$_2$)$_4$— | | 2 | CO | NH | CH$_2$ |
| CH$_2$CF$_3$ | Et | Me | OH | H | —(CH$_2$)$_4$— | | 1 | CO | NH | — |
| C$_2$F$_5$ | Me | Me | — | | Me | H | 1 | CO | NH | — |
| OMe | Me | Me | OH | H | —(CH$_2$)$_4$— | | 2 | CO | NH | — |
| OCF$_3$ | Me | Me | OH | H | —(CH$_2$)$_4$— | | 1 | CO | NH | — |
| CH$_2$OMe | Me | Me | OH | H | —(CH$_2$)$_4$— | | 1 | CO | NH | — |
| c-Pr | Me | Me | OH | H | —(CH$_2$)$_4$— | | 3 | CO | NH | — |

TABLE 9-continued

Example of Compounds

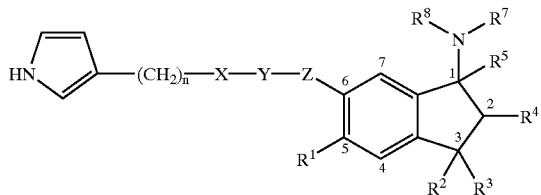

| R¹ | R² | R³ | R⁴ | R⁵ | R⁷ | R⁸ | n | X | Y | Z |
|---|---|---|---|---|---|---|---|---|---|---|
| NO₂ | Me | Me | OH | H | —(CH₂)₄— | | 1 | CO | NH | — |
| CN | Me | Me | OH | H | —(CH₂)₄— | | 1 | CO | NH | — |
| CHO | Me | Me | OH | H | —(CH₂)₄— | | 1 | CH₂ | NH | — |
| CO₂H | Me | Me | OH | H | —(CH₂)₄— | | 1 | CO | NH | — |
| OH | Me | Me | OH | H | —(CH₂)₄— | | 1 | CH₂ | NH | CH₂ |
| CH₂OH | Me | Me | — | | —(CH₂)₄— | | 1 | CO | NH | — |
| NHCHO | Me | Me | OH | H | —(CH₂)₄— | | 1 | NH | CO | NH |
| NHCN | Me | Me | OH | H | c-Pr | H | 1 | CO | NH | — |
| NH₂ | Me | Me | OAc | H | —(CH₂)₄— | | 1 | CO | NH | — |
| NHMe | Me | Me | OAc | H | —(CH₂)₄— | | 1 | CO | NH | — |
| NMe₂ | Me | Me | OAc | H | —(CH₂)₄— | | 1 | CO | NH | — |
| NHCOMe | Me | Me | OH | H | —(CH₂)₄— | | 1 | CO | NH | CH₂ |
| NHSO₂Me | Me | Me | OH | H | —(CH₂)₄— | | 1 | CO | NH | — |
| CONH₂ | Me | Me | OH | H | —(CH₂)₄— | | 4 | CO | NH | — |
| CONHMe | Me | Me | OH | H | —(CH₂)₄— | | 3 | CO | NH | — |
| CONMe₂ | Me | Me | OH | H | —(CH₂)₄— | | 2 | CO | NH | — |
| COMe | Me | Me | OH | H | Et | H | 1 | CO | NH | — |
| CO₂Me | Me | Me | OH | H | Me | H | 1 | CO | NH | — |
| CO₂Ph | Me | Me | OAc | H | i-Pr | H | 1 | CO | NH | — |
| CO₂CH₂Ph | Me | Me | OH | H | —(CH₂)₄— | | 1 | CO | NH | — |

TABLE 10

Example of Compounds

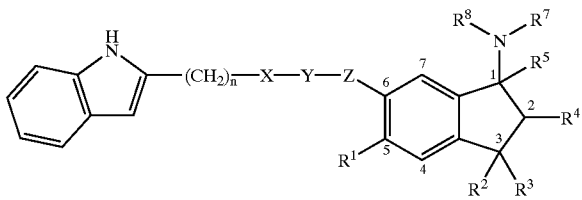

| R¹ | R² | R³ | R⁴ | R⁵ | R⁷ | R⁸ | n | X | Y | Z |
|---|---|---|---|---|---|---|---|---|---|---|
| H | Me | Me | OH | H | —(CH₂)₄— | | 1 | CO | NH | — |
| F | Me | Me | OH | H | —(CH₂)₄— | | 1 | CO | NH | — |
| Br | n-Pr | n-Pr | OH | H | —(CH₂)₄— | | 1 | CO | NH | — |
| Me | Me | Me | OH | H | Et | H | 1 | CO | NH | — |
| CF₃ | Me | Et | OH | H | —(CH₂)₄— | | 2 | CO | NH | CH₂ |
| CH₂CF₃ | Et | Me | OH | H | —(CH₂)₄— | | 1 | CO | NH | — |
| C₂F₅ | Me | Me | — | | Me | H | 1 | CO | NH | — |
| OMe | Me | Me | OH | H | —(CH₂)₄— | | 2 | CO | NH | — |
| OCF₃ | Me | Me | OH | H | —(CH₂)₄— | | 1 | CO | NH | — |
| CH₂OMe | Me | Me | OH | H | —(CH₂)₄— | | 1 | CO | NH | — |
| c-Pr | Me | Me | OH | H | —(CH₂)₄— | | 3 | CO | NH | — |
| NO₂ | Me | Me | OH | H | —(CH₂)₄— | | 1 | CO | NH | — |
| CN | Me | Me | OH | H | —(CH₂)₄— | | 1 | CO | NH | — |
| CHO | Me | Me | OH | H | —(CH₂)₄— | | 1 | CH₂ | NH | — |
| CO₂H | Me | Me | OH | H | —(CH₂)₄— | | 1 | CO | NH | — |
| OH | Me | Me | OH | H | —(CH₂)₄— | | 1 | CH₂ | NH | CH₂ |
| CH₂OH | Me | Me | — | | —(CH₂)₄— | | 1 | CO | NH | — |
| NHCHO | Me | Me | OH | H | —(CH₂)₄— | | 1 | NH | CO | NH |
| NHCN | Me | Me | OH | H | c-Pr | H | 1 | CO | NH | — |
| NH₂ | Me | Me | OAc | H | —(CH₂)₄— | | 1 | CO | NH | — |
| NHMe | Me | Me | OAc | H | —(CH₂)₄— | | 1 | CO | NH | — |
| NMe₂ | Me | Me | OAc | H | —(CH₂)₄— | | 1 | CO | NH | — |

TABLE 10-continued

Example of Compounds

| R¹ | R² | R³ | R⁴ | R⁵ | R⁷ | R⁸ | n | X | Y | Z |
|---|---|---|---|---|---|---|---|---|---|---|
| NHCOMe | Me | Me | OH | H | —(CH₂)₄— | | 1 | CO | NH | CH₂ |
| NHSO₂Me | Me | Me | OH | H | —(CH₂)₄— | | 1 | CO | NH | — |
| CONH₂ | Me | Me | OH | H | —(CH₂)₄— | | 4 | CO | NH | — |
| CONHMe | Me | Me | OH | H | —(CH₂)₄— | | 3 | CO | NH | — |
| CONMe₂ | Me | Me | OH | H | —(CH₂)₄— | | 2 | CO | NH | — |
| COMe | Me | Me | OH | H | Et | H | 1 | CO | NH | — |
| CO₂Me | Me | Me | OH | H | Me | H | 1 | CO | NH | — |
| CO₂Ph | Me | Me | OAc | H | i-Pr | H | 1 | CO | NH | — |
| CO₂CH₂Ph | Me | Me | OH | H | —(CH₂)₄— | | 1 | CO | NH | — |

TABLE 11

Example of Compounds

| R¹ | R² | R³ | R⁴ | R⁵ | R⁷ | R⁸ | n | X | Y | Z |
|---|---|---|---|---|---|---|---|---|---|---|
| H | Me | Me | OH | H | —(CH₂)₄— | | 1 | CO | NH | — |
| F | Me | Me | OH | H | —(CH₂)₄— | | 1 | CO | NH | — |
| Br | n-Pr | n-Pr | OH | H | —(CH₂)₄— | | 1 | CO | NH | — |
| Me | Me | Me | OH | H | Et | H | 1 | CO | NH | — |
| CF₃ | Me | Et | OH | H | —(CH₂)₄— | | 2 | CO | NH | CH₂ |
| CH₂CF₃ | Et | Me | OH | H | —(CH₂)₄— | | 1 | CO | NH | — |
| C₂F₅ | Me | Me | — | | Me | H | 1 | CO | NH | — |
| OMe | Me | Me | OH | H | —(CH₂)₄— | | 2 | CO | NH | — |
| OCF₃ | Me | Me | OH | H | —(CH₂)₄— | | 1 | CO | NH | — |
| CH₂OMe | Me | Me | OH | H | —(CH₂)₄— | | 1 | CO | NH | — |
| c-Pr | Me | Me | OH | H | —(CH₂)₄— | | 3 | CO | NH | — |
| NO₂ | Me | Me | OH | H | —(CH₂)₄— | | 1 | CO | NH | — |
| CN | Me | Me | OH | H | —(CH₂)₄— | | 1 | CO | NH | — |
| CHO | Me | Me | OH | H | —(CH₂)₄— | | 1 | CH₂ | NH | — |
| CO₂H | Me | Me | OH | H | —(CH₂)₄— | | 1 | CO | NH | — |
| OH | Me | Me | OH | H | —(CH₂)₄— | | 1 | CH₂ | NH | CH₂ |
| CH₂OH | Me | Me | — | | —(CH₂)₄— | | 1 | CO | NH | — |
| NHCHO | Me | Me | OH | H | —(CH₂)₄— | | 1 | NH | CO | NH |
| NHCN | Me | Me | OH | H | c-Pr | H | 1 | CO | NH | — |
| NH₂ | Me | Me | OAc | H | —(CH₂)₄— | | 1 | CO | NH | — |
| NHMe | Me | Me | OAc | H | —(CH₂)₄— | | 1 | CO | NH | — |
| NMe₂ | Me | Me | OAc | H | —(CH₂)₄— | | 1 | CO | NH | — |
| NHCOMe | Me | Me | OH | H | —(CH₂)₄— | | 1 | CO | NH | CH₂ |
| NHSO₂Me | Me | Me | OH | H | —(CH₂)₄— | | 1 | CO | NH | — |
| CONH₂ | Me | Me | OH | H | —(CH₂)₄— | | 4 | CO | NH | — |
| CONHMe | Me | Me | OH | H | —(CH₂)₄— | | 3 | CO | NH | — |
| CONMe₂ | Me | Me | OH | H | —(CH₂)₄— | | 2 | CO | NH | — |
| COMe | Me | Me | OH | H | Et | H | 1 | CO | NH | — |
| CO₂Me | Me | Me | OH | H | Me | H | 1 | CO | NH | — |
| CO₂Ph | Me | Me | OAc | H | i-Pr | H | 1 | CO | NH | — |
| CO₂CH₂Ph | Me | Me | OH | H | —(CH₂)₄— | | 1 | CO | NH | — |

TABLE 12

Example of Compounds

| $R^1$ | $R^2$ | $R^3$ | $R^4$ | $R^5$ | $R^7$ | $R^8$ | n |
|---|---|---|---|---|---|---|---|
| $NO_2$ | Me | Me | OH | H | —$(CH_2)_4$— | | 0 |
| $NO_2$ | Me | Me | — | | —$(CH_2)_4$— | | 1 |
| $NO_2$ | Me | Me | OH | H | —$(CH_2)_4$— | | 2 |
| $NO_2$ | Me | Me | OH | H | Et | H | 3 |
| $NO_2$ | Me | Me | OH | H | i-Pr | H | 4 |
| $NO_2$ | Me | Me | OH | H | —$(CH_2)_3$— | | 1 |
| $NO_2$ | Me | Me | OH | H | —$(CH_2)_5$— | | 1 |
| CN | Me | Me | OH | H | —$(CH_2)_4$— | | 0 |
| CN | Me | Me | — | | —$(CH_2)_4$— | | 1 |
| CN | Me | Me | OH | H | —$(CH_2)_4$— | | 2 |
| CN | Me | Me | OH | H | Et | H | 3 |
| CN | Me | Me | OH | H | i-Pr | H | 4 |
| $NO_2$ | —$(CH_2)_2$— | | OH | H | —$(CH_2)_4$— | | 1 |
| $NO_2$ | —$(CH_2)_3$— | | OH | H | —$(CH_2)_4$— | | 1 |

TABLE 12-continued

Example of Compounds

| $R^1$ | $R^2$ | $R^3$ | $R^4$ | $R^5$ | $R^7$ | $R^8$ | n |
|---|---|---|---|---|---|---|---|
| $NO_2$ | —$(CH_2)_4$— | | OH | H | —$(CH_2)_4$— | | 1 |
| $NO_2$ | —$(CH_2)_5$— | | OH | H | —$(CH_2)_4$— | | 1 |
| $NO_2$ | Et | Et | OH | H | c-Pr | H | 0 |
| $NO_2$ | Et | Et | OH | H | —$(CH_2)_4$— | | 1 |
| $NO_2$ | Et | Et | OH | H | —$(CH_2)_4$— | | 2 |
| $NO_2$ | Et | Et | OH | H | —$(CH_2)_4$— | | 3 |
| $NO_2$ | Et | Et | OH | H | —$(CH_2)_4$— | | 4 |
| CN | Et | Et | OH | H | —$(CH_2)_4$— | | 1 |
| $NO_2$ | n-Pr | n-Pr | OH | H | —$(CH_2)_4$— | | 1 |
| CN | n-Pr | n-Pr | OH | H | —$(CH_2)_4$— | | 1 |
| $NO_2$ | i-Pr | i-Pr | OH | H | —$(CH_2)_4$— | | 1 |
| CN | i-Pr | i-Pr | OH | H | —$(CH_2)_4$— | | 1 |
| $NO_2$ | n-Bu | n-Bu | OH | H | —$(CH_2)_4$— | | 1 |
| $NO_2$ | i-Bu | i-Bu | OH | H | —$(CH_2)_4$— | | 1 |
| $NO_2$ | t-Bu | t-Bu | OH | H | —$(CH_2)_4$— | | 1 |
| $NO_2$ | n-Pe | n-Pe | OH | H | —$(CH_2)_4$— | | 1 |
| $NO_2$ | n-Hex | n-Hex | OH | H | —$(CH_2)_4$— | | 1 |

TABLE 13

Example of Compounds

| $R^1$ | $R^2$ | $R^3$ | $R^4$ | $R^5$ | $R^7$ | $R^8$ | n | X | Y | Z |
|---|---|---|---|---|---|---|---|---|---|---|
| H | Me | Me | OH | H | —$(CH_2)_4$— | | 2 | CO | NH | $CH_2$ |
| F | Me | Me | OH | H | —$(CH_2)_4$— | | 2 | CO | NH | $CH_2$ |
| Br | Me | Me | OH | H | Et | H | 2 | CO | NH | $CH_2$ |
| Me | Et | Et | OH | H | —$(CH_2)_4$— | | 1 | CO | NH | $CH_2$ |
| $CF_3$ | Me | Me | OH | H | —$(CH_2)_4$— | | 1 | CO | NH | — |
| $CH_2CF_3$ | Me | Me | — | | —$(CH_2)_4$— | | 1 | CO | NH | $CH_2$ |
| $C_2F_5$ | Me | Me | OH | H | —$(CH_2)_4$— | | 1 | CO | NH | $CH_2$ |
| OMe | Me | Me | OH | H | —$(CH_2)_4$— | | 1 | CO | NH | $CH_2$ |
| $OCF_3$ | Me | Me | OH | H | —$(CH_2)_4$— | | 1 | CO | NH | $CH_2$ |
| $CH_2OMe$ | Me | Me | OH | H | —$(CH_2)_4$— | | 1 | $CH_2$ | NH | — |
| c-Pr | Me | Me | OH | H | n-Pr | H | 1 | $CH_2$ | NH | — |
| $NO_2$ | Me | Me | OH | H | —$(CH_2)_4$— | | 1 | $CH_2$ | NH | — |
| CN | Me | Me | OH | H | —$(CH_2)_4$— | | 1 | $CH_2$ | NH | — |
| CHO | Me | Me | OH | H | —$(CH_2)_4$— | | 1 | $CH_2$ | NH | — |
| $CO_2H$ | Me | Me | OH | H | —$(CH_2)_4$— | | 1 | $CH_2$ | NH | — |
| OH | Me | Me | OH | H | —$(CH_2)_4$— | | 1 | CO | NH | — |
| $CH_2OH$ | Me | Me | OH | H | c-Pr | H | 1 | $CH_2$ | NH | $CH_2$ |
| NHCHO | Me | Me | OH | H | —$(CH_2)_4$— | | 2 | $CH_2$ | NH | $CH_2$ |
| NHCN | Me | Me | OH | H | n-Bu | H | 2 | $CH_2$ | NH | $CH_2$ |
| $NH_2$ | Me | Me | OH | H | —$(CH_2)_4$— | | 4 | $CH_2$ | NH | $CH_2$ |
| NHMe | Me | Me | OH | H | —$(CH_2)_4$— | | 3 | $CH_2$ | NH | $CH_2$ |
| $NMe_2$ | Me | Me | OH | H | —$(CH_2)_4$— | | 2 | $SO_2$ | NH | — |
| NHCOMe | Et | Et | OH | H | —$(CH_2)_4$— | | 1 | $SO_2$ | NH | — |
| $NHSO_2Me$ | Me | Me | OH | H | i-Pr | H | 1 | $SO_2$ | NH | — |
| $CONH_2$ | Me | Me | — | | —$(CH_2)_4$— | | 1 | $SO_2$ | NH | — |
| CONHMe | Me | Me | OAc | H | —$(CH_2)_4$— | | 1 | $SO_2$ | NH | — |

TABLE 13-continued

Example of Compounds

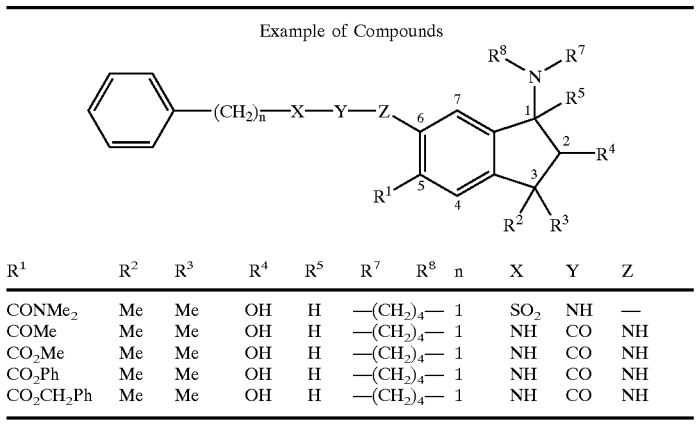

| R¹ | R² | R³ | R⁴ | R⁵ | R⁷ | R⁸ | n | X | Y | Z |
|---|---|---|---|---|---|---|---|---|---|---|
| CONMe₂ | Me | Me | OH | H | —(CH₂)₄— | | 1 | SO₂ | NH | — |
| COMe | Me | Me | OH | H | —(CH₂)₄— | | 1 | NH | CO | NH |
| CO₂Me | Me | Me | OH | H | —(CH₂)₄— | | 1 | NH | CO | NH |
| CO₂Ph | Me | Me | OH | H | —(CH₂)₄— | | 1 | NH | CO | NH |
| CO₂CH₂Ph | Me | Me | OH | H | —(CH₂)₄— | | 1 | NH | CO | NH |

TABLE 14

Example of Compounds

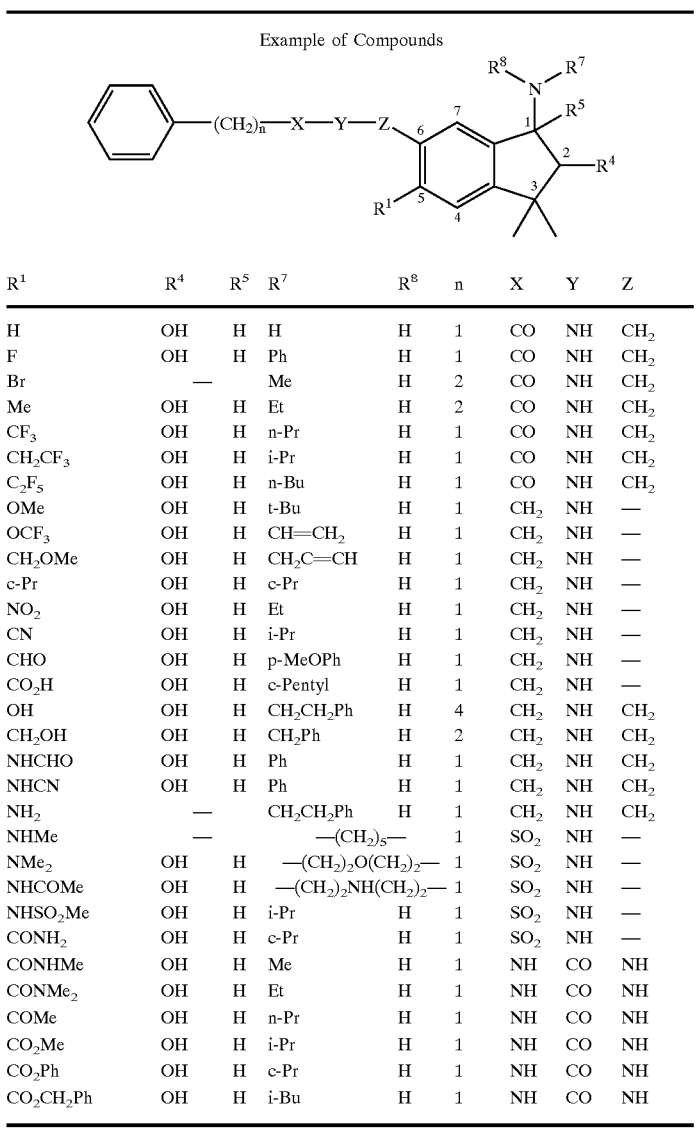

| R¹ | R⁴ | R⁵ | R⁷ | R⁸ | n | X | Y | Z |
|---|---|---|---|---|---|---|---|---|
| H | OH | H | H | H | 1 | CO | NH | CH₂ |
| F | OH | H | Ph | H | 1 | CO | NH | CH₂ |
| Br | — | | Me | H | 2 | CO | NH | CH₂ |
| Me | OH | H | Et | H | 2 | CO | NH | CH₂ |
| CF₃ | OH | H | n-Pr | H | 1 | CO | NH | CH₂ |
| CH₂CF₃ | OH | H | i-Pr | H | 1 | CO | NH | CH₂ |
| C₂F₅ | OH | H | n-Bu | H | 1 | CO | NH | CH₂ |
| OMe | OH | H | t-Bu | H | 1 | CH₂ | NH | — |
| OCF₃ | OH | H | CH=CH₂ | H | 1 | CH₂ | NH | — |
| CH₂OMe | OH | H | CH₂C≡CH | H | 1 | CH₂ | NH | — |
| c-Pr | OH | H | c-Pr | H | 1 | CH₂ | NH | — |
| NO₂ | OH | H | Et | H | 1 | CH₂ | NH | — |
| CN | OH | H | i-Pr | H | 1 | CH₂ | NH | — |
| CHO | OH | H | p-MeOPh | H | 1 | CH₂ | NH | — |
| CO₂H | OH | H | c-Pentyl | H | 1 | CH₂ | NH | — |
| OH | OH | H | CH₂CH₂Ph | H | 4 | CH₂ | NH | CH₂ |
| CH₂OH | OH | H | CH₂Ph | H | 2 | CH₂ | NH | CH₂ |
| NHCHO | OH | H | Ph | H | 1 | CH₂ | NH | CH₂ |
| NHCN | OH | H | Ph | H | 1 | CH₂ | NH | CH₂ |
| NH₂ | — | | CH₂CH₂Ph | H | 1 | CH₂ | NH | CH₂ |
| NHMe | — | | —(CH₂)₅— | | 1 | SO₂ | NH | — |
| NMe₂ | OH | H | —(CH₂)₂O(CH₂)₂— | | 1 | SO₂ | NH | — |
| NHCOMe | OH | H | —(CH₂)₂NH(CH₂)₂— | | 1 | SO₂ | NH | — |
| NHSO₂Me | OH | H | i-Pr | H | 1 | SO₂ | NH | — |
| CONH₂ | OH | H | c-Pr | H | 1 | SO₂ | NH | — |
| CONHMe | OH | H | Me | H | 1 | NH | CO | NH |
| CONMe₂ | OH | H | Et | H | 1 | NH | CO | NH |
| COMe | OH | H | n-Pr | H | 1 | NH | CO | NH |
| CO₂Me | OH | H | i-Pr | H | 1 | NH | CO | NH |
| CO₂Ph | OH | H | c-Pr | H | 1 | NH | CO | NH |
| CO₂CH₂Ph | OH | H | i-Bu | H | 1 | NH | CO | NH |

TABLE 15

Example of Compounds

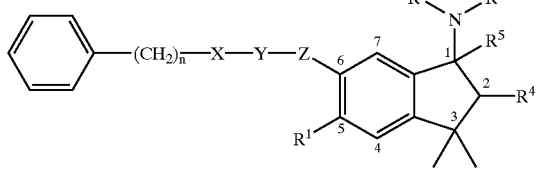

| R¹ | R⁴ | R⁵ | R⁷ | R⁸ | n | X | Y | Z |
|---|---|---|---|---|---|---|---|---|
| H | OH | H | H | H | 0 | NH | CO | NH |
| F | OH | H | Ph | H | 2 | CO | NH | — |
| Br | — | | Me | H | 2 | CO | NH | — |
| Me | OH | H | Et | H | 3 | CO | NH | — |
| $CF_3$ | OH | H | n-Pr | H | 4 | CO | NH | — |
| $CH_2CF_3$ | OH | H | i-Pr | H | 3 | CO | NH | — |
| $C_2F_5$ | OH | H | n-Bu | H | 4 | CO | NH | — |
| OMe | OH | H | t-Bu | H | 0 | CO | NH | — |
| $OCF_3$ | OH | H | $CH=CH_2$ | H | 2 | CO | NH | — |
| $CH_2OMe$ | OH | H | $CH_2C\equiv CH$ | H | 2 | CO | NH | — |
| c-Pr | OH | H | c-Pr | H | 0 | CO | NH | — |
| $NO_2$ | OH | H | Et | H | 2 | CO | NH | — |
| CN | OH | H | i-Pr | H | 2 | CO | NH | — |
| CHO | OH | H | p-MeOPh | H | 3 | CO | NH | — |
| $CO_2H$ | OH | H | c-Pentyl | H | 4 | CO | NH | — |
| OH | OH | H | $CH_2CH_2Ph$ | H | 3 | CO | NH | — |
| $CH_2OH$ | OH | H | $CH_2Ph$ | H | 2 | CO | NH | — |
| NHCHO | OH | H | Ph | H | 2 | CO | NH | — |
| NHCN | OH | H | Ph | H | 2 | CO | NH | — |
| $NH_2$ | — | | $CH_2CH_2Ph$ | H | 3 | CO | NH | — |
| NHMe | — | | —$(CH_2)_5$— | | 2 | CO | NH | — |
| $NMe_2$ | OH | H | —$(CH_2)_2O(CH_2)_2$— | | 2 | CO | NH | — |
| NHCOMe | OH | H | —$(CH_2)_2NH(CH_2)_2$— | | 3 | CO | NH | — |
| $NHSO_2Me$ | OH | H | i-Pr | H | 2 | CO | NH | — |
| $CONH_2$ | OH | H | c-Pr | H | 2 | CO | NH | — |
| CONHMe | OH | H | Me | H | 2 | CO | NH | — |
| $CONMe_2$ | OH | H | Et | H | 2 | CO | NH | — |
| COMe | OH | H | n-Pr | H | 2 | CO | NH | — |
| $CO_2Me$ | OH | H | i-Pr | H | 2 | CO | NH | — |
| $CO_2Ph$ | OH | H | c-Pr | H | 2 | CO | NH | — |
| $CO_2CH_2Ph$ | OH | H | i-Bu | H | 2 | CO | NH | — |

TABLE 16

Example of Compounds

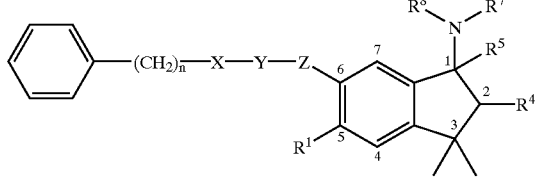

| R¹ | R⁴ | R⁵ | R⁷ | R⁸ | n | X | Y | Z |
|---|---|---|---|---|---|---|---|---|
| H | OH | H | $CH=CH_2$ | H | 1 | CO | NH | — |
| F | OH | H | $CH_2C\equiv CH$ | H | 1 | CO | NH | — |
| Br | — | | c-Pr | H | 1 | CO | NH | — |
| Me | OH | H | Et | H | 2 | CO | NH | — |
| $CF_3$ | OH | H | i-Pr | H | 2 | CO | NH | — |
| $CH_2CF_3$ | OH | H | p-MeOPh | H | 2 | CO | NH | — |
| $C_2F_5$ | OH | H | c-Pentyl | H | 1 | CO | NH | — |
| OMe | OH | H | $CH_2CH_2Ph$ | H | 1 | CO | NH | — |
| $OCF_3$ | OH | H | $CH_2Ph$ | H | 1 | CO | NH | — |
| $CH_2OMe$ | OH | H | Ph | H | 1 | CO | NH | — |
| c-Pr | OH | H | Ph | H | 1 | CO | NH | — |
| $NO_2$ | OH | H | $CH_2CH_2Ph$ | H | 1 | CO | NH | — |
| CN | OH | H | Me | H | 1 | CO | NH | — |

TABLE 16-continued

Example of Compounds

| R¹ | R⁴ | R⁵ | R⁷ | R⁸ | n | X | Y | Z |
|---|---|---|---|---|---|---|---|---|
| CHO | OH | H | Et | H | 1 | CO | NH | — |
| CO₂H | OH | H | n-Pr | H | 1 | CO | NH | — |
| OH | OH | H | i-Pr | H | 1 | NH | CO | NH |
| CH₂OH | OH | H | c-Pr | H | 1 | CO | NH | — |
| NHCHO | OH | H | i-Bu | H | 1 | CO | NH | — |
| NHCN | OH | H | H | H | 1 | CO | NH | — |
| NH₂ | — | | Ph | H | 1 | CH₂ | NH | — |
| NHMe | — | | Me | H | 1 | CH₂ | NH | — |
| NMe₂ | OH | H | Et | H | 1 | CH₂ | NH | — |
| NHCOMe | OH | H | n-Pr | H | 1 | CH₂ | NH | — |
| NHSO₂Me | OH | H | i-Pr | H | 1 | CH₂ | NH | — |
| CONH₂ | OH | H | n-Bu | H | 1 | CO | NH | — |
| CONHMe | OH | H | t-Bu | H | 1 | CO | NH | — |
| CONMe₂ | OH | H | —(CH₂)₅— | | 1 | CO | NH | — |
| COMe | OH | H | —(CH₂)₂O(CH₂)₂— | | 1 | CO | NH | — |
| CO₂Me | OH | H | —(CH₂)₂NH(CH₂)₂— | | 1 | CO | NH | — |
| CO₂Ph | OH | H | i-Pr | H | 1 | CO | NH | — |
| CO₂CH₂Ph | OH | H | c-Pr | H | 1 | CO | NH | — |

TABLE 17

Example of Compounds

| R¹ | R⁴ | R⁵ | R⁷ | R⁸ | n | X | Y | Z |
|---|---|---|---|---|---|---|---|---|
| H | OH | H | CH=CH₂ | H | 1 | CO | NH | — |
| F | OH | H | CH₂C≡CH | H | 1 | CO | NH | — |
| Br | — | | c-Pr | H | 1 | CO | NH | — |
| Me | OH | H | Et | H | 2 | CO | NH | — |
| CF₃ | OH | H | i-Pr | H | 2 | CO | NH | — |
| CH₂CF₃ | OH | H | p-MeOPh | H | 2 | CO | NH | — |
| C₂F₅ | OH | H | c-Pentyl | H | 1 | CO | NH | — |
| OMe | OH | H | CH₂CH₂Ph | H | 1 | CO | NH | — |
| OCF₃ | OH | H | CH₂Ph | H | 1 | CO | NH | — |
| CH₂OMe | OH | H | Ph | H | 1 | CO | NH | — |
| c-Pr | OH | H | Ph | H | 1 | CO | NH | — |
| NO₂ | OH | H | CH₂CH₂Ph | H | 1 | CO | NH | — |
| CN | OH | H | Me | H | 1 | CO | NH | — |
| CHO | OH | H | Et | H | 1 | CO | NH | — |
| CO₂H | OH | H | n-Pr | H | 1 | CO | NH | — |
| OH | OH | H | i-Pr | H | 1 | NH | CO | NH |
| CH₂OH | OH | H | c-Pr | H | 1 | CO | NH | — |
| NHCHO | OH | H | i-Bu | H | 1 | CO | NH | — |
| NHCN | OH | H | H | H | 1 | CO | NH | — |
| NH₂ | — | | Ph | H | 1 | CH₂ | NH | — |
| NHMe | — | | Me | H | 1 | CH₂ | NH | — |
| NMe₂ | OH | H | Et | H | 1 | CH₂ | NH | — |
| NHCOMe | OH | H | n-Pr | H | 1 | CH₂ | NH | — |
| NHSO₂Me | OH | H | i-Pr | H | 1 | CH₂ | NH | — |
| CONH₂ | OH | H | n-Bu | H | 1 | CO | NH | — |
| CONHMe | OH | H | t-Bu | H | 1 | CO | NH | — |

TABLE 17-continued

Example of Compounds (4-pyridyl)-(CH$_2$)$_n$-X-Y-Z attached at position 6 of indane; R$^1$ at position 5; R$^4$ at position 2; R$^5$ and NR$^7$R$^8$ at position 1; gem-dimethyl at position 3.

| R$^1$ | R$^4$ | R$^5$ | R$^7$ | R$^8$ | n | X | Y | Z |
|---|---|---|---|---|---|---|---|---|
| CONMe$_2$ | OH | H | —(CH$_2$)$_5$— | | 1 | CO | NH | — |
| COMe | OH | H | —(CH$_2$)$_2$O(CH$_2$)$_2$— | | 1 | CO | NH | — |
| CO$_2$Me | OH | H | —(CH$_2$)$_2$NH(CH$_2$)$_2$— | | 1 | CO | NH | — |
| CO$_2$Ph | OH | H | i-Pr | H | 1 | CO | NH | — |
| CO$_2$CH$_2$Ph | OH | H | c-Pr | H | 1 | CO | NH | — |

TABLE 18

Example of Compounds (3-pyridyl)-(CH$_2$)$_n$-X-Y-Z attached at position 6 of indane; R$^1$ at position 5; R$^4$ at position 2; R$^5$ and NR$^7$R$^8$ at position 1; gem-dimethyl at position 3.

| R$^1$ | R$^4$ | R$^5$ | R$^7$ | R$^8$ | n | X | Y | Z |
|---|---|---|---|---|---|---|---|---|
| H | OH | H | CH=CH$_2$ | H | 1 | CO | NH | — |
| F | OH | H | CH$_2$C≡CH | H | 1 | CO | NH | — |
| Br | — | | c-Pr | H | 1 | CO | NH | — |
| Me | OH | H | Et | H | 2 | CO | NH | — |
| CF$_3$ | OH | H | i-Pr | H | 2 | CO | NH | — |
| CH$_2$CF$_3$ | OH | H | p-MeOPh | H | 2 | CO | NH | — |
| C$_2$F$_5$ | OH | H | c-Pentyl | H | 1 | CO | NH | — |
| OMe | OH | H | CH$_2$CH$_2$Ph | H | 1 | CO | NH | — |
| OCF$_3$ | OH | H | CH$_2$Ph | H | 1 | CO | NH | — |
| CH$_2$OMe | OH | H | Ph | H | 1 | CO | NH | — |
| c-Pr | OH | H | Ph | H | 1 | CO | NH | — |
| NO$_2$ | OH | H | CH$_2$CH$_2$Ph | H | 1 | CO | NH | — |
| CN | OH | H | Me | H | 1 | CO | NH | — |
| CHO | OH | H | Et | H | 1 | CO | NH | — |
| CO$_2$H | OH | H | n-Pr | H | 1 | CO | NH | — |
| OH | OH | H | i-Pr | H | 1 | NH | CO | NH |
| CH$_2$OH | OH | H | c-Pr | H | 1 | CO | NH | — |
| NHCHO | OH | H | i-Bu | H | 1 | CO | NH | — |
| NHCN | OH | H | H | H | 1 | CO | NH | — |
| NH$_2$ | — | | Ph | H | 1 | CH$_2$ | NH | — |
| NHMe | — | | Me | H | 1 | CH$_2$ | NH | — |
| NMe$_2$ | OH | H | Et | H | 1 | CH$_2$ | NH | — |
| NHCOMe | OH | H | n-Pr | H | 1 | CH$_2$ | NH | — |
| NHSO$_2$Me | OH | H | i-Pr | H | 1 | CH$_2$ | NH | — |
| CONH$_2$ | OH | H | n-Bu | H | 1 | CO | NH | — |
| CONHMe | OH | H | t-Bu | H | 1 | CO | NH | — |
| CONMe$_2$ | OH | H | —(CH$_2$)$_5$— | | 1 | CO | NH | — |
| COMe | OH | H | —(CH$_2$)$_2$O(CH$_2$)$_2$— | | 1 | CO | NH | — |
| CO$_2$Me | OH | H | —(CH$_2$)$_2$NH(CH$_2$)$_2$— | | 1 | CO | NH | — |
| CO$_2$Ph | OH | H | i-Pr | H | 1 | CO | NH | — |
| CO$_2$CH$_2$Ph | OH | H | c-Pr | H | 1 | CO | NH | — |

TABLE 19

Example of Compounds

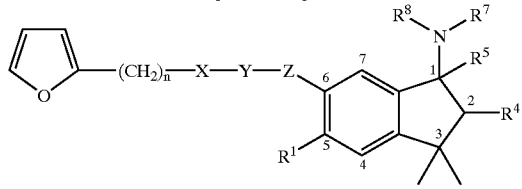

| R$^1$ | R$^4$ | R$^5$ | R$^7$ | R$^8$ | n | X | Y | Z |
|---|---|---|---|---|---|---|---|---|
| H | OH | H | CH=CH$_2$ | H | 1 | CO | NH | — |
| F | OH | H | CH$_2$C=CH | H | 1 | CO | NH | — |
| Br | — | | c-Pr | H | 1 | CO | NH | — |
| Me | OH | H | Et | H | 2 | CO | NH | — |
| CF$_3$ | OH | H | i-Pr | H | 2 | CO | NH | — |
| CH$_2$CF$_3$ | OH | H | p-MeOPh | H | 2 | CO | NH | — |
| C$_2$F$_5$ | OH | H | c-Pentyl | H | 1 | CO | NH | — |
| OMe | OH | H | CH$_2$CH$_2$Ph | H | 1 | CO | NH | — |
| OCF$_3$ | OH | H | CH$_2$Ph | H | 1 | CO | NH | — |
| CH$_2$OMe | OH | H | Ph | H | 1 | CO | NH | — |
| c-Pr | OH | H | Ph | H | 1 | CO | NH | — |
| NO$_2$ | OH | H | CH$_2$CH$_2$Ph | H | 1 | CO | NH | — |
| CN | OH | H | Me | H | 1 | CO | NH | — |
| CHO | OH | H | Et | H | 1 | CO | NH | — |
| CO$_2$H | OH | H | n-Pr | H | 1 | CO | NH | — |
| OH | OH | H | i-Pr | H | 1 | NH | CO | NH |
| CH$_2$OH | OH | H | c-Pr | H | 1 | CO | NH | — |
| NHCHO | OH | H | i-Bu | H | 1 | CO | NH | — |
| NHCN | OH | H | H | H | 1 | CO | NH | — |
| NH$_2$ | — | | Ph | H | 1 | CH$_2$ | NH | — |
| NHMe | — | | Me | H | 1 | CH$_2$ | NH | — |
| NMe$_2$ | OH | H | Et | H | 1 | CH$_2$ | NH | — |
| NHCOMe | OH | H | n-Pr | H | 1 | CH$_2$ | NH | — |
| NHSO$_2$Me | OH | H | i-Pr | H | 1 | CH$_2$ | NH | — |
| CONH$_2$ | OH | H | n-Bu | H | 1 | CO | NH | — |
| CONHMe | OH | H | t-Bu | H | 1 | CO | NH | — |
| CONMe$_2$ | OH | H | —(CH$_2$)$_5$— | | 1 | CO | NH | — |
| COMe | OH | H | —(CH$_2$)$_2$O(CH$_2$)$_2$— | | 1 | CO | NH | — |
| CO$_2$Me | OH | H | —(CH$_2$)$_2$NH(CH$_2$)$_2$— | | 1 | CO | NH | — |
| CO$_2$Ph | OH | H | i-Pr | H | 1 | CO | NH | — |
| CO$_2$CH$_2$Ph | OH | H | c-Pr | H | 1 | CO | NH | — |

TABLE 20

Example of Compounds

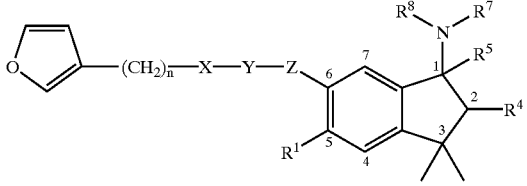

| R$^1$ | R$^4$ | R$^5$ | R$^7$ | R$^8$ | n | X | Y | Z |
|---|---|---|---|---|---|---|---|---|
| H | OH | H | CH=CH$_2$ | H | 1 | CO | NH | — |
| F | OH | H | CH$_2$C=CH | H | 1 | CO | NH | — |
| Br | — | | c-Pr | H | 1 | CO | NH | — |
| Me | OH | H | Et | H | 2 | CO | NH | — |
| CF$_3$ | OH | H | i-Pr | H | 2 | CO | NH | — |
| CH$_2$CF$_3$ | OH | H | p-MeOPh | H | 2 | CO | NH | — |
| C$_2$F$_5$ | OH | H | c-Pentyl | H | 1 | CO | NH | — |
| OMe | OH | H | CH$_2$CH$_2$Ph | H | 1 | CO | NH | — |
| OCF$_3$ | OH | H | CH$_2$Ph | H | 1 | CO | NH | — |
| CH$_2$OMe | OH | H | Ph | H | 1 | CO | NH | — |
| c-Pr | OH | H | Ph | H | 1 | CO | NH | — |
| NO$_2$ | OH | H | CH$_2$CH$_2$Ph | H | 1 | CO | NH | — |
| CN | OH | H | Me | H | 1 | CO | NH | — |

TABLE 20-continued

Example of Compounds

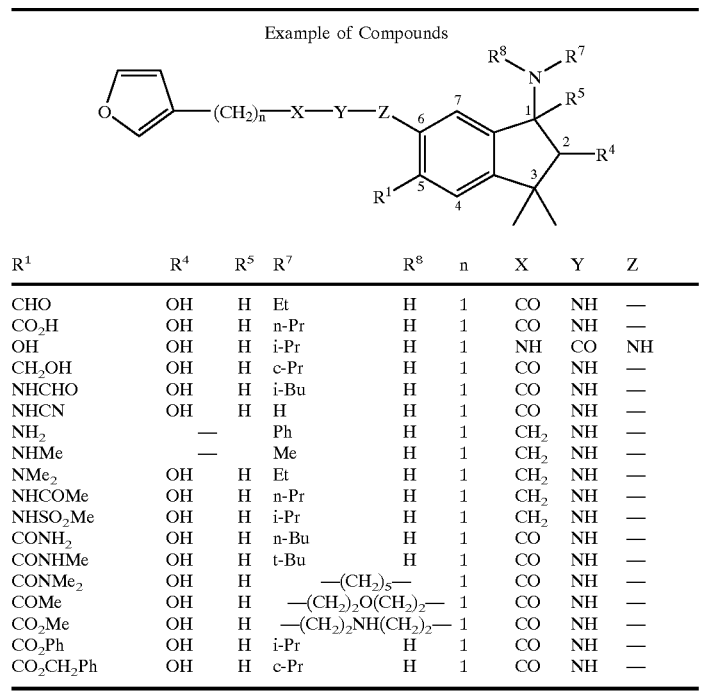

| R¹ | R⁴ | R⁵ | R⁷ | R⁸ | n | X | Y | Z |
|---|---|---|---|---|---|---|---|---|
| CHO | OH | H | Et | H | 1 | CO | NH | — |
| CO₂H | OH | H | n-Pr | H | 1 | CO | NH | — |
| OH | OH | H | i-Pr | H | 1 | NH | CO | NH |
| CH₂OH | OH | H | c-Pr | H | 1 | CO | NH | — |
| NHCHO | OH | H | i-Bu | H | 1 | CO | NH | — |
| NHCN | OH | H | H | H | 1 | CO | NH | — |
| NH₂ | — | | Ph | H | 1 | CH₂ | NH | — |
| NHMe | — | | Me | H | 1 | CH₂ | NH | — |
| NMe₂ | OH | H | Et | H | 1 | CH₂ | NH | — |
| NHCOMe | OH | H | n-Pr | H | 1 | CH₂ | NH | — |
| NHSO₂Me | OH | H | i-Pr | H | 1 | CH₂ | NH | — |
| CONH₂ | OH | H | n-Bu | H | 1 | CO | NH | — |
| CONHMe | OH | H | t-Bu | H | 1 | CO | NH | — |
| CONMe₂ | OH | H | —(CH₂)₅— | | 1 | CO | NH | — |
| COMe | OH | H | —(CH₂)₂O(CH₂)₂— | | 1 | CO | NH | — |
| CO₂Me | OH | H | —(CH₂)₂NH(CH₂)₂— | | 1 | CO | NH | — |
| CO₂Ph | OH | H | i-Pr | H | 1 | CO | NH | — |
| CO₂CH₂Ph | OH | H | c-Pr | H | 1 | CO | NH | — |

TABLE 21

Example of Compounds

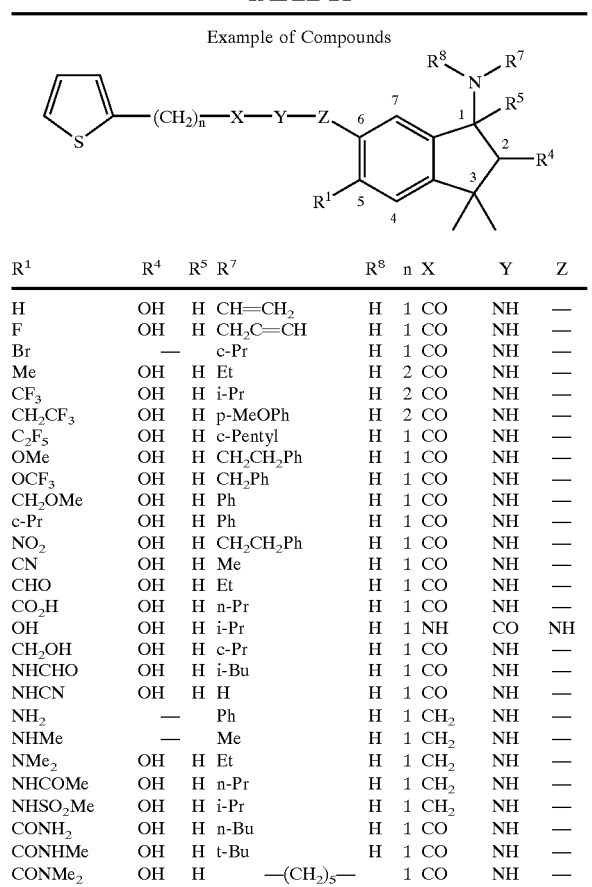

| R¹ | R⁴ | R⁵ | R⁷ | R⁸ | n | X | Y | Z |
|---|---|---|---|---|---|---|---|---|
| H | OH | H | CH=CH₂ | H | 1 | CO | NH | — |
| F | OH | H | CH₂C≡CH | H | 1 | CO | NH | — |
| Br | — | | c-Pr | H | 1 | CO | NH | — |
| Me | OH | H | Et | H | 2 | CO | NH | — |
| CF₃ | OH | H | i-Pr | H | 2 | CO | NH | — |
| CH₂CF₃ | OH | H | p-MeOPh | H | 2 | CO | NH | — |
| C₂F₅ | OH | H | c-Pentyl | H | 1 | CO | NH | — |
| OMe | OH | H | CH₂CH₂Ph | H | 1 | CO | NH | — |
| OCF₃ | OH | H | CH₂Ph | H | 1 | CO | NH | — |
| CH₂OMe | OH | H | Ph | H | 1 | CO | NH | — |
| c-Pr | OH | H | Ph | H | 1 | CO | NH | — |
| NO₂ | OH | H | CH₂CH₂Ph | H | 1 | CO | NH | — |
| CN | OH | H | Me | H | 1 | CO | NH | — |
| CHO | OH | H | Et | H | 1 | CO | NH | — |
| CO₂H | OH | H | n-Pr | H | 1 | CO | NH | — |
| OH | OH | H | i-Pr | H | 1 | NH | CO | NH |
| CH₂OH | OH | H | c-Pr | H | 1 | CO | NH | — |
| NHCHO | OH | H | i-Bu | H | 1 | CO | NH | — |
| NHCN | OH | H | H | H | 1 | CO | NH | — |
| NH₂ | — | | Ph | H | 1 | CH₂ | NH | — |
| NHMe | — | | Me | H | 1 | CH₂ | NH | — |
| NMe₂ | OH | H | Et | H | 1 | CH₂ | NH | — |
| NHCOMe | OH | H | n-Pr | H | 1 | CH₂ | NH | — |
| NHSO₂Me | OH | H | i-Pr | H | 1 | CH₂ | NH | — |
| CONH₂ | OH | H | n-Bu | H | 1 | CO | NH | — |
| CONHMe | OH | H | t-Bu | H | 1 | CO | NH | — |
| CONMe₂ | OH | H | —(CH₂)₅— | | 1 | CO | NH | — |
| COMe | OH | H | —(CH₂)₂O(CH₂)₂— | | 1 | CO | NH | — |
| CO₂Me | OH | H | —(CH₂)₂NH(CH₂)₂— | | 1 | CO | NH | — |
| CO₂Ph | OH | H | i-Pr | H | 1 | CO | NH | — |
| CO₂CH₂Ph | OH | H | c-Pr | H | 1 | CO | NH | — |

TABLE 22

Example of Compounds

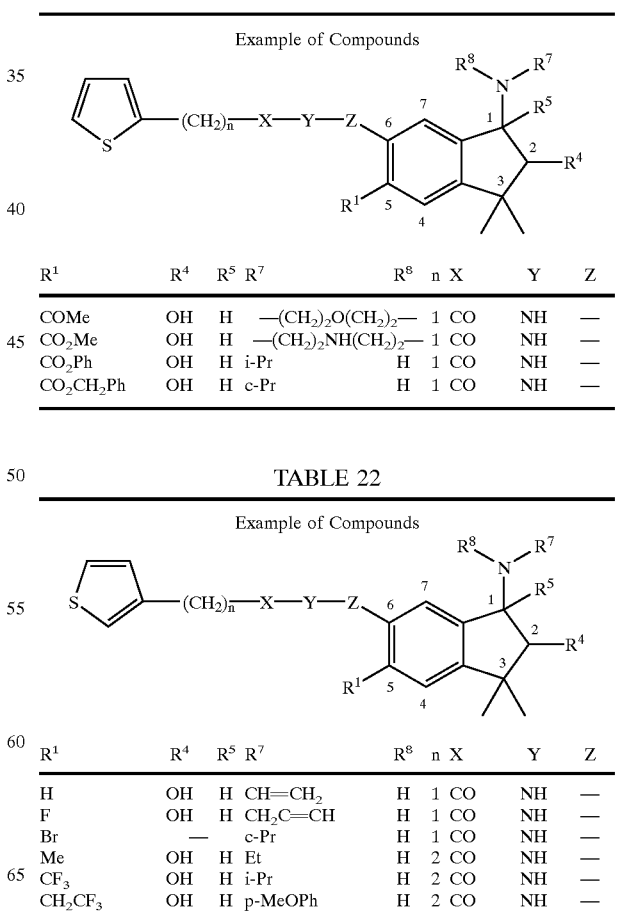

| R¹ | R⁴ | R⁵ | R⁷ | R⁸ | n | X | Y | Z |
|---|---|---|---|---|---|---|---|---|
| H | OH | H | CH=CH₂ | H | 1 | CO | NH | — |
| F | OH | H | CH₂C≡CH | H | 1 | CO | NH | — |
| Br | — | | c-Pr | H | 1 | CO | NH | — |
| Me | OH | H | Et | H | 2 | CO | NH | — |
| CF₃ | OH | H | i-Pr | H | 2 | CO | NH | — |
| CH₂CF₃ | OH | H | p-MeOPh | H | 2 | CO | NH | — |

TABLE 22-continued

Example of Compounds

[Structure: thiophene-(CH$_2$)$_n$-X-Y-Z-indane with R$^1$, R$^4$, R$^5$, R$^7$, R$^8$ substituents]

| R$^1$ | R$^4$ | R$^5$ | R$^7$ | R$^8$ | n | X | Y | Z |
|---|---|---|---|---|---|---|---|---|
| C$_2$F$_5$ | OH | H | c-Pentyl | H | 1 | CO | NH | — |
| OMe | OH | H | CH$_2$CH$_2$Ph | H | 1 | CO | NH | — |
| OCF$_3$ | OH | H | CH$_2$Ph | H | 1 | CO | NH | — |
| CH$_2$OMe | OH | H | Ph | H | 1 | CO | NH | — |
| c-Pr | OH | H | Ph | H | 1 | CO | NH | — |
| NO$_2$ | OH | H | CH$_2$CH$_2$Ph | H | 1 | CO | NH | — |
| CN | OH | H | Me | H | 1 | CO | NH | — |
| CHO | OH | H | Et | H | 1 | CO | NH | — |
| CO$_2$H | OH | H | n-Pr | H | 1 | CO | NH | — |
| OH | OH | H | i-Pr | H | 1 | NH | CO | NH |
| CH$_2$OH | OH | H | c-Pr | H | 1 | CO | NH | — |
| NHCHO | OH | H | i-Bu | H | 1 | CO | NH | — |
| NHCN | OH | H | H | H | 1 | CO | NH | — |
| NH$_2$ | — | | Ph | H | 1 | CH$_2$ | NH | — |
| NHMe | — | | Me | H | 1 | CH$_2$ | NH | — |
| NMe$_2$ | OH | H | Et | H | 1 | CH$_2$ | NH | — |
| NHCOMe | OH | H | n-Pr | H | 1 | CH$_2$ | NH | — |
| NHSO$_2$Me | OH | H | i-Pr | H | 1 | CH$_2$ | NH | — |
| CONH$_2$ | OH | H | n-Bu | H | 1 | CO | NH | — |
| CONHMe | OH | H | t-Bu | H | 1 | CO | NH | — |
| CONMe$_2$ | OH | H | —(CH$_2$)$_5$— | | 1 | CO | NH | — |
| COMe | OH | H | —(CH$_2$)$_2$O(CH$_2$)$_2$— | | 1 | CO | NH | — |
| CO$_2$Me | OH | H | —(CH$_2$)$_2$NH(CH$_2$)$_2$— | | 1 | CO | NH | — |
| CO$_2$Ph | OH | H | i-Pr | H | 1 | CO | NH | — |
| CO$_2$CH$_2$Ph | OH | H | c-Pr | H | 1 | CO | NH | — |

TABLE 23

Example of Compounds

[Structure: pyrrole-(CH$_2$)$_n$-X-Y-Z-indane with R$^1$, R$^4$, R$^5$, R$^7$, R$^8$ substituents]

| R$^1$ | R$^4$ | R$^5$ | R$^7$ | R$^8$ | n | X | Y | Z |
|---|---|---|---|---|---|---|---|---|
| H | OH | H | CH=CH$_2$ | H | 1 | CO | NH | — |
| F | OH | H | CH$_2$C≡CH | H | 1 | CO | NH | — |
| Br | — | | c-Pr | H | 1 | CO | NH | — |
| Me | OH | H | Et | H | 2 | CO | NH | — |
| CF$_3$ | OH | H | i-Pr | H | 2 | CO | NH | — |
| CH$_2$CF$_3$ | OH | H | p-MeOPh | H | 2 | CO | NH | — |
| C$_2$F$_5$ | OH | H | c-Pentyl | H | 1 | CO | NH | — |
| OMe | OH | H | CH$_2$CH$_2$Ph | H | 1 | CO | NH | — |
| OCF$_3$ | OH | H | CH$_2$Ph | H | 1 | CO | NH | — |
| CH$_2$OMe | OH | H | Ph | H | 1 | CO | NH | — |
| c-Pr | OH | H | Ph | H | 1 | CO | NH | — |
| NO$_2$ | OH | H | CH$_2$CH$_2$Ph | H | 1 | CO | NH | — |
| CN | OH | H | Me | H | 1 | CO | NH | — |
| CHO | OH | H | Et | H | 1 | CO | NH | — |
| CO$_2$H | OH | H | n-Pr | H | 1 | CO | NH | — |
| OH | OH | H | i-Pr | H | 1 | NH | CO | NH |
| CH$_2$OH | OH | H | c-Pr | H | 1 | CO | NH | — |
| NHCHO | OH | H | i-Bu | H | 1 | CO | NH | — |
| NHCN | OH | H | H | H | 1 | CO | NH | — |
| NH$_2$ | — | | Ph | H | 1 | CH$_2$ | NH | — |
| NHMe | — | | Me | H | 1 | CH$_2$ | NH | — |
| NMe$_2$ | OH | H | Et | H | 1 | CH$_2$ | NH | — |

TABLE 23-continued

Example of Compounds

[Structure: pyrrole-(CH$_2$)$_n$-X-Y-Z-indane with R$^1$, R$^4$, R$^5$, R$^7$, R$^8$ substituents]

| R$^1$ | R$^4$ | R$^5$ | R$^7$ | R$^8$ | n | X | Y | Z |
|---|---|---|---|---|---|---|---|---|
| NHCOMe | OH | H | n-Pr | H | 1 | CH$_2$ | NH | — |
| NHSO$_2$Me | OH | H | i-Pr | H | 1 | CH$_2$ | NH | — |
| CONH$_2$ | OH | H | n-Bu | H | 1 | CO | NH | — |
| CONHMe | OH | H | t-Bu | H | 1 | CO | NH | — |
| CONMe$_2$ | OH | H | —(CH$_2$)$_5$— | | 1 | CO | NH | — |
| COMe | OH | H | —(CH$_2$)$_2$O(CH$_2$)$_2$— | | 1 | CO | NH | — |
| CO$_2$Me | OH | H | —(CH$_2$)$_2$NH(CH$_2$)$_2$— | | 1 | CO | NH | — |
| CO$_2$Ph | OH | H | i-Pr | H | 1 | CO | NH | — |
| CO$_2$CH$_2$Ph | OH | H | c-Pr | H | 1 | CO | NH | — |

TABLE 24

Example of Compounds

[Structure: pyrrol-3-yl-(CH$_2$)$_n$-X-Y-Z-indane with R$^1$, R$^4$, R$^5$, R$^7$, R$^8$ substituents]

| R$^1$ | R$^4$ | R$^5$ | R$^7$ | R$^8$ | n | X | Y | Z |
|---|---|---|---|---|---|---|---|---|
| H | OH | H | CH=CH$_2$ | H | 1 | CO | NH | — |
| F | OH | H | CH$_2$C≡CH | H | 1 | CO | NH | — |
| Br | — | | c-Pr | H | 1 | CO | NH | — |
| Me | OH | H | Et | H | 2 | CO | NH | — |
| CF$_3$ | OH | H | i-Pr | H | 2 | CO | NH | — |
| CH$_2$CF$_3$ | OH | H | p-MeOPh | H | 2 | CO | NH | — |
| C$_2$F$_5$ | OH | H | c-Pentyl | H | 1 | CO | NH | — |
| OMe | OH | H | CH$_2$CH$_2$Ph | H | 1 | CO | NH | — |
| OCF$_3$ | OH | H | CH$_2$Ph | H | 1 | CO | NH | — |
| CH$_2$OMe | OH | H | Ph | H | 1 | CO | NH | — |
| c-Pr | OH | H | Ph | H | 1 | CO | NH | — |
| NO$_2$ | OH | H | CH$_2$CH$_2$Ph | H | 1 | CO | NH | — |
| CN | OH | H | Me | H | 1 | CO | NH | — |
| CHO | OH | H | Et | H | 1 | CO | NH | — |
| CO$_2$H | OH | H | n-Pr | H | 1 | CO | NH | — |
| OH | OH | H | i-Pr | H | 1 | NH | CO | NH |
| CH$_2$OH | OH | H | c-Pr | H | 1 | CO | NH | — |
| NHCHO | OH | H | i-Bu | H | 1 | CO | NH | — |
| NHCN | OH | H | H | H | 1 | CO | NH | — |
| NH$_2$ | — | | Ph | H | 1 | CH$_2$ | NH | — |
| NHMe | — | | Me | H | 1 | CH$_2$ | NH | — |
| NMe$_2$ | OH | H | Et | H | 1 | CH$_2$ | NH | — |
| NHCOMe | OH | H | n-Pr | H | 1 | CH$_2$ | NH | — |
| NHSO$_2$Me | OH | H | i-Pr | H | 1 | CH$_2$ | NH | — |
| CONH$_2$ | OH | H | n-Bu | H | 1 | CO | NH | — |
| CONHMe | OH | H | t-Bu | H | 1 | CO | NH | — |
| CONMe$_2$ | OH | H | —(CH$_2$)$_5$— | | 1 | CO | NH | — |
| COMe | OH | H | —(CH$_2$)$_2$O(CH$_2$)$_2$— | | 1 | CO | NH | — |
| CO$_2$Me | OH | H | —(CH$_2$)$_2$NH(CH$_2$)$_2$— | | 1 | CO | NH | — |
| CO$_2$Ph | OH | H | i-Pr | H | 1 | CO | NH | — |
| CO$_2$CH$_2$Ph | OH | H | c-Pr | H | 1 | CO | NH | — |

TABLE 25

Example of Compounds

[Structure: 1H-indol-2-yl-(CH₂)ₙ-X-Y-Z linked to indane with R⁸N(R⁷), R⁵ at position 1, R⁴ at position 2, gem-dimethyl at position 3, R¹ at position 5, Z at position 6]

| R¹ | R⁴ | R⁵ | R⁷ | R⁸ | n | X | Y | Z |
|---|---|---|---|---|---|---|---|---|
| H | OH | H | CH=CH₂ | H | 1 | CO | NH | — |
| F | OH | H | CH₂C=CH | H | 1 | CO | NH | — |
| Br | — | H | c-Pr | H | 1 | CO | NH | — |
| Me | OH | H | Et | H | 2 | CO | NH | — |
| CF₃ | OH | H | i-Pr | H | 2 | CO | NH | — |
| CH₂CF₃ | OH | H | p-MeOPh | H | 2 | CO | NH | — |
| C₂F₅ | OH | H | c-Pentyl | H | 1 | CO | NH | — |
| OMe | OH | H | CH₂CH₂Ph | H | 1 | CO | NH | — |
| OCF₃ | OH | H | CH₂Ph | H | 1 | CO | NH | — |
| CH₂OMe | OH | H | Ph | H | 1 | CO | NH | — |
| c-Pr | OH | H | Ph | H | 1 | CO | NH | — |
| NO₂ | OH | H | CH₂CH₂Ph | H | 1 | CO | NH | — |
| CN | OH | H | Me | H | 1 | CO | NH | — |
| CHO | OH | H | Et | H | 1 | CO | NH | — |
| CO₂H | OH | H | n-Pr | H | 1 | CO | NH | — |
| OH | OH | H | i-Pr | H | 1 | NH | CO | NH |
| CH₂OH | OH | H | c-Pr | H | 1 | CO | NH | — |
| NHCHO | OH | H | i-Bu | H | 1 | CO | NH | — |
| NHCN | OH | H | H | H | 1 | CO | NH | — |
| NH₂ | — | | Ph | H | 1 | CH₂ | NH | — |
| NHMe | — | | Me | H | 1 | CH₂ | NH | — |
| NMe₂ | OH | H | Et | H | 1 | CH₂ | NH | — |
| NHCOMe | OH | H | n-Pr | H | 1 | CH₂ | NH | — |
| NHSO₂Me | OH | H | i-Pr | H | 1 | CH₂ | NH | — |
| CONH₂ | OH | H | n-Bu | H | 1 | CO | NH | — |
| CONHMe | OH | H | t-Bu | H | 1 | CO | NH | — |
| CONMe₂ | OH | H | —(CH₂)₅— | | 1 | CO | NH | — |
| COMe | OH | H | —(CH₂)₂O(CH₂)₂— | | 1 | CO | NH | — |
| CO₂Me | OH | H | —(CH₂)₂NH(CH₂)₂— | | 1 | CO | NH | — |
| CO₂Ph | OH | H | i-Pr | H | 1 | CO | NH | — |
| CO₂CH₂Ph | OH | H | c-Pr | H | 1 | CO | NH | — |

TABLE 26

Example of Compounds

[Structure: pyrimidin-4-yl-(CH₂)ₙ-X-Y-Z linked to indane with R⁸N(R⁷), R⁵ at position 1, R⁴ at position 2, gem-dimethyl at position 3, R¹ at position 5]

| R¹ | R⁴ | R⁵ | R⁷ | R⁸ | n | X | Y | Z |
|---|---|---|---|---|---|---|---|---|
| H | OH | H | CH=CH₂ | H | 1 | CO | NH | — |
| F | OH | H | CH₂C=CH | H | 1 | CO | NH | — |
| Br | — | H | c-Pr | H | 1 | CO | NH | — |
| Me | OH | H | Et | H | 2 | CO | NH | — |
| CF₃ | OH | H | i-Pr | H | 2 | CO | NH | — |
| CH₂CF₃ | OH | H | p-MeOPh | H | 2 | CO | NH | — |
| C₂F₅ | OH | H | c-Pentyl | H | 1 | CO | NH | — |
| OMe | OH | H | CH₂CH₂Ph | H | 1 | CO | NH | — |
| OCF₃ | OH | H | CH₂Ph | H | 1 | CO | NH | — |
| CH₂OMe | OH | H | Ph | H | 1 | CO | NH | — |
| c-Pr | OH | H | Ph | H | 1 | CO | NH | — |
| NO₂ | OH | H | CH₂CH₂Ph | H | 1 | CO | NH | — |
| CN | OH | H | Me | H | 1 | CO | NH | — |
| CHO | OH | H | Et | H | 1 | CO | NH | — |
| CO₂H | OH | H | n-Pr | H | 1 | CO | NH | — |
| OH | OH | H | i-Pr | H | 1 | NH | CO | NH |
| CH₂OH | OH | H | c-Pr | H | 1 | CO | NH | — |
| NHCHO | OH | H | i-Bu | H | 1 | CO | NH | — |
| NHCN | OH | H | H | H | 1 | CO | NH | — |
| NH₂ | — | | Ph | H | 1 | CH₂ | NH | — |
| NHMe | — | | Me | H | 1 | CH₂ | NH | — |
| NMe₂ | OH | H | Et | H | 1 | CH₂ | NH | — |
| NHCOMe | OH | H | n-Pr | H | 1 | CH₂ | NH | — |
| NHSO₂Me | OH | H | i-Pr | H | 1 | CH₂ | NH | — |
| CONH₂ | OH | H | n-Bu | H | 1 | CO | NH | — |
| CONHMe | OH | H | t-Bu | H | 1 | CO | NH | — |
| CONMe₂ | OH | H | —(CH₂)₅— | | 1 | CO | NH | — |
| COMe | OH | H | —(CH₂)₂O(CH₂)₂— | | 1 | CO | NH | — |
| CO₂Me | OH | H | —(CH₂)₂NH(CH₂)₂— | | 1 | CO | NH | — |
| CO₂Ph | OH | H | i-Pr | H | 1 | CO | NH | — |
| CO₂CH₂Ph | OH | H | c-Pr | H | 1 | CO | NH | — |

TABLE 27

Example of Compounds

[Structure: phenyl-(CH₂)ₙ-X-Y-Z linked to indane, R⁸N(R⁷), R⁵ at 1, R⁴ at 2, R²/R³ at 3, NO₂ at 5]

| R² | R³ | R⁴ | R⁵ | R⁷ | R⁸ | n | X | Y | Z |
|---|---|---|---|---|---|---|---|---|---|
| Me | Me | OH | H | H | H | 4 | CO | NH | — |
| Me | Me | — | | Ph | H | 3 | CO | NH | — |
| Me | Me | OH | H | Me | H | 1 | CO | NH | — |
| Me | Me | OH | H | Me | Me | 1 | CO | NH | — |
| Me | Me | OH | H | Et | H | 2 | CO | NH | — |
| Me | Me | OH | H | Et | Et | 1 | CO | NH | — |
| Me | Me | OH | H | n-Pr | H | 1 | CO | NH | — |
| Me | Me | OH | H | n-Pr | n-Pr | 1 | CH₂ | NH | — |
| Me | Me | — | | i-Pr | H | 1 | CO | NH | — |
| Me | Me | OH | H | i-Pr | i-Pr | 1 | CO | NH | — |
| Me | Me | OH | H | c-Pr | H | 1 | CO | NH | — |
| Et | Et | OH | H | n-Bu | H | 1 | CO | NH | — |
| Me | Me | OH | H | t-Bu | H | 2 | CO | NH | — |
| Me | Me | OH | H | CH=CH₂ | H | 1 | CO | NH | CH₂ |
| Me | Me | OH | H | CH₂C=CH | H | 1 | CO | NH | — |
| Me | Me | OH | H | n-Pentyl | H | 1 | CO | NH | — |
| Me | Me | OH | H | c-Pentyl | H | 1 | CO | NH | — |
| Me | Me | OH | H | n-Hexyl | H | 1 | CO | NH | — |
| Me | Me | OH | H | p-MeOPh | H | 1 | CO | NH | — |
| Me | Me | OH | H | i-Pr | H | 2 | CO | NH | — |
| Me | Me | OH | H | i-Pr | Me | 1 | CO | NH | — |
| Me | Me | OH | H | Et | Et | 0 | CO | NH | — |
| Me | Me | OH | H | CH₂Ph | H | 1 | CO | NH | — |
| Me | Me | OH | H | CH₂CH₂Ph | H | 1 | CO | NH | — |
| Me | Me | OH | H | Ph | H | 1 | NH | CO | NH |
| Me | Me | OH | H | Ph | H | 1 | CO | NH | — |
| Me | Me | OH | H | —(CH₂)₂O(CH₂)₂— | | 1 | CO | NH | — |
| Me | Me | OH | H | —(CH₂)₂NH(CH₂)₂— | | 1 | CO | NH | — |
| n-Pr | n-Pr | OH | H | Ph | H | 1 | CO | NH | — |
| Me | Me | OH | H | Ph | H | 1 | CO | NH | — |

TABLE 28

Example of Compounds

Phenyl-(CH₂)ₙ-X-Y-Z-[indane with positions 1-7, N(R⁷)(R⁸) and R⁵ at position 1, R⁴ at position 2, R²/R³ at position 3, R¹ at position 5, Z at position 6]

| R¹ | R² | R³ | R⁴ | R⁵ | R⁷ | R⁸ | n | X | Y | Z |
|---|---|---|---|---|---|---|---|---|---|---|
| CN | Me | Me | OH | H | H | H | 1 | CO | NH | CH₂ |
| NO₂ | Me | Me | — | —(CH₂)₄— | | | 1 | CO | NH | CH₂ |
| NO₂ | Me | Me | OH | H | Me | H | 1 | CO | NH | CH₂ |
| NO₂ | CF₃ | CF₃ | OH | H | Me | Me | 2 | CO | NH | CH₂ |
| NO₂ | Me | Me | OH | H | Et | H | 1 | CO | NH | CH₂ |
| NO₂ | Me | Me | OH | H | Et | Et | 1 | CO | NH | CH₂ |
| NO₂ | Me | Me | OH | H | n-Pr | H | 1 | CO | NH | CH₂ |
| NO₂ | Me | Me | OH | H | i-Pr | H | 1 | CO | NH | CH₂ |
| NO₂ | Me | Me | — | Me | Me | | 1 | CH₂ | NH | — |
| NO₂ | Me | Me | OH | H | —(CH₂)₄— | | 1 | CH₂ | NH | — |
| NO₂ | Me | Me | OH | H | Me | H | 1 | CH₂ | NH | — |
| NO₂ | Me | Me | OH | H | Et | H | 1 | CH₂ | NH | — |
| NO₂ | Me | Me | OH | H | n-Pr | H | 1 | CH₂ | NH | — |
| NO₂ | Me | Me | OH | H | i-Pr | H | 1 | CH₂ | NH | — |
| CN | CF₃ | CF₃ | OH | H | Et | Et | 1 | CH₂ | NH | CH₂ |
| CN | Me | Me | OH | H | —(CH₂)₄— | | 1 | CH₂ | NH | CH₂ |
| CN | Me | Me | OH | H | Me | H | 1 | CH₂ | NH | CH₂ |
| CN | Me | Me | OH | H | Et | H | 2 | CH₂ | NH | CH₂ |
| CN | Me | Me | OH | H | n-Pr | H | 2 | CH₂ | NH | CH₂ |
| CN | Me | Me | OH | H | i-Pr | H | 2 | CH₂ | NH | CH₂ |
| NO₂ | Me | Me | OH | H | Me | Me | 1 | SO₂ | NH | — |
| NO₂ | Me | Me | OH | H | —(CH₂)₄— | | 1 | SO₂ | NH | — |
| NO₂ | Me | Me | OH | H | Me | H | 1 | SO₂ | NH | — |
| NO₂ | Me | Me | OH | H | Et | H | 1 | SO₂ | NH | — |
| NO₂ | Me | Me | OH | H | n-Pr | H | 1 | SO₂ | NH | — |
| NO₂ | Me | Me | OH | H | i-Pr | H | 1 | SO₂ | NH | — |
| NO₂ | Me | Me | OH | H | —(CH₂)₄— | | 0 | NH | CO | NH |
| NO₂ | Me | Me | OH | H | Me | H | 1 | NH | CO | NH |
| NO₂ | Me | Me | OH | H | Et | H | 1 | NH | CO | NH |
| NO₂ | Me | Me | OH | H | n-Pr | H | 1 | NH | CO | NH |
| NO₂ | Me | Me | OH | H | i-Pr | H | 1 | NH | CO | NH |

TABLE 29

Example of Compounds

Phenyl-(CH₂)ₙ-X-Y-Z-[indane with positions 1-7, N(R⁷)(R⁸) and R⁵ at position 1, R⁴ at position 2, R²/R³ at position 3, R¹ at position 5, Z at position 6]

| R¹ | R² | R³ | R⁴ | R⁵ | R⁷ | R⁸ | n | X | Y | Z |
|---|---|---|---|---|---|---|---|---|---|---|
| CN | Me | Me | OH | H | Et | H | 2 | CO | NH | CH₂ |
| CN | Me | Me | — | —(CH₂)₄— | | | 2 | CO | NH | CH₂ |
| CN | Me | Me | OH | H | Me | H | 2 | CO | NH | CH₂ |
| CN | Me | Me | OH | H | Me | Me | 2 | CO | NH | CH₂ |
| CN | Me | Me | OH | H | Et | H | 3 | CO | NH | CH₂ |
| CN | Me | Me | OH | H | Et | Et | 2 | CO | NH | CH₂ |
| CN | Me | Me | OH | H | n-Pr | H | 2 | CO | NH | CH₂ |
| H | Me | Me | OH | H | i-Pr | H | 2 | CO | NH | CH₂ |
| NO₂ | CF₃ | CF₃ | — | Me | Me | | 2 | CH₂ | NH | — |
| NO₂ | Me | Me | OH | H | —(CH₂)₄— | | 2 | CH₂ | NH | — |
| NO₂ | Me | Me | OH | H | Me | H | 2 | CH₂ | NH | — |
| NO₂ | Me | Me | OH | H | Et | H | 2 | CH₂ | NH | — |
| NO₂ | Me | Me | OH | H | n-Pr | H | 2 | CH₂ | NH | — |
| NO₂ | Me | Me | OH | H | i-Pr | H | 2 | CH₂ | NH | — |
| NO₂ | CF₃ | CF₃ | OH | H | Et | Et | 2 | CH₂ | NH | CH₂ |
| NO₂ | Me | Me | OH | H | —(CH₂)₄— | | 2 | CH₂ | NH | CH₂ |
| NO₂ | Me | Me | OH | H | Me | H | 2 | CH₂ | NH | CH₂ |
| NO₂ | Me | Me | OH | H | Et | H | 1 | CH₂ | NH | CH₂ |
| NO₂ | Me | Me | OH | H | n-Pr | H | 1 | CH₂ | NH | CH₂ |
| NO₂ | Me | Me | OH | H | i-Pr | H | 1 | CH₂ | NH | CH₂ |
| NO₂ | Me | Me | OH | H | Me | Me | 2 | SO₂ | NH | — |
| NO₂ | Me | Me | OH | H | —(CH₂)₄— | | 2 | SO₂ | NH | — |
| NO₂ | Me | Me | OH | H | Me | H | 2 | SO₂ | NH | — |
| NO₂ | Me | Me | OH | H | Et | H | 2 | SO₂ | NH | — |
| NO₂ | Me | Me | OH | H | n-Pr | H | 2 | SO₂ | NH | — |
| NO₂ | Me | Me | OH | H | i-Pr | H | 2 | SO₂ | NH | — |
| NO₂ | Me | Me | OH | H | —(CH₂)₄— | | 2 | NH | CO | NH |
| NO₂ | Me | Me | OH | H | Me | H | 2 | NH | CO | NH |
| NO₂ | Me | Me | OH | H | Et | H | 2 | NH | CO | NH |
| NO₂ | Me | Me | OH | H | n-Pr | H | 2 | NH | CO | NH |
| NO₂ | Me | Me | OH | H | i-Pr | H | 2 | NH | CO | NH |

TABLE 30

Example of Compounds

Phenyl-(CH₂)ₙ-X-Y-Z-[indane with positions 1-7, N(R⁷)(R⁸) and R⁵ at position 1, R⁴ at position 2, R²/R³ at position 3, R¹ at position 5, Z at position 6]

| R¹ | R² | R³ | R⁴ | R⁵ | R⁷ | R⁸ | n | X | Y | Z |
|---|---|---|---|---|---|---|---|---|---|---|
| NO₂ | CF₃ | CF₃ | OH | H | i-Pr | H | 3 | CO | NH | CH₂ |
| NO₂ | Me | Me | — | —(CH₂)₄— | | | 3 | CO | NH | CH₂ |
| NO₂ | Me | Me | OH | H | Me | H | 3 | CO | NH | CH₂ |
| CO₂Me | Me | Me | OH | H | Me | Me | 3 | CO | NH | CH₂ |
| NO₂ | Me | Me | OH | H | Et | H | 3 | CO | NH | CH₂ |
| CO₂Me | Me | Me | OH | H | Et | Et | 3 | CO | NH | CH₂ |
| NO₂ | Me | Me | OH | H | n-Pr | H | 3 | CO | NH | CH₂ |
| NO₂ | Me | Me | OH | H | i-Pr | H | 3 | CO | NH | CH₂ |
| CO₂Me | Me | Me | — | Me | Me | | 3 | CH₂ | NH | — |
| NO₂ | Me | Me | OH | H | —(CH₂)₄— | | 3 | CH₂ | NH | — |
| NO₂ | Me | Me | OH | H | Me | H | 3 | CH₂ | NH | — |
| NO₂ | Me | Me | OH | H | Et | H | 3 | CH₂ | NH | — |
| NO₂ | Me | Me | OH | H | n-Pr | H | 3 | CH₂ | NH | — |
| NO₂ | Me | Me | OH | H | i-Pr | H | 3 | CH₂ | NH | — |
| CO₂Me | Me | Me | OH | H | Et | Et | 4 | CH₂ | NH | CH₂ |
| NO₂ | Me | Me | OH | H | —(CH₂)₄— | | 3 | CH₂ | NH | CH₂ |
| NO₂ | Me | Me | OH | H | Me | H | 3 | CH₂ | NH | CH₂ |
| NO₂ | Me | Me | OH | H | Et | H | 3 | CH₂ | NH | CH₂ |
| NO₂ | Me | Me | OH | H | n-Pr | H | 4 | CH₂ | NH | CH₂ |
| NO₂ | Me | Me | OH | H | i-Pr | H | 3 | CH₂ | NH | CH₂ |
| NO₂ | Me | Me | OH | H | Me | Me | 3 | SO₂ | NH | — |
| CO₂Me | Me | Me | OH | H | —(CH₂)₄— | | 3 | SO₂ | NH | — |
| NO₂ | Me | Me | OH | H | Me | H | 3 | SO₂ | NH | — |
| NO₂ | Me | Me | OH | H | Et | H | 3 | SO₂ | NH | — |
| NO₂ | Me | Me | OH | H | n-Pr | H | 4 | SO₂ | NH | — |
| NO₂ | Me | Me | OH | H | i-Pr | H | 3 | SO₂ | NH | — |
| NO₂ | Me | Me | OH | H | —(CH₂)₄— | | 3 | NH | CO | NH |
| NO₂ | Me | Me | OH | H | Me | H | 3 | NH | CO | NH |
| NO₂ | Me | Me | OH | H | Et | H | 3 | NH | CO | NH |
| CO₂Me | Me | Me | OH | H | n-Pr | H | 4 | NH | CO | NH |
| NO₂ | Me | Me | OH | H | i-Pr | H | 3 | NH | CO | NH |

TABLE 31

Example of Compounds

[Structure: Ph-(CH₂)ₙ-X-Y-Z-[indane with positions 1-7, R⁵ at 1, R⁴ at 2, Me,Me at 3, NO₂ at 5, connected at 6; NR⁷R⁸ at 1]]

| R⁴ | R⁵ | R⁷ | R⁸ | n | X | Y | Z |
|---|---|---|---|---|---|---|---|
| OH | H | c-Pr | H | 1 | CO | NH | — |
| — | | Ph | H | 0 | CO | NH | — |
| OH | H | Me | H | 2 | CO | NH | — |
| OH | H | Me | Me | 2 | CO | NH | — |
| OH | H | Et | H | 2 | CO | NH | — |
| OH | H | Et | Et | 2 | CO | NH | — |
| OH | H | n-Pr | H | 2 | CO | NH | — |
| OH | H | n-Pr | n-Pr | 2 | CO | NH | — |
| — | | i-Pr | H | 2 | CO | NH | — |
| OH | H | i-Pr | i-Pr | 2 | CO | NH | — |
| OH | H | c-Pr | H | 2 | CO | NH | — |
| OH | H | n-Bu | H | 2 | CO | NH | — |
| OH | H | t-Bu | H | 2 | CO | NH | — |
| OH | H | CH=CH₂ | H | 2 | CO | NH | — |
| OH | H | CH₂C≡CH | H | 2 | CO | NH | — |
| OH | H | n-Pentyl | H | 2 | CO | NH | — |
| OH | H | c-Pentyl | H | 3 | CO | NH | — |
| OH | H | n-Hexyl | H | 3 | CO | NH | — |
| OH | H | p-MeOPh | H | 3 | CO | NH | — |
| OH | H | i-Pr | H | 2 | CO | NH | — |
| OH | H | i-Pr | Me | 2 | CO | NH | — |
| OH | H | Et | Et | 4 | CO | NH | — |
| OH | H | Ph | H | 2 | CO | NH | — |
| OH | H | CH₂Ph | H | 2 | CO | NH | — |
| OH | H | CH₂CH₂Ph | H | 2 | CO | NH | — |
| OH | H | Ph | H | 3 | CO | NH | — |
| OH | H | Ph | H | 3 | CO | NH | — |
| OH | H | —(CH₂)₂O(CH₂)₂— | | 2 | CO | NH | — |
| OH | H | —(CH₂)₂NH(CH₂)₂— | | 2 | CO | NH | — |
| OH | H | Ph | H | 2 | CO | NH | — |
| OH | H | Ph | H | 3 | CO | NH | — |

TABLE 32

Example of Compounds

[Structure: (R⁹)ₘ-Ph-CH₂-C(=O)-NH-[indane with positions 1-7, R⁵ at 1, R⁴ at 2, Me,Me at 3, NO₂ at 5, connected at 6; NR⁷R⁸ at 1]]

| R⁴ | R⁵ | R⁷ | R⁸ | R⁹ | m |
|---|---|---|---|---|---|
| OH | H | c-Pr | H | p-OEt | 1 |
| OH | H | —(CH₂)₄— | | p-OMe | 1 |
| OH | H | Me | Me | p-OMe | 1 |
| OH | H | Me | Me | m,p-(OMe)₂ | 2 |
| OH | H | Et | H | p-OMe | 1 |
| OH | H | Et | Et | p-OMe | 1 |
| OH | H | c-Pr | H | p-OMe | 1 |
| OH | H | i-Pr | H | p-OMe | 1 |
| OH | H | c-Pr | H | p-OMe | 2 |
| OH | H | —(CH₂)₄— | | m,p-(OMe)₂ | 2 |
| OH | H | Me | H | p-F | 1 |
| OH | H | Et | H | m,p-(OMe)₂ | 2 |
| OH | H | n-Pr | H | p-NHMe | 1 |
| OH | H | i-Pr | H | m,p-(OMe)₂ | 2 |
| OH | H | c-Pr | H | m,p-(OMe)₂ | 2 |
| OH | H | —(CH₂)₄— | | m-OMe | 1 |

TABLE 32-continued

Example of Compounds

| R⁴ | R⁵ | R⁷ | R⁸ | R⁹ | m |
|---|---|---|---|---|---|
| OH | H | c-Pr | H | m-OMe | 1 |
| OH | H | Et | H | m-OMe | 1 |
| OH | H | c-Pr | H | o-OMe | 1 |
| OH | H | i-Pr | H | m-OMe | 1 |
| OH | H | c-Pr | H | p-NO₂ | 1 |
| OH | H | —(CH₂)₄— | | p-CN | 1 |
| OH | H | Me | H | p-NMe₂ | 1 |
| — | | Et | H | p-Me | 1 |
| OH | H | c-Pr | H | p-OH | 1 |
| OH | H | i-Pr | H | p-Cl | 1 |
| OH | H | —(CH₂)₄— | | p-Ac | 1 |
| OH | H | Me | H | p-CO₂Me | 1 |
| OH | H | Et | H | p-NHAc | 1 |
| OH | H | c-Pr | H | p-NHAc | 1 |
| OH | H | i-Pr | H | p-NHAC | 1 |

TABLE 33

Example of Compounds

[Structure: (R⁹)ₘ-Ph-CH₂-X-Y-Z-[indane with positions 1-7, R⁵ at 1, R⁴ at 2, Me,Me at 3, NO₂ at 5, connected at 6; NR⁷R⁸ at 1]]

| R⁴ | R⁵ | R⁷ | R⁸ | R⁹ | m | X | Y | Z |
|---|---|---|---|---|---|---|---|---|
| OH | H | Et | H | p-OMe | 1 | CO | NMe | — |
| OH | H | c-Pr | H | m,p-OCH₂O— | 1 | CO | NH | — |
| OH | H | Me | H | p-OMe | 1 | CO | NH | CH₂ |
| OH | H | Me | Me | p-F | 1 | CO | NH | CH₂ |
| OH | H | Et | H | p-OMe | 1 | CO | NH | CH₂ |
| OH | H | Et | Et | p-Me | 1 | CO | NH | CH₂ |
| OH | H | n-Pr | H | m,p-(OMe)₂ | 2 | CO | NH | CH₂ |
| OH | H | i-Pr | H | p-OMe | 1 | CO | NH | CH₂ |
| — | | Me | Me | p-Br | 1 | CH₂ | NH | — |
| OH | H | —(CH₂)₄— | | m,p-(OMe)₂ | 2 | CH₂ | NH | — |
| OH | H | Me | H | m,p-Me₃ | 2 | CH₂ | NH | — |
| OH | H | Et | H | m,p-(OMe)₂ | 2 | CH₂ | NH | — |
| OH | H | n-Pr | H | p-NMe₂ | 1 | CH₂ | NH | — |
| OH | H | c-Pr | H | p-OMe | 1 | CH₂ | NH | — |
| OH | H | Et | Et | p-NHMe | 1 | CH₂ | NH | CH₂ |
| OH | H | —(CH₂)₄— | | m-OMe | 1 | CH₂ | NH | CH₂ |
| OH | H | Me | H | p-NH₂ | 1 | CH₂ | NH | CH₂ |
| OH | H | Et | H | p-NHCONH₂ | 1 | CH₂ | NH | CH₂ |
| OH | H | n-Pr | H | p-CN | 1 | CH₂ | NH | CH₂ |
| OH | H | i-Pr | H | p-NO₂ | 1 | CH₂ | NH | CH₂ |
| OH | H | Me | Me | p-Ac | 1 | SO₂ | NH | — |
| OH | H | —(CH₂)₄— | | p-CO₂Me | 1 | SO₂ | NH | — |
| OH | H | Me | H | p-CONH₂ | 1 | SO₂ | NH | — |
| OH | H | Et | H | p-COPh | 1 | SO₂ | NH | — |
| OH | H | n-Pr | H | p-NHAc | 1 | SO₂ | NH | — |
| OH | H | i-Pr | H | p-CF₃ | 1 | SO₂ | NH | — |
| OH | H | —(CH₂)₄— | | p-OMe | 1 | NH | CO | NH |
| OH | H | Me | H | p-OMe | 1 | NH | CO | NH |
| OH | H | Et | H | m,p-(OMe)₂ | 2 | NH | CO | NH |
| OH | H | n-Pr | H | p-OCF₃ | 1 | NH | CO | NH |
| OH | H | i-Pr | H | p-OMe | 1 | NH | CO | NH |

TABLE 34

Example of Compounds

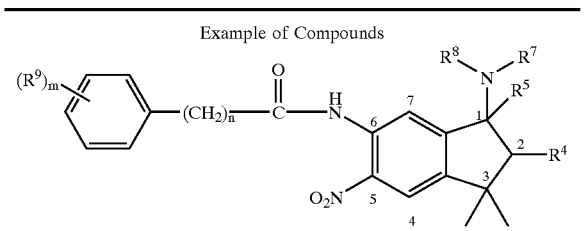

| R⁴ | R⁵ | R⁷ | R⁸ | R⁹ | m | n |
|---|---|---|---|---|---|---|
| OH | H | H | H | p-Cl | 1 | 2 |
| — | | —(CH₂)₄— | | p-OMe | 1 | 2 |
| OH | H | Me | H | p-OMe | 1 | 2 |
| OH | H | i-Pr | H | m,p-(OMe)₂ | 2 | 1 |
| OH | H | Et | H | p-OMe | 1 | 2 |
| OH | H | c-Pr | H | p-OMe | 1 | 2 |
| OH | H | —(CH₂)₄— | | p-OMe | 1 | 2 |
| OH | H | i-Pr | H | p-OMe | 1 | 2 |
| — | | Me | Me | p-OMe | 1 | 2 |
| OH | H | —(CH₂)₄— | | m,p-(OMe)₂ | 2 | 2 |
| OH | H | —(CH₂)₄— | | p-F | 1 | 1 |
| OH | H | Et | H | m,p-(OMe)₂ | 2 | 2 |
| OH | H | n-Pr | H | p-NHMe | 1 | 2 |
| OH | H | i-Pr | H | m,p-(OMe)₂ | 2 | 2 |
| OH | H | c-Pr | H | m,p-(OMe)₂ | 2 | 2 |
| OH | H | —(CH₂)₄— | | m-OMe | 1 | 2 |
| OH | H | Me | H | m-OMe | 1 | 3 |
| OH | H | Et | H | m-OMe | 1 | 2 |
| OH | H | n-Pr | H | o-OMe | 1 | 4 |
| OH | H | i-Pr | H | m-OMe | 1 | 2 |
| OH | H | —(CH₂)₄— | | p-NO₂ | 1 | 1 |
| OH | H | —(CH₂)₄— | | p-CN | 1 | 2 |
| OH | H | c-Pr | H | p-NMe₂ | 1 | 1 |
| OH | H | —(CH₂)₄— | | p-Me | 1 | 1 |
| OH | H | —(CH₂)₄— | | p-Cl | 1 | 1 |
| OH | H | c-Pr | H | p-Ph | 1 | 1 |
| OH | H | —(CH₂)₄— | | p-Ac | 1 | 4 |
| OH | H | Me | H | p-CO₂Me | 1 | 2 |
| OH | H | i-Pr | H | p-NO₂ | 1 | 1 |
| OH | H | n-Pr | H | p-NHAc | 1 | 2 |
| OH | H | i-Pr | H | p-NHCONH₂ | 1 | 2 |

TABLE 35

Example of Compounds

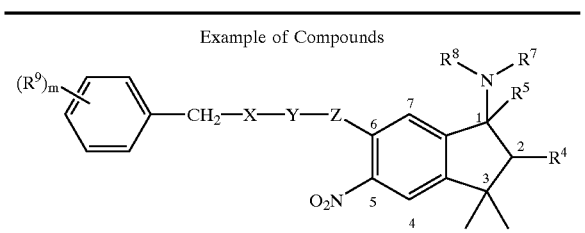

| R⁴ | R⁵ | R⁷ | R⁸ | R⁹ | m | X | Y | Z |
|---|---|---|---|---|---|---|---|---|
| OH | H | H | H | p-Cl | 1 | CO | NH | CH₂ |
| — | | —(CH₂)₄— | | p-OMe | 1 | CO | NH | CH₂ |
| OH | H | Me | H | p-OMe | 1 | CO | NH | CH₂ |
| OH | H | Me | Me | p-F | 1 | CO | NH | CH₂ |
| OH | H | Et | H | p-OMe | 1 | CO | NH | CH₂ |
| OH | H | Et | Et | p-Me | 1 | CO | NH | CH₂ |
| OH | H | n-Pr | H | m,p-(OMe)₂ | 2 | CO | NH | CH₂ |
| OH | H | i-Pr | H | p-OMe | 1 | CO | NH | CH₂ |
| — | | Me | Me | p-Br | 1 | CH₂ | NH | — |
| OH | H | —(CH₂)₄— | | m,p-(OMe)₂ | 2 | CH₂ | NH | — |
| OH | H | Me | H | m,p-Me₃ | 3 | CH₂ | NH | — |
| OH | H | Et | H | m,p-(OMe)₂ | 2 | CH₂ | NH | — |
| OH | H | n-Pr | H | p-NMe₂ | 1 | CH₂ | NH | — |
| OH | H | i-Pr | H | p-t-Bu | 1 | CH₂ | NH | — |
| OH | H | Et | Et | p-NHMe | 1 | CH₂ | NH | — |
| OH | H | —(CH₂)₄— | | m-OMe | 1 | CH₂ | NH | CH₂ |

TABLE 35-continued

Example of Compounds

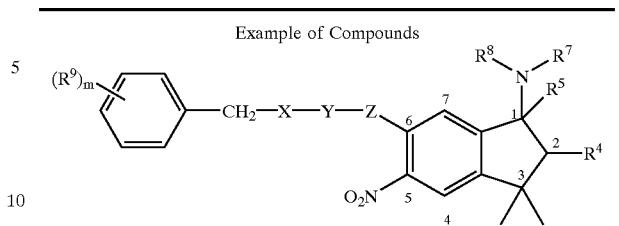

| R⁴ | R⁵ | R⁷ | R⁸ | R⁹ | m | X | Y | Z |
|---|---|---|---|---|---|---|---|---|
| OH | H | Me | H | p-NH₂ | 1 | CH₂ | NH | CH₂ |
| OH | H | Et | H | p-NHCONH₂ | 1 | CH₂ | NH | CH₂ |
| OH | H | n-Pr | H | p-CN | 1 | CH₂ | NH | CH₂ |
| OH | H | i-Pr | H | p-NO₂ | 1 | CH₂ | NH | CH₂ |
| OH | H | Me | Me | p-Ac | 1 | SO₂ | NH | — |
| OH | H | —(CH₂)₄— | | p-CO₂Me | 1 | SO₂ | NH | — |
| OH | H | Me | H | p-CONH₂ | 1 | SO₂ | NH | — |
| OH | H | Et | H | p-COPh | 1 | SO₂ | NH | — |
| OH | H | n-Pr | H | p-NHAc | 1 | SO₂ | NH | — |
| OH | H | i-Pr | H | p-CF₃ | 1 | SO₂ | NH | — |
| OH | H | —(CH₂)₄— | | p-OMe | 1 | NH | CO | NH |
| OH | H | Me | H | p-OMe | 1 | NH | CO | NH |
| OH | H | Et | H | m,p-(OMe)₂ | 2 | NH | CO | NH |
| OH | H | n-Pr | H | p-OCF₃ | 1 | NH | CO | NH |
| OH | H | i-Pr | H | p-OMe | 1 | NH | CO | NH |

TABLE 36

Example of Compounds

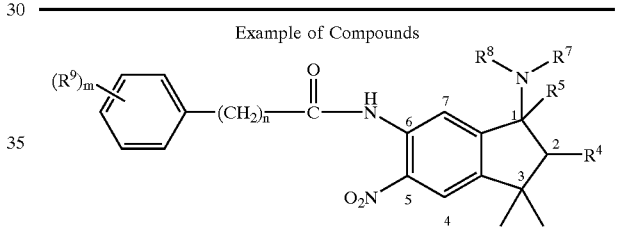

| R¹ | R⁴ | R⁵ | R⁷ | R⁸ | R⁹ | m | n |
|---|---|---|---|---|---|---|---|
| NO₂ | OH | H | c-Pr | H | m-Ph | 1 | 1 |
| CO₂Me | — | | —(CH₂)₄— | | p-OMe | 1 | 2 |
| CO₂Me | OH | H | Me | H | p-OMe | 1 | 1 |
| CO₂Et | OH | H | Me | Me | p-F | 1 | 1 |
| CO₂Me | OH | H | Et | H | p-OMe | 1 | 1 |
| NO₂ | OH | H | c-Pr | H | o-Ph | 1 | 1 |
| CO₂Me | OH | H | n-Pr | H | m,p-(OMe)₂ | 2 | 1 |
| CO₂Me | OH | H | i-Pr | H | p-OMe | 1 | 1 |
| NO₂ | OH | H | Et | H | p-NO₂ | 1 | 1 |
| CO₂Et | OH | H | —(CH₂)₄— | | m,p-(OMe)₂ | 2 | 1 |
| CO₂Me | OH | H | Me | H | m,p-Me₃ | 3 | 1 |
| CO₂Me | OH | H | Et | H | m,p-(OMe)₂ | 2 | 1 |
| CO₂Et | OH | H | n-Pr | H | p-NMe₂ | 1 | 1 |
| CO₂Et | OH | H | i-Pr | H | p-t-Bu | 1 | 2 |
| CO₂Et | OH | H | Et | Et | p-NHMe | 1 | 1 |
| CO₂H | OH | H | —(CH₂)₄— | | m-OMe | 1 | 1 |
| CO₂H | OH | H | Me | H | p-NH₂ | 1 | 1 |
| CO₂H | OH | H | Et | H | p-NHCONH₂ | 1 | 1 |
| Ac | OH | H | n-Pr | H | p-CN | 1 | 1 |
| CO₂H | OH | H | i-Pr | H | p-NO₂ | 1 | 1 |
| CO₂H | OH | H | Me | Me | p-Ac | 1 | 3 |
| Ac | OH | H | —(CH₂)₄— | | p-CO₂Me | 1 | 1 |
| Ac | OH | H | Me | H | p-CONH₂ | 1 | 1 |
| Ac | OH | H | Et | H | p-COPh | 1 | 1 |
| Ac | OH | H | n-Pr | H | p-NHAc | 1 | 1 |
| Ac | OH | H | i-Pr | H | p-CF₃ | 1 | 4 |
| Ac | OH | H | —(CH₂)₄— | | p-OMe | 1 | 1 |
| CO₂Me | OH | H | Me | H | p-OMe | 1 | 1 |
| CO₂Me | OH | H | Et | H | m,p-(OMe)₂ | 2 | 1 |
| CO₂Me | OH | H | n-Pr | H | p-OCF₃ | 1 | 1 |
| CO₂Me | OH | H | i-Pr | H | p-OMe | 1 | 1 |

TABLE 37

Example of Compounds

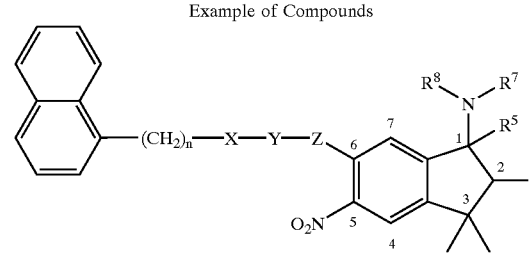

| R⁴ | R⁵ | R⁷ | R⁸ | n | X | Y | Z |
|---|---|---|---|---|---|---|---|
| OH | H | c-Pr | H | 1 | CO | NH | — |
| — | — | Ph | H | 0 | CO | NH | — |
| OH | H | i-Pr | H | 1 | CO | NH | — |
| OH | H | Me | Me | 1 | CO | NH | — |
| OH | H | Et | H | 1 | CO | NH | — |
| OH | H | Et | Et | 1 | CO | NH | — |
| OH | H | n-Pr | H | 1 | CO | NH | — |
| OH | H | n-Pr | n-Pr | 1 | CO | NH | — |
| — | — | i-Pr | H | 1 | CO | NH | — |
| OH | H | i-Pr | i-Pr | 1 | CO | NH | — |
| OH | H | c-Pr | H | 2 | CO | NH | — |
| OH | H | n-Bu | H | 1 | CO | NH | — |
| OH | H | t-Bu | H | 1 | CO | NH | — |
| OH | H | CH=CH₂ | H | 1 | CO | NH | — |
| OH | H | CH₂C≡CH | H | 1 | CO | NH | — |
| OH | H | n-Pentyl | H | 2 | CO | NH | — |
| OH | H | c-Pentyl | H | 3 | CO | NH | — |
| OH | H | n-Hexyl | H | 3 | CO | NH | — |
| OH | H | p-MeOPh | H | 3 | CO | NH | — |
| OH | H | i-Pr | H | 2 | CO | NH | — |
| OH | H | i-Pr | Me | 2 | CO | NH | — |
| OH | H | Et | Et | 4 | CO | NH | — |
| OH | H | Ph | H | 2 | CO | NH | — |
| OH | H | CH₂Ph | H | 2 | CO | NH | — |
| OH | H | CH₂CH₂Ph | H | 2 | CO | NH | — |
| OH | H | Ph | H | 3 | CO | NH | — |
| OH | H | Ph | H | 3 | CO | NH | — |
| OH | H | —(CH₂)₂O(CH₂)₂— | | 2 | CO | NH | — |
| OH | H | —(CH₂)₂NH(CH₂)₂— | | 2 | CO | NH | — |
| OH | H | Ph | H | 2 | CO | NH | — |
| OH | H | Ph | H | 3 | CO | NH | — |

TABLE 38

Example of Compounds

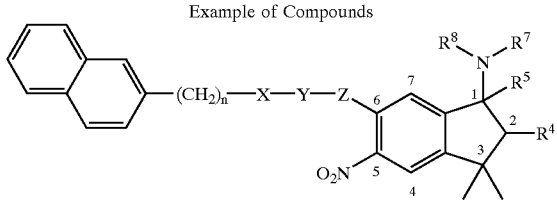

| R⁴ | R⁵ | R⁷ | R⁸ | n | X | Y | Z |
|---|---|---|---|---|---|---|---|
| OH | H | c-Pr | H | 1 | CO | NH | — |
| — | — | Ph | H | 0 | CO | NH | — |
| OH | H | i-Pr | H | 1 | CO | NH | — |
| OH | H | Me | Me | 1 | CO | NH | — |
| OH | H | Et | H | 1 | CO | NH | — |
| OH | H | Et | Et | 1 | CO | NH | — |
| OH | H | n-Pr | H | 1 | CO | NH | — |
| OH | H | n-Pr | n-Pr | 1 | CO | NH | — |
| — | — | i-Pr | H | 1 | CO | NH | — |
| OH | H | i-Pr | i-Pr | 1 | CO | NH | — |
| OH | H | c-Pr | H | 2 | CO | NH | — |
| OH | H | n-Bu | H | 1 | CO | NH | — |
| OH | H | t-Bu | H | 1 | CO | NH | — |
| OH | H | CH=CH₂ | H | 1 | CO | NH | — |

TABLE 38-continued

Example of Compounds

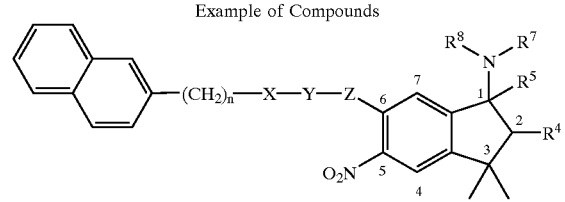

| R⁴ | R⁵ | R⁷ | R⁸ | n | X | Y | Z |
|---|---|---|---|---|---|---|---|
| OH | H | CH₂C≡CH | H | 1 | CO | NH | — |
| OH | H | n-Pentyl | H | 2 | CO | NH | — |
| OH | H | c-Pentyl | H | 3 | CO | NH | — |
| OH | H | n-Hexyl | H | 3 | CO | NH | — |
| OH | H | p-MeOPh | H | 3 | CO | NH | — |
| OH | H | i-Pr | H | 2 | CO | NH | — |
| OH | H | i-Pr | Me | 2 | CO | NH | — |
| OH | H | Et | Et | 4 | CO | NH | — |
| OH | H | Ph | H | 2 | CO | NH | — |
| OH | H | CH₂Ph | H | 2 | CO | NH | — |
| OH | H | CH₂CH₂Ph | H | 2 | CO | NH | — |
| OH | H | Ph | H | 3 | CO | NH | — |
| OH | H | Ph | H | 3 | CO | NH | — |
| OH | H | —(CH₂)₂O(CH₂)₂— | | 2 | CO | NH | — |
| OH | H | —(CH₂)₂NH(CH₂)₂— | | 2 | CO | NH | — |
| OH | H | Ph | H | 2 | CO | NH | — |
| OH | H | Ph | H | 3 | CO | NH | — |

TABLE 39

Example of Compounds

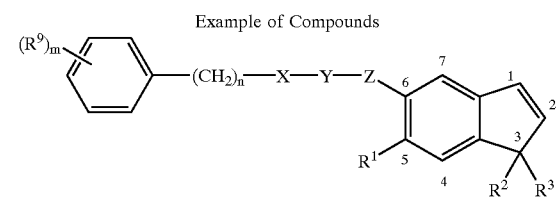

| R¹ | R² | R³ | R⁹ | m | n | X | Y | Z |
|---|---|---|---|---|---|---|---|---|
| H | Me | Me | p-OMe | 1 | 1 | CO | NH | — |
| F | Me | Me | p-OMe | 1 | 1 | CO | NH | — |
| Br | n-Pr | n-Pr | p-OMe | 1 | 1 | CO | NH | — |
| Me | Me | Me | m,p-(OMe)₂ | 2 | 1 | CO | NH | — |
| CF₃ | Me | Et | p-OMe | 1 | 2 | CO | NH | CH₂ |
| CH₂CF₃ | Et | Me | p-OMe | 1 | 1 | CO | NH | — |
| C₂F₅ | Me | Me | p-OMe | 1 | 1 | CO | NH | — |
| OMe | Me | Me | p-OMe | 1 | 2 | CO | NH | — |
| OCF₃ | Me | Me | p-OMe | 2 | 1 | CO | NH | — |
| CH₂OMe | Me | Me | m,p-(OMe)₂ | 2 | 1 | CO | NH | — |
| c-Pr | Me | Me | p-F | 1 | 3 | CO | NH | — |
| NO₂ | Me | Me | p-OMe | 1 | 1 | CO | NH | — |
| CN | Me | Me | p-NHMe | 1 | 1 | CO | NH | — |
| CHO | Me | Me | m,p-(OMe)₂ | 2 | 1 | CH₂ | NH | — |
| CO₂H | Me | Me | m,p-(OMe)₂ | 2 | 1 | CO | NH | — |
| OH | Me | Me | m-OMe | 1 | 1 | CH₂ | NH | CH₂ |
| CH₂OH | Me | Me | m-OMe | 1 | 1 | CO | NH | — |
| NHCHO | Me | Me | m-OMe | 1 | 1 | NH | CO | NH |
| NHCN | Me | Me | o-OMe | 1 | 1 | CO | NH | — |
| NH₂ | Me | Me | m-OMe | 1 | 1 | CO | NH | — |
| NHMe | Me | Me | p-NO₂ | 1 | 1 | CO | NH | — |
| NMe₂ | Me | Me | p-CN | 1 | 1 | CO | NH | — |
| NHCOMe | Me | Me | p-NMe₂ | 1 | 1 | CO | NH | CH₂ |
| NHSO₂Me | Me | Me | p-Me | 1 | 1 | CO | NH | — |
| CONH₂ | Me | Me | p-OH | 1 | 4 | CO | NH | — |
| CONHMe | Me | Me | p-Cl | 1 | 3 | CO | NH | — |
| CONMe₂ | Me | Me | p-Ac | 1 | 2 | CO | NH | — |
| COMe | Me | Me | p-CO₂Me | 1 | 1 | CO | NH | — |
| CO₂Me | Me | Me | p-NHAc | 1 | 1 | CO | NH | — |
| CO₂Ph | Me | Me | p-NHAc | 1 | 1 | CO | NH | — |
| CO₂CH₂Ph | Me | Me | p-NHAc | 1 | 1 | CO | NH | — |

TABLE 40

Example of Compounds $(R^9)_m$—C6H4—$(CH_2)_n$—X—Y—Z—[indene-epoxide structure with positions 1,2,3,4,5,6,7, O, $R^1$, $R^2$, $R^3$]

| $R^1$ | $R^2$ | $R^3$ | $R^9$ | m | n | X | Y | Z |
|---|---|---|---|---|---|---|---|---|
| H | Me | Me | p-OMe | 1 | 1 | CO | NH | — |
| F | Me | Me | p-OMe | 1 | 1 | CO | NH | — |
| Br | n-Pr | n-Pr | p-OMe | 1 | 1 | CO | NH | — |
| Me | Me | Me | m,p-(OMe)$_2$ | 2 | 1 | CO | NH | — |
| CF$_3$ | Me | Et | p-OMe | 1 | 2 | CO | NH | CH$_2$ |
| CH$_2$CF$_3$ | Et | Me | p-OMe | 1 | 1 | CO | NH | — |
| C$_2$F$_5$ | Me | Me | p-OMe | 1 | 1 | CO | NH | — |
| OMe | Me | Me | p-OMe | 1 | 2 | CO | NH | — |
| OCF$_3$ | Me | Me | p-OMe | 2 | 1 | CO | NH | — |
| CH$_2$OMe | Me | Me | m,p-(OMe)$_2$ | 2 | 1 | CO | NH | — |
| c-Pr | Me | Me | p-F | 1 | 3 | CO | NH | — |
| NO$_2$ | Me | Me | p-OMe | 1 | 1 | CO | NH | — |
| CN | Me | Me | p-NHMe | 1 | 1 | CO | NH | — |
| CHO | Me | Me | m,p-(OMe)$_2$ | 2 | 1 | CH$_2$ | NH | — |
| CO$_2$H | Me | Me | m,p-(OMe)$_2$ | 2 | 1 | CO | NH | — |
| OH | Me | Me | m-OMe | 1 | 1 | CH$_2$ | NH | CH$_2$ |
| CH$_2$OH | Me | Me | m-OMe | 1 | 1 | CO | NH | — |
| NHCHO | Me | Me | m-OMe | 1 | 1 | NH | CO | NH |
| NHCN | Me | Me | o-OMe | 1 | 1 | CO | NH | — |
| NH$_2$ | Me | Me | m-OMe | 1 | 1 | CO | NH | — |
| NHMe | Me | Me | p-NO$_2$ | 1 | 1 | CO | NH | — |
| NMe$_2$ | Me | Me | p-CN | 1 | 1 | CO | NH | — |
| NHCOMe | Me | Me | p-NMe$_2$ | 1 | 1 | CO | NH | CH$_2$ |
| NHSO$_2$Me | Me | Me | p-Me | 1 | 1 | CO | NH | — |
| CONH$_2$ | Me | Me | p-OH | 1 | 4 | CO | NH | — |
| CONHMe | Me | Me | p-Cl | 1 | 3 | CO | NH | — |
| CONMe$_2$ | Me | Me | p-Ac | 1 | 2 | CO | NH | — |
| COMe | Me | Me | p-CO$_2$Me | 1 | 1 | CO | NH | — |
| CO$_2$Me | Me | Me | p-NHAc | 1 | 1 | CO | NH | — |
| CO$_2$Ph | Me | Me | p-NHAc | 1 | 1 | CO | NH | — |
| CO$_2$CH$_2$Ph | Me | Me | p-NHAc | 1 | 1 | CO | NH | — |

The compounds of the present invention have asymmetric carbon atoms at the 1- and 2-positions and therefore include optically active isomers based on the asymmetric carbon atoms. Such optically active isomers may also be used in the present invention, like the racemic modifications. In addition, cis- or trans-isomers based on the 1- and 2-positions in the stereo-configuration may also be used. Of these isomers, the trans-isomers are preferable. If the compounds may form salts, their pharmaceutically and veterinarily acceptable salts may also be used as the active ingredients of the present invention.

Examples of the pharmaceutically acceptable salts are hydrochlorides, hydrobromides, sulfates, methanesulfonates, acetates, benzoates, tartarates, phosphates, lactates, maleates, fumarates, malates, gluconates, salicylates. Of these salts, hydrochlorides and methanesulfonates are preferable. [Method for producing the compounds of the present invention]

Methods for producing the compounds of the present invention will be mentioned below.

Compounds of the formula (I) in which X represents C═O, Y represents NH and Z means a bond, namely, compound of formula (I-1a) and compound of formula (I-1b) may be produced according to the method described in known methods (i.e., J. M. Evans et al., *J. Med. Chem.,* 1984, 27, 1127, J. M. Evans et al.,*J. Med. Chem.,* 1986, 29, 2194, J. T. North et al., *J. Org. Chem.,* 1995, 60, 3397, Japanese Patent Application Laid-open No. Hei 56-57785, Japanese Patent Application Laid-open No. Hei 56-57786, Japanese Patent Application Laid-open No. Sho 58-188880, Japanese Patent Application Laid-open No. Hei 2-141).

Compound of the formula (I-1a) may be produced, as shown in Reaction Scheme 1, by reacting a compound of formula (1) with an acid chloride of formula (2) in the presence of a base or by reacting the compound of the formula (1) with a carboxylic acid of formula (3) by using a condensation agent.

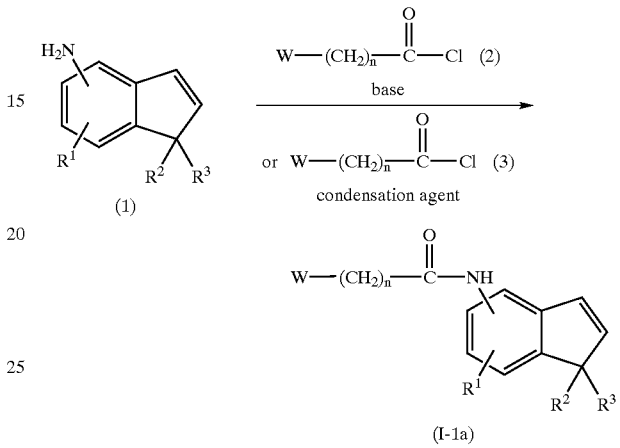

Reaction Scheme 1
(Case of X-Y-Z = CONH-)

(wherein $R^1$, $R^2$, $R^3$, W and n have the same meanings as defined above.)

The solvents usable for the reaction of the compound of the formula (1) with the compound of the formula (2) include, for example, aromatic solvents such as benzene or toluene; ester solvents such as ethyl acetate or methyl acetate; sulfoxide solvents such as dimethylsulfoxide; amide solvents such as dimethylformamide or dimethylacetamide; ethereal solvents such as ethyl ether, dimethoxyethane, 1,4-dioxane or tetrahydrofuran; and halogenated solvents such as dichloromethane, chloroform or dichloroethane. The reaction may be carried out in the absence of a solvent. Of these solvents, halogenated solvents and amide solvents are preferable.

The reaction temperature is, usually, from −20° C. to a reflux temperature for the reaction solvent used, preferably from −10° C. to 30° C.

Regarding the molar ratio of the starting compounds, the ratio of the compound of the formula (2)/the compound of the formula (1) (by molar ratio) is within the range of from 0.5 to 4.0, preferably from 1.0 to 2.0.

The ratio of the base/the compound of the formula (2) is within the range of 0.5 to 2.0, preferably within the range of 1.0 to 1.5.

The base to be used includes, for example, inorganic bases such as potassium carbonate, potassium hydrogencarbonate, sodium carbonate, sodium hydrogencarbonate, potassium hydroxide and sodium hydroxide, and organic bases such as triethylamine, ethyldiisopropylamine, pyridine, 2,6-lutidine, 2,6-di-t-butylpyridine, N-methylmorpholine and proton sponge. Of these bases, triethylamine and ethyldiisopropylamine are preferable.

The solvents usable for the reaction of the compound of the formula (1) with the compound of the formula (3) include, for example, aromatic solvents such as benzene or toluene; ester solvents such as ethyl acetate or methyl acetate; sulfoxide solvents such as dimethylsulfoxide; amide solvents such as dimethylformamide or dimethylacetamide, ethereal solvents such as ethyl ether, dimethoxyethane, 1,4-dioxane or tetrahydrofuran, and halogenated solvents such as dichloromethane, chloroform or dichloroethane. The reaction may be carried out in the absence of a solvent. Of these solvents, halogen compound solvents are preferable.

The reaction temperature is, usually, from −20° C. to a reflux temperature for the reaction solvent used, preferably from −10° C. to 30° C.

Regarding the molar ratio of the starting compounds, the ratio of the compound of the formula (3)/the compound of the formula (1) (by molar ratio) is within the range of from 0.5 to 4.0, preferably from 1.0 to 2.0.

The condensation agent to be used includes, for example, dicyclohexylcarbodiimide, diisopropylcarbodiimide, N-ethyl-N'-3-dimethylaminopropylcarbodiimide and carbonyldiimidazole.

N-hydroxysuccinimide, 1-hydroxybenzotriazole and 3-hydroxy-4-oxo-3,4-dihydro-1,2,3-benzotriazine may be added to these condensation agents.

Compound of the formula (I-1b) may be produced, as shown in Reaction Scheme 2, by reacting the compound of the formula (I-1a) with N-Bromosuccinimide (NBS) to give bromohydrin of formula (4) in the presence of water and then, the obtained bromohydrin is subjected to an epoxidation in the presence of a base, or directly subjecting the compound of the formula (I-1a) to an epoxidation with a peroxide.

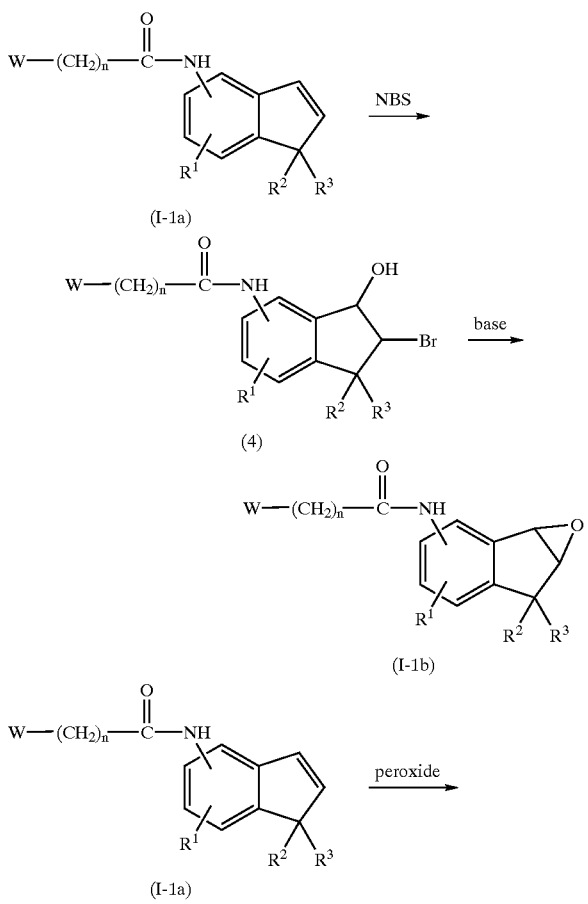

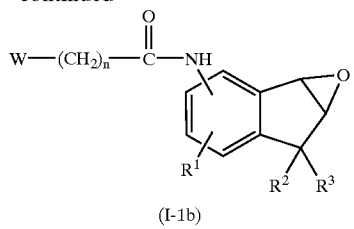

(wherein $R^1$, $R^2$, $R^3$, W and n have the same meanings as defined above.)

The solvents usable for the reaction of the compound of the formula (I-1a) with NBS include, for example, aromatic solvents such as benzene or toluene; ester solvents such as ethyl acetate or methyl acetate; sulfoxide solvents such as dimethylsulfoxide; amide solvents such as dimethylformamide or dimethylacetamide; ethereal solvents such as ethyl ether, dimethoxyethane, 1,4-dioxane or tetrahydrofuran; and halogenated solvents such as dichloromethane, chloroform or dichloroethane. Of these solvents, sulfoxide solvents are preferable.

The reaction temperature is normally from −20° C. to a reflux temperature for the reaction solvent used, preferably from −10° C. to 30° C.

Regarding the molar ratio of the starting compounds, the ratio of NBS/the compound of the formula (I-1a) (by molar ratio) is within the range of from 0.5 to 4.0, preferably within the range of 1.0 to 3.0.

The solvents usable for the reaction of the compound of the formula (4) and the base are as follows.

The solvents include, for example, aromatic solvents such as benzene or toluene; ester solvents such as ethyl acetate or methyl acetate; sulfoxide solvents such as dimethylsulfoxide; amide solvents such as dimethylformamide or dimethylacetamide; ethereal solvents such as ethyl ether, dimethoxyethane, 1,4-dioxane or tetrahydrofuran; halogenated solvents such as dichloromethane, chloroform or dichloroethane; and alcohol solvents such as methanol, ethanol or propanol. The reaction may be carried out in the water. Further, the solvents may be used in combination. Preferable solvent is a mixture of ethereal solvents and water.

The reaction temperature is normally from −20° C. to a reflux temperature for the reaction solvent used, preferably from −10° C. to 30° C.

Regarding the molar ratio of the starting compounds, the ratio of the base/the compound of the formula (4) (by molar ratio) is within the range of from 0.5 to 4.0, preferably from 1.0 to 2.0.

The base to be used includes, for example, inorganic bases such as potassium carbonate, potassium hydrogencarbonate, sodium carbonate, sodium hydrogencarbonate, potassium hydroxide and sodium hydroxide. Of these bases, potassium hydroxide and sodium hydroxide are preferable.

The solvents usable for the reaction of the compound of the formula (I-1a) with a peroxide are as follows.

Such solvents include, for example, aromatic solvents such as benzene or toluene; ester solvents such as ethyl acetate or methyl acetate; sulfoxide solvents such as dimethylsulfoxide; amide solvents such as dimethylformamide or dimethylacetamide; ethereal solvents such as ethyl ether, dimethoxyethane, 1,4-dioxane or tetrahydrofuran; halogenated solvents such as dichloromethane, chloroform or dichloroethane; and alcohol solvents such as methanol, ethanol or propanol. The reaction may be carried out in the water. Of these solvents, halogenated solvents are preferable.

The reaction temperature is normally from −20° C. to a reflux temperature for the reaction solvent to be used, preferably from −10° C. to 30° C.

Regarding the molar ratio of the starting compounds, the ratio of the peroxide/the compound of the formula (I-1a) (by molar ratio) is within the range of from 0.5 to 4.0, preferably from 1.0 to 2.0.

The peroxide to be used includes, for example, hydrogen peroxide, perbenzoic acid, m-chloroperbenzoic acid, peracetic acid and trifluoroperacetic acid. Of these peroxides, m-chloroperbenzoic acid is preferable.

Optically active isomers of the compounds of the formula (I-1b) may be synthesized by utilizing methods of asymmetric synthesis (shown by Japanese National Publication No. Hei 5-507645, Japanese Patent Application Laid-open No. Hei 5-301878, Japanese Patent Application Laid-open No. Hei 7-285983, European Patent No. 535377 and U.S. Pat. No. 5420314.

Namely, the optically active isomers of said compound may be produced by reacting the compound of the formula (I-1a) with an oxidizing agent in the presence of salen manganese complex disclosed by the above-mentioned publications.

The oxidizing agent to be used includes, for example, sodium hypochlorite, potassium hypochlorite, sodium iodosobenzoate and m-chloroperbenzoic acid. Of these oxidizing agents, sodium hypochlorite and sodium iodosobenzoate are preferable.

An axial ligand may be added in this reaction. Examples of the axial ligand to be used are N-methylmorpholine-N-oxide, 4-phenylpyridine-N-oxide, 4-methylpyridine-N-oxide, pyridine-N-oxide, dimethylsulfoxide, triphenylphosphine, triphenylphosphine and triphenylphosphine oxide. Of these axial ligands, 4-phenylpyridine-N-oxide is preferable.

The compound of the formula (I-1b) may also be produced, as shown in Reaction Scheme 3, by deprotection of an acetyl group of a compound of formula (5) by using a base to give a compound of formula (6) and then, reacting the obtained compound of the formula (6) with an acid chloride of formula (7) in the presence of a base or reacting the compound of the formula (6) with a carboxylic acid of formula (8) by using a condensation agent.

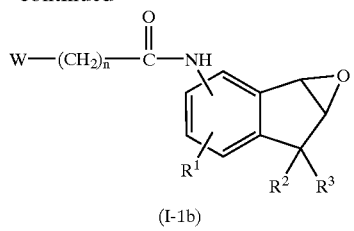

(I-1b)

(wherein $R^1$, $R^2$, $R^3$, W and n have the same meanings as defined above.)

The compound of the formula (6) may be produced by reacting the compound of the formula (5) by using a base.

The solvents usable for this reaction include, for example, aromatic solvents such as benzene and toluene; ester solvents such as ethyl acetate or methyl acetate; sulfoxide solvents such as dimethylsulfoxide; amide solvents such as dimethylformamide or dimethylacetamide; ethereal solvents such as ethyl ether, dimethoxyethane, 1,4-dioxane or tetrahydrofuran; halogenated solvents such as dichloromethane, chloroform or dichloroethane; and alcohol solvents such as methanol, ethanol or propanol. The reaction may be carried out in the water. Further, the solvents may be used in combination. Preferable solvents are a mixture of amide solvents/water and a mixture of alcohol solvent/water.

The reaction temperature is normally from −20° C. to a reflux temperature for the reaction solvent used, preferably from 0° C. to the reflux temperature for the reaction solvent used.

Regarding the molar ratio of the starting compounds, the ratio of the base/the compound of the formula (5) (by molar ratio) is within the range of from 0.5 to 4.0, preferably within from 1.0 to 2.0.

The base to be used include, for example, inorganic bases such as potassium carbonate, potassium hydrogencarbonate, sodium carbonate, sodium hydrogencarbonate, potassium hydroxide and sodium hydroxide. Of these bases, potassium hydroxide and sodium hydroxide are preferable.

The reaction of the compound of the formula (6) with the acid chloride of the formula (7) and the reaction of the compound of the formula (6) with the carboxylic acid of the formula (8) may be conducted under conditions similar to those shown in the Reaction Scheme 1.

In compound of the formula (I-2a) and compound of the formula (I-2b) which are compounds of the formula (I) in which X represents $CH_2$, Y represents NH and Z means a bond, the compound of the formula (I-2a) may be produced, as shown in Reaction Scheme 4, by reducing the compound of the formula (I-1a) by using a reducing agent.

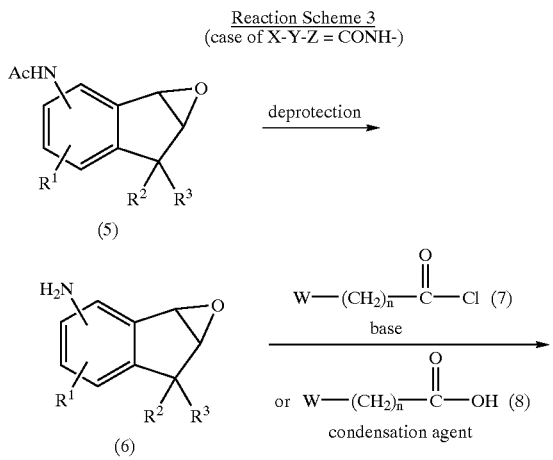

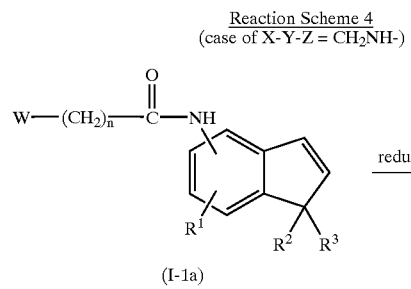

-continued

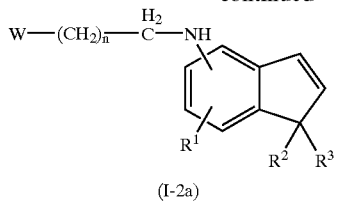

(I-2a)

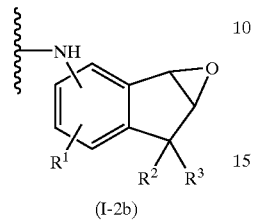

(I-2b)

(wherein $R^1$, $R^2$, $R^3$, W and n have the same meanings as defined above.)

The solvents usable for the reaction of the compound of the formula (I-1a) with a reducing agent include, for example, aromatic solvents such as benzene or toluene; ester solvents such as ethyl acetate or methyl acetate; sulfoxide solvents such as dimethylsulfoxide; amide solvents such as dimethylformamide or dimethylacetamide; ethereal solvents such as ethyl ether, dimethoxyethane, 1,4-dioxane or tetrahydrofuran; halogenated solvents such as dichloromethane, chloroform or dichloroethane; and alcohol solvents such as methanol, ethanol or propanol. The reaction may be carried out in the water. Of these solvents, the ether solvents are preferable.

The reaction temperature is normally from −20° C. to a reflux temperature for the reaction solvent used, preferably from −10° C. to 30° C.

Regarding the molar ratio of the starting compounds, the ratio of the reducing agent/the compound of the formula (I-1a) (by molar ratio) is within the range of from 0.5 to 4.0, preferably from 1.0 to 2.0.

The reducing agent to be used includes, for example, lithium aluminum hydride and sodium boron hydride. Of these reducing agents, the lithium aluminum hydride is preferable.

The compound of the formula (I-2b) may be produced by dealing with the obtained compound of the formula (I-2a) under conditions similar to those of the epoxidation method of the Reaction Scheme 2.

The compound of the formula (I-2a) may be produced, as shown in Reaction Scheme 5, by reacting the compound of the formula (1) with a compound of formula (9) in the presence of a base or by reacting the compound of the formula (1) with a compound of formula (10) to give an imine compound of formula (11) and then reducing the imine compound by using a suitable reducing agent.

Reaction Scheme 5
(case of X-Y-Z = CH$_2$NH-)

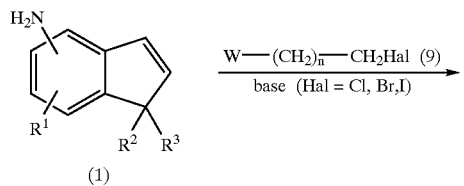

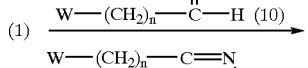

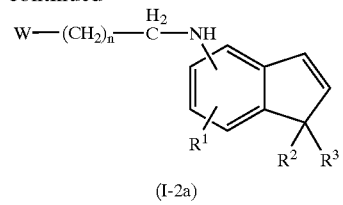

(I-2a)

(1) $\xrightarrow{\text{W—(CH}_2)_n\text{—C(=O)—H (10)}}$

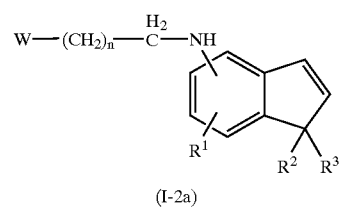

(11)

$\xrightarrow{\text{reducing agent}}$

W—(CH$_2$)$_n$—CH$_2$—NH (I-2a)

(wherein $R^1$, $R^2$, $R^3$, W and n have the same meanings as defined above.)

The solvents usable for the reaction of the compound of the formula (1) with the compound of the formula (9) include, for example, aromatic solvents such as benzene or toluene; ester solvents such as ethyl acetate or methyl acetate; sulfoxide solvents such as dimethylsulfoxide; amide solvents such as dimethylformamide or dimethylacetamide; ethereal solvents such as ethyl ether, dimethoxyethane, 1,4-dioxane or tetrahydrofuran; and halogenated solvents such as dichloromethane, chloroform or dichloroethane. The reaction may be carried out in the absence of a solvent. Of these solvents, the halogenated solvents and amide solvents are preferable.

The reaction temperature is normally from −20° C. to a reflux temperature for the reaction solvent used, preferably from 0° C. to the reflux temperature.

Regarding the molar ratio of the starting compounds, the ratio of the compound of the formula (9)/the compound of the formula (1) (by molar ratio) is within the range of from 0.5 to 4.0, preferably from 1.0 to 2.0.

The ratio of the base/the compound of the formula (9) is within the range of 0.5 to 2.0, preferably from 1.0 to 1.5.

The base to be used includes, for example, inorganic bases such as potassium carbonate, potassium hydrogencarbonate, sodium carbonate, sodium hydrogencarbonate, potassium hydroxide, sodium hydroxide and sodium hydride, and organic bases such as triethylamine, ethyldiisopropylamine, pyridine, 2,6-lutidine, 2,6-di-t-butylpyridine, N-methylmorpholine and proton sponge. Of these bases, triethylamine and ethyldiisopropylamine are preferable.

The solvents usable for the reaction of the compound of the formula (1) with the compound of the formula (10) include, for example, aromatic solvents such as benzene or toluene; ester solvents such as ethyl acetate and methyl acetate; sulfoxide solvents such as dimethylsulfoxide; amide solvents such as dimethylformamide or dimethylacetamide, ethereal solvents such as ethyl ether, dimethoxyethane, 1,4-dioxane or tetrahydrofuran, halogenated solvents such as dichloromethane, chloroform or dichloroethane; and alcohol solvents such as methanol, ethanol or propanol. The reaction may be carried out in the absence of a solvent. Of these solvents, the aromatic solvents and alcohol solvents are preferable.

The reaction temperature is normally from −20° C. to a reflux temperature for the reaction solvent used, preferably from 0° C. to the reflux temperature.

Regarding the molar ratio of the starting compounds, the ratio of the compound of the formula (10)/the compound of the formula (1) (by molar ratio) is within the range of from 0.5 to 4.0, preferably from 1.0 to 2.0.

With respect to this reaction, coexistence with a desiccant, e.g., Molecular Sieves is generally preferable in the reaction system.

In a case that the aromatic solvents which do not intimately mix with water are used as a reaction solvent, it is preferable to separate water out of the system by conducting azeotropic dehydration. At that time, coexistence with an acid, e.g., paratoluene sulfonic acid, in a catalytic amount may render good results.

The amount of the acid at that time is enough to be used within the range of 0.1 to 20 mol %, preferably within the range of 0.1 to 5 mol %, based on the compound of the formula (1).

The compound of the formula (I-2a) may be obtained, without isolating the compound of the formula (11), by directly adding a reducing agent to a solution containing the compound of the formula (1), the compound of the formula (10) and a reaction solvent.

The solvents usable for the reaction of the compound of the formula (11) with the reducing agent include, for example, aromatic solvents such as benzene or toluene; ester solvents such as ethyl acetate or methyl acetate; sulfoxide solvents such as dimethylsulfoxide; amide solvents such as dimethylformamide or dimethylacetamide; ethereal solvents such as ethyl ether, dimethoxyethane, 1,4-dioxane or tetrahydrofuran; halogenated solvents such as dichloromethane, chloroform or dichloroethane; and alcohol solvents such as methanol, ethanol or propanol. The reaction may be carried out in the water. Of these solvents, ethereal solvents are preferable.

The reaction temperature is normally from −20° C. to a reflux temperature for the reaction solvent used, preferably from −10° C. to 30° C.

Regarding the molar ratio of the starting compounds, the ratio of the reducing agent/the compound of the formula (11) (by molar ratio) is within the range of from 0.5 to 4.0, preferably from 1.0 to 2.0.

The reducing agent to be used includes, for example, lithium aluminum hydride and sodium boron hydride. Of these reducing agents, the lithium aluminum hydride is preferable.

In compound of the formula (I-3a) and compound of the formula (I-3b) which are compounds of the formula (I) in which X represents $SO_2$, Y represents NH and Z means a bond, the compound of the formula (I-3a) may be produced, as shown in Reaction Scheme 6, by reacting the compound of the formula (1) with a compound of formula (12) in the presence of a base.

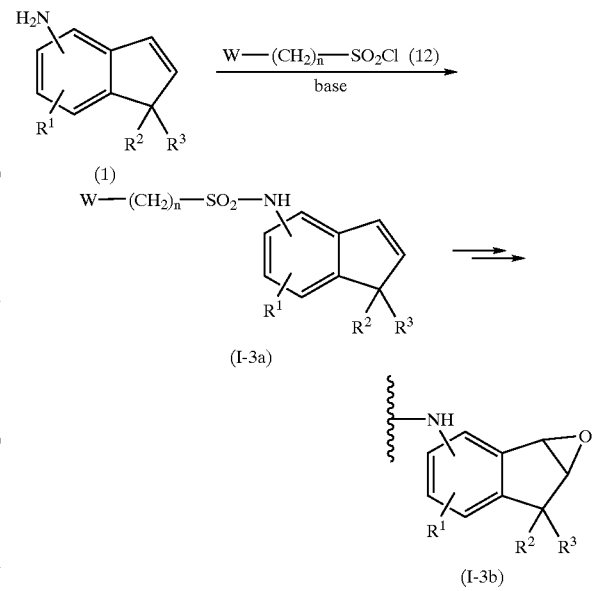

(wherein $R^1$, $R^2$, $R^3$, W and n have the same meanings as defined above.)

The compound of the formula (I-3a) may be reacted under the conditions similar to those in the method for producing the compound of the formula (I-1a) from the compound of the formula (1) and the compound of the formula (2) in the Reaction Scheme 1.

The compound of the formula (I-3b) may be obtained by dealing with the obtained compound of the formula (I-3a) under the conditions similar to those in the epoxidation method shown in the Reaction Scheme 2.

In compound of the formula (I-4a) and compound of the formula (I-4b) which are compounds of the formula (I) in which X represents NH, Y represents C=O and Z represents NH, the compound of the formula (I-4a) may be produced, as shown in Reaction Scheme 7, by reacting the compound of the formula (1) with a compound of formula (13).

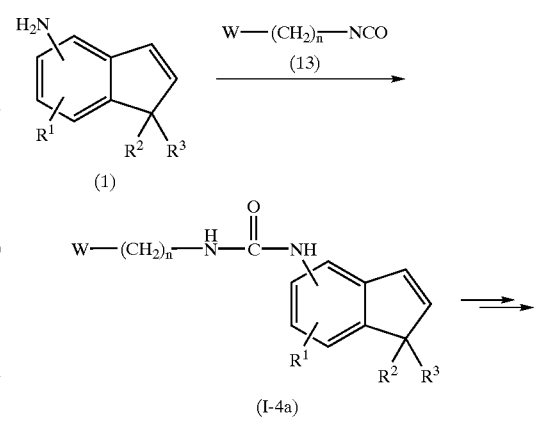

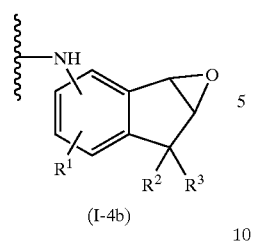

(I-4b)

(wherein $R^1$, $R^2$, $R^3$, W and n have the same meanings as defined above.)

The solvents usable for the reaction of the compound of the formula (1) with the compound of the formula (13) include, for example, aromatic solvents such as benzene or toluene; ester solvents such as ethyl acetate or methyl acetate; sulfoxide solvents such as dimethylsulfoxide; amide solvents such as dimethylformamide or dimethylacetamide; ethereal solvents such as ethyl ether, dimethoxyethane, 1,4-dioxane or tetrahydrofuran; halogenated solvents such as dichloromethane, chloroform or dichloroethane; and alcohol solvents such as methanol, ethanol or propanol. The reaction may be carried out in the absence of a solvent. Of these solvents, halogenated solvents and amide solvents are preferable.

The reaction temperature is normally from −20° C. to a reflux temperature for the reaction solvent used, preferably from 0° C. to a reflux temperature of a reaction solvent to be used.

Regarding the molar ratio of the starting compounds, the ratio of the compound of the formula (13)/the compound of the formula (1) (by molar ratio) is within the range of from 0.5 to 4.0, preferably within the range of 1.0 to 2.0.

The compound of the formula (I-4b) may be produced by dealing with the obtained compound of the formula (I-4a) under conditions similar to those of the epoxidation method of the Reaction Scheme 2.

Compounds of the formula (I) in which $R^6$ represents amino group or $C_{1-6}$ alkylamino group, di $C_{1-6}$ alkylamino group, $C_{3-6}$ cylcoalkylamino group, ary $C_{1-6}$ alkylamino group, di(aryl $C_{1-6}$ alkyl)amino group, 1-pyrrolidinyl group, 1-piperidyl group, 1-piperazinyl group or 1-morpholino group, namely, a compound of formula (I-c) may be produced, as shown in Reaction Scheme 8, by reacting the compound of the formula (I-b) (the compound of the formula (I-b) includes the above-mentioned compounds of the formula (I-1b), the formula (I-2b), the formula (I-3b) and the formula (I-4b)) with an amine compound of formula (14) in an inert solvent.

Reaction Scheme 8

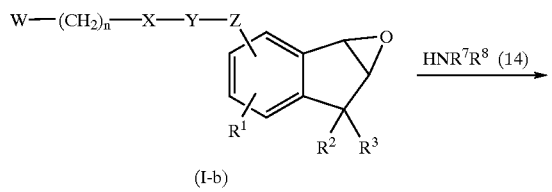

(I-b)

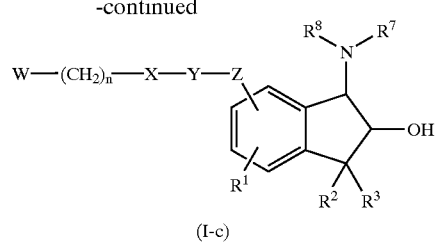

(I-c)

(wherein $R^1$, $R^2$, $R^3$, $R^7$, $R^8$, W, X, Y, Z and n have the same meanings as defined above.)

Solvents usable for the reaction of the compound of the formula (I-b) with the amine compound of the formula (14) are shown below.

Such solvents includes, for example, sulfoxide solvents such as dimethylsulfoxide; amide solvents such as dimethylformamide or dimethylacetamide; ethereal solvents such as ethyl ether, dimethoxyethane or tetrahydrofuran; halogenated solvents such as dichloromethane, chloroform and dichloroethane; and alcohol solvents such as methanol, ethanol or propanol. The reaction may be carried out in the absence of a solvent. Of these solvents, alcohol solvents are preferable.

The reaction temperature is normally from −20° C. to a reflux temperature for the reaction solvent used, preferably from 60° C. to 100° C.

Regarding the molar ratio of the starting compounds, the ratio of the compound of the formula (14)/the compound of the formula (I-b) (by molar ratio) is within the range of from 0.5 to 20.0, preferably from 1.0 to 10.0.

Compounds of the formula (I-c) in which X represents C=O, Y represents NH and Z means a bond, namely, a compound of formula (I-1c) may be produced, as shown in Reaction Scheme 9, by reacting a compound of formula (17) which is obtained by deprotection of an acetyl group of a compound of formula (16) (the compound of the formula (16) may be synthesized according to the methods described by, e.g., Smith, J. G. et al., Org. Prep. Proc. Int., 123–131, 10, 1978, Buckle, D. R. et al., J. Med. Chem., 919–926, 34, 1991, Stock, L. M. et al., J. Am. Chem. Soc., 4247, 94, 1972 and Japanese Patent Application Laid open No. Hei 2-141) by usual method, with the acid chloride of the formula (7) in the presence of the base, or by reacting the compound of the formula (17) with the carboxylic acid of the formula (8) by using a condensation agent.

Reaction Scheme 9
(case of X-Y-Z = CONH-)

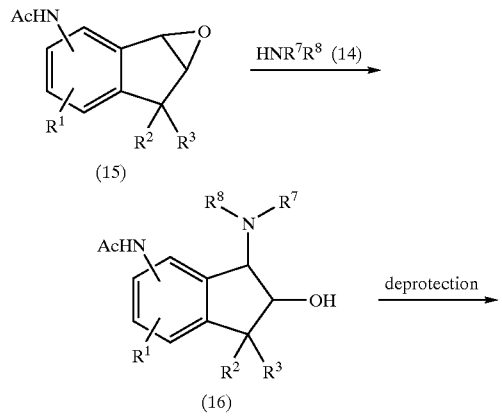

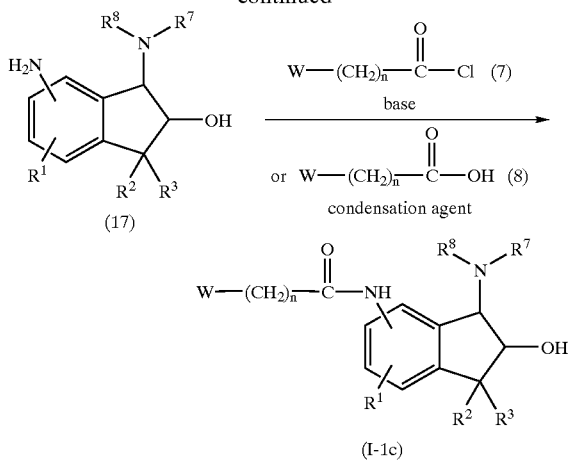

(wherein $R^1$, $R^2$, $R^3$, $R^7$, $R^8$, W and n have the same meanings as defined above, provided that $R^7$ and $R^8$ do not represent hydrogen atom.)

The reaction of a compound of formula (15) with the compound of the formula (14) may be conducted under conditions similar to those shown in the Reaction Scheme 8.

The reaction in the deprotection of a compound of formula (16) may be conducted under conditions similar to those shown in the Reaction Scheme 3.

The reaction of a compound of formula (17) with the compound of the formula (7) and the reaction of the compound of the formula (17) with the compound of the formula (8) may be conducted under conditions similar to those shown in the Reaction Scheme 1.

Compounds of the formula (I) in which $R^6$ represents amino group, namely, compound of formula (I-d) may be easily produced, as shown in Reaction Scheme 10, by treating the compound of the formula (I-b) with ammonia. (The conversion from the compound of the formula (I-b) to the compound of the formula (I-d) is known and may be accomplished according to the methods described in Japanese Patent Application Laid-open No. Sho 58-67683, Japanese Patent Application Laid-open No. Sho 58-188880 and Japanese Patent Application Laid-open No. Sho 58-201776.)

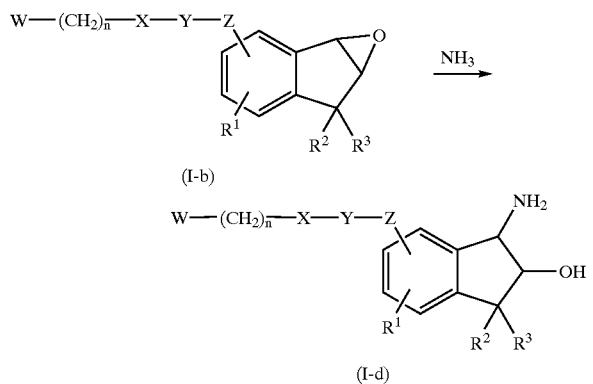

(wherein $R^1$, $R^2$, $R^3$, W, X, Y, Z and n have the same meanings as defined above.)

Solvents usable for the reaction include, for example, sulfoxide solvents such as dimethylsulfoxide; amide solvents such as dimethylformamide or dimethylacetamide; ethereal solvents such as ethyl ether, dimethoxyethane or tetrahydrofuran; halogenated solvents such as dichloromethane, chloroform or dichloroethane; and alcohol solvents such as methanol or ethanol. Of these solvents, the alcohol solvents are preferable.

The reaction temperature is normally from ice-cooled temperature to a reflux temperature for the reaction solvent used, preferably from 40° C. to 80° C.

It is preferable to conduct the reaction in a pressure glass tube or an autoclave.

The compound of the formula (I-d) may also be produced, as shown in Reaction Scheme 11, through an azido compound of formula (19). (The conversion from the compound of the formula (I-b) to the compound of the formula (I-d) is known and said conversion may be accomplished according to a method described by Buckle, D. R. et al., *J. Med. Chem.*, 919–926, 34, 1991.)

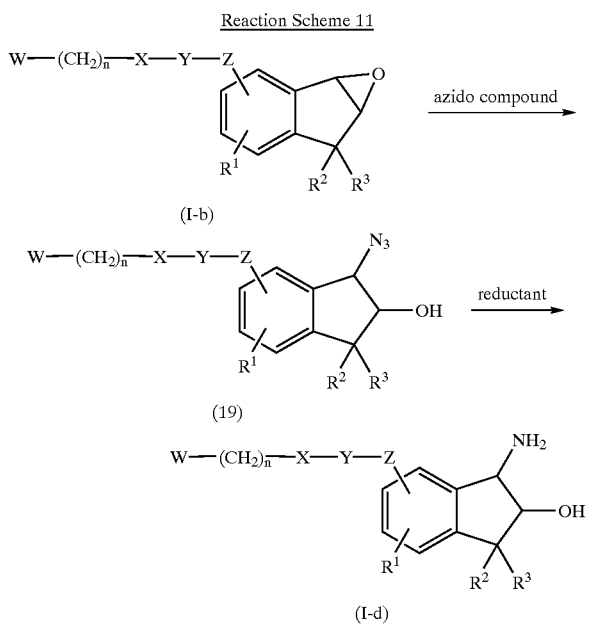

(wherein $R^1$, $R^2$, $R^3$, W, X, Y, Z and n have the same meanings as defined above.)

The compound of formula (19) may be produced by reacting the compound of the formula (I-b) with an azido compound such as sodium azide, lithium azide or trimethylsilyl azide in an inert solvent.

Solvents usable for the reaction include, for example, sulfoxide solvents such as dimethylsulfoxide; amide solvents such as dimethylformamide or dimethylacetamide; ethereal solvents such as ethyl ether, dimethoxyethane or tetrahydrofuran; halogenated solvents such as dichloromethane, chloroform or dichloroethane; and aromatic solvents such as benzene or toluene. Of these solvents, the aromatic solvents are preferable.

The reaction temperature is normally from ice-cooled temperature to a reflux temperature for the reaction solvent used.

Regarding the molar ratio of the starting compounds, the ratio of the azido compound/the compound of the formula (I-b) (by molar ratio) is within the range of from 0.5 to 5.0, preferably from 1.0 to 2.0.

Solvents usable for the reaction of the compound of the formula (19) with the reducing agent include, for example, aromatic solvents such as benzene or toluene; ester solvents such as ethyl acetate or methyl acetate; sulfoxide solvents such as dimethylsulfoxide; amide solvents such as dimethylformamide or dimethylacetamide; ethereal solvents such as ethyl ether, dimethoxyethane, 1,4-dioxane or tetrahydrofuran; halogenated solvents such as dichloromethane, chloroform or dichloroethane; and alcohol solvents such as methanol, ethanol or propanol. The reaction may be carried out in the water. Of these solvents, the ether solvents and the alcohol solvents are preferable.

The reaction temperature is normally from −20° C. to a reflux temperature for the reaction solvent used, preferably from −10° C. to 30° C.

Regarding the molar ratio of the starting compounds, the ratio of the reducing agent/the compound of the formula (19) (by molar ratio) is within the range of from 0.5 to 4.0, preferably from 1.0 to 2.0.

In a case of catalytic hydrogenation, however, amount of catalyst to be used is within the range of 0.1 to 50% by weight, preferably from 1 to 10% by weight.

The reducing agents to be used include, for example, lithium aluminum hydride and sodium boron hydride. Of these reducing agents, the lithium aluminum hydride is preferable.

Moreover, conditions of catalytic hydrogenation may be used, e.g., catalysts such as palladium-carbon (5%/10%), palladium black and platinum oxide may be used.

Compounds of the formula (I) in which $R^7$ and $R^8$ taken together with nitrogen atoms to which they are bonded represent pyrrolyl group, namely, compound of formula (I-f) may be produced, as shown in Reaction Scheme 12, by reacting the compound of the formula (I-d) with a compound of formula (20) in an inert solvent and in the presence of an acid catalyst.

Reaction Scheme 12

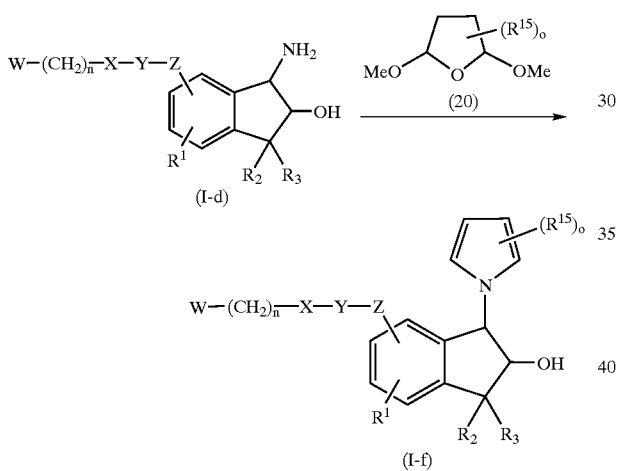

(wherein $R^1$, $R^2$, $R^3$, $R^{15}$, X, Y, Z, W and n have the same meanings as defined above, and o means 0 or an integer of 1 to 4; when o is 2, 3 and 4, $R^{15}$ may be the same or different.

Solvents usable for this reaction include, for example, sulfoxide solvents such as dimethylsulfoxide; amide solvents such as dimethylformamide or dimethylacetamide; ethereal solvents such as ethyl ether, dimethoxyethane or tetrahydrofuran; and halogenated solvents such as dichloromethane, chloroform or dichloroethane. The reaction may be carried out in the absence of a solvent. Moreover, an acid catalyst may be used as a solvent as it is.

The reaction temperature is normally from ice-cooled temperature to a reflux temperature for the reaction solvent used, preferably the reflux temperature for the solvent used.

Regarding the molar ratio of the starting compounds, the ratio of the compound of the formula (20)/the compound of the formula (I-d) (by molar ratio) is within the range of from 0.5 to 4.0, preferably within the range of 1.0 to 2.0.

The acid catalyst to be used includes, for example, hydrochloric acid, sulfuric acid, formic acid, acetic acid and propionic acid.

Compound of the formula (I-g) and compound of the formula (I-g') which are compounds of the formula (I) in which $R^7$ and $R^8$ taken together with nitrogen atoms to which they are bonded represent pyrazolyl group, may be produced, as shown in Reaction Scheme 13, from the compound of the formula (I-b) by two steps.

Reaction Scheme 13

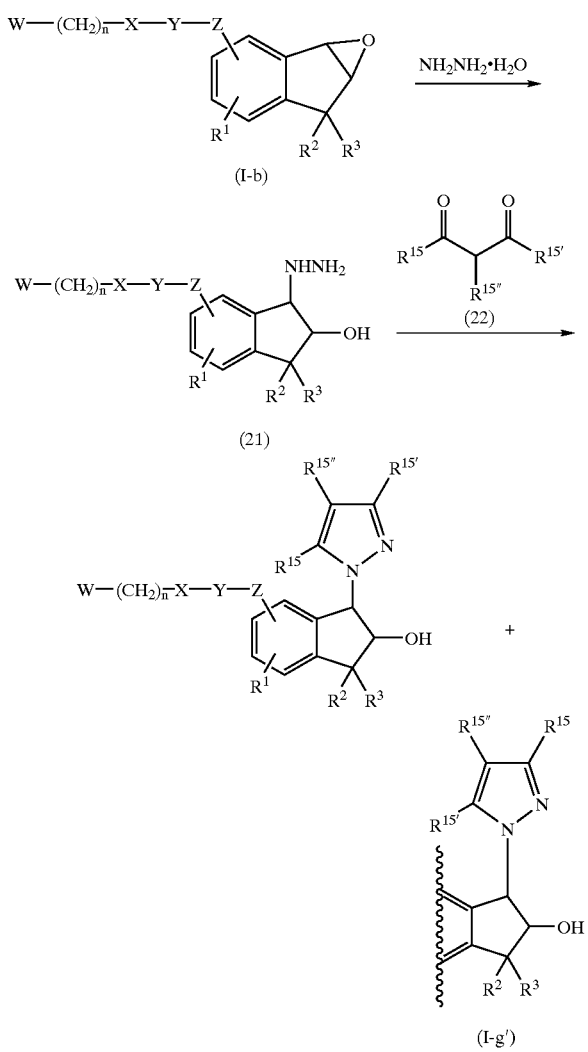

(wherein $R^1$, $R^2$, $R^3$, $R^{15}$, X, Y, Z, W and n have the same meanings as defined above. $R^{15'}$ and $R^{15''}$ each have the same meanings as defined in $R^{15}$.)

A compound of formula (21) may be produced by reacting the compound of the formula (I-b) with hydrazine hydrate in an inert solvent.

Solvents usable for this reaction include, for example, sulfoxide solvents such as dimethylsulfoxide; amide solvents such as dimethylformamide or dimethylacetamide; ethereal solvents such as ethyl ether, dimethoxyethane or tetrahydrofuran; halogenated solvents such as dichloromethane, chloroform or dichloroethane; or alcohol solvents such as methanol or ethanol. Of these solvents, the alcohol solvents are preferable.

The reaction temperature is normally from ice-cooled temperature to a reflux temperature for the reaction solvent used, preferably from 40° C. to 80° C.

Regarding the molar ratio of the starting compounds, the ratio of the hydrazine hydrate/the compound of the formula (I-b) (by molar ratio) is within the range of from 0.5 to 10.0, preferably from 1.0 to 2.0.

The compound of formula (I-g) and the compound of the formula (I-g') may be produced by reacting the compound of formula (21) with a compound of formula (22) in an inert solvent.

Solvents usable for this reaction include, for example, sulfoxide solvents such as dimethylsulfoxide; amide solvents such as dimethylformamide or dimethylacetamide; ethereal solvents such as ethyl ether, dimethoxyethane or tetrahydrofuran; halogenated solvents such as dichloromethane, chloroform or dichloroethane; or alcohol solvents such as methanol or ethanol. The reaction may be conducted in the absence of a solvent.

The reaction temperature is normally from ice-cooled temperature to a reflux temperature for the reaction solvent used.

Regarding the molar ratio of the starting compounds, the ratio of the compound of the formula (22)/the compound of the formula (21) (by molar ratio) is within the range of from 0.5 to 5.0, preferably within the range of 1.0 to 2.0.

The compound of the formula (I-g) and the compound of the formula (I-g') may be separated by the known separation method in the organic chemistry such as recrystallization or chromatography.

Compounds of the formula (I) in which $R^7$ and $R^8$ taken together with nitrogen atom to which they are bonded represent imidazolyl group, namely, compound of formula (I-h) may be produced, as shown in Reaction Scheme 14, by reacting the compound of the formula (I-b) with a compound of formula (23) in an inert solvent and in the presence of sodium hydroxide.

Reaction Scheme 14

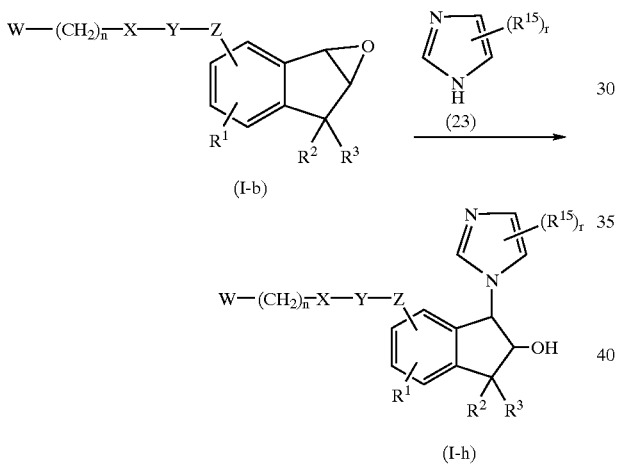

(I-h)

(wherein $R^1$, $R^2$, $R^3$, $R^{15}$, X, Y, Z, W and n have the same meanings as defined above, and r is 0 or an integer of 1 to 3; when r is 2 and 3, $R^{15}$ may be the same or different.)

Solvents usable for this reaction include, for example, sulfoxide solvents such as dimethylsulfoxide; amide solvents such as dimethylformamide or dimethylacetamide; ethereal solvents such as ethyl ether, dimethoxyethane or tetrahydrofuran; halogenated solvents such as dichloromethane, chloroform or dichloroethane; and aromatic solvents such as benzene or toluene. Of these solvents, the aromatic solvents are preferable.

The reaction temperature is normally from ice-cooled temperature to a reflux temperature for the reaction solvent used.

Regarding the molar ratio of the starting compounds, the ratio of the compound of the formula (23)/the compound of the formula (I-b) (by molar ratio) is within the range of from 0.5 to 5.0, preferably within the range of 1.0 to 2.0.

Coexistence with a phase transfer catalyst such as 18-crown-6 in the reaction system may bring good results.

Compound of formula (I-i) and compound of formula (I-i') which are compounds of the formula (I) in which $R^7$ and $R^8$ taken together with nitrogen atoms to which they are bonded represents 1,2,4-triazolyl group may be produced, as shown in Reaction Scheme 15, by reacting the compound of the formula (I-b) with a compound of formula (24) in an inert solvent and in the presence of sodium hydride.

Reaction Scheme 15

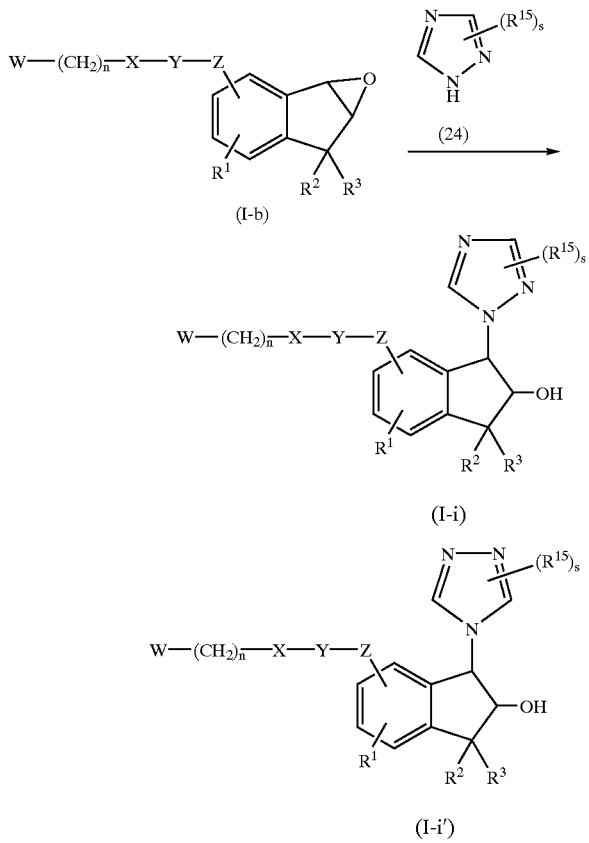

(wherein $R^1$, $R^2$, $R^3$, $R^{15}$, X, Y, Z, W and n have the same meanings as defined above, and s is 0 or an integer of 1 to 2; when s is 2, $R^{15}$ may be the same or different.)

Solvents usable for this reaction include, for example, sulfoxide solvents such as dimethylsulfoxide; amide solvents such as dimethylformamide or dimethylacetamide; ethereal solvents such as ethyl ether, dimethoxyethane or tetrahydrofuran; halogenated solvents such as dichloromethane, chloroform or dichloroethane; and aromatic solvents such as benzene or toluene. Of these solvents, the aromatic solvents are preferable.

The reaction temperature is normally from ice-cooled temperature to a reflux temperature for the reaction solvent used.

Regarding the molar ratio of the starting compounds, the ratio of the compound of the formula (24)/the compound of the formula (I-b) (by molar ratio) is within the range of from 0.5 to 5.0, preferably within the range of 1.0 to 2.0.

Coexistence with a phase transfer catalyst such as 18-crown-6 in the reaction system may bring good results.

Compound of formula (I-j) and compound of formula (I-j') which are compounds of the formula (I) in which $R^7$ and $R^8$ taken together with nitrogen atoms to which they are bonded represent 1,2,3-triazolyl group may be produced, as shown in Reaction Scheme 16, by reacting the compound of the formula (I-b) with a compound of formula (25) in an inert solvent and in the presence of sodium hydride.

Reaction Scheme 16

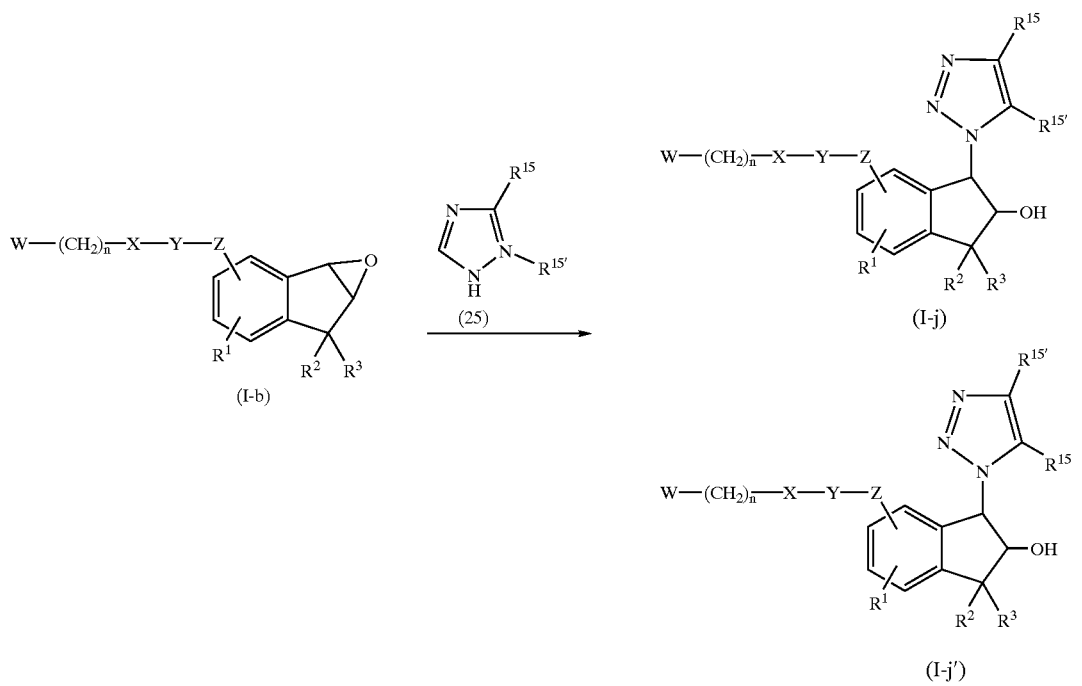

(wherein $R^1$, $R^2$, $R^3$, $R^{15}$, $R^{15'}$, X, Y, Z, W and n have the same meanings as defined above.)

Solvents usable for this reaction include, for example, sulfoxide solvents such as dimethylsulfoxide; amide solvents such as dimethylformamide or dimethylacetamide; ethereal solvents such as ethyl ether, dimethoxyethane or tetrahydrofuran; halogenated solvents such as dichloromethane, chloroform or dichloroethane; and aromatic solvents such as benzene or toluene. Of these solvents, the aromatic solvents are preferable.

The reaction temperature is normally from ice-cooled temperature to a reflux temperature for the reaction solvent used.

Regarding the molar ratio of the starting compounds, the ratio of the compound of the formula (25)/the compound of the formula (I-b) (by molar ratio) is within the range of from 0.5 to 5.0, preferably within the range of 1.0 to 2.0.

Coexistence with a phase transfer catalyst such as 18-crown-6 in the reaction system may bring good results.

As shown in Reaction Scheme 17, the compound of the formula (I-j) and the compound of the formula (I-j') may also be produced by two steps from the compound of the formula (I-b).

Reaction Scheme 17

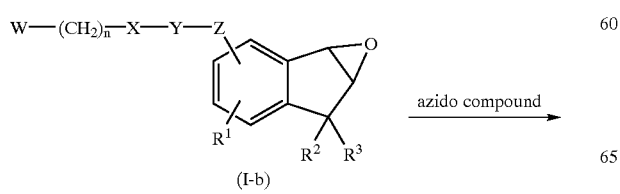

-continued

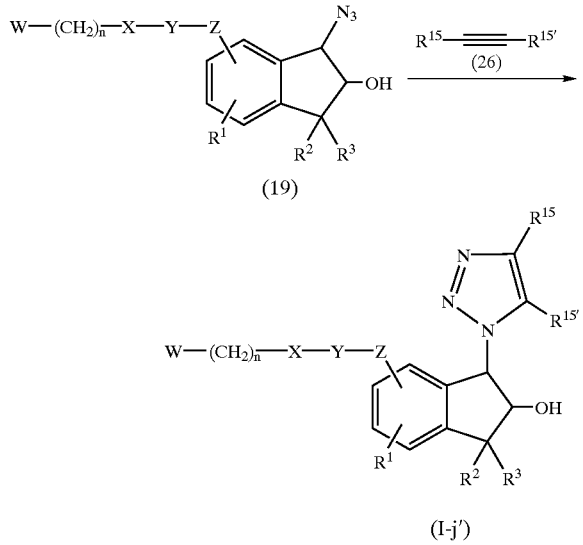

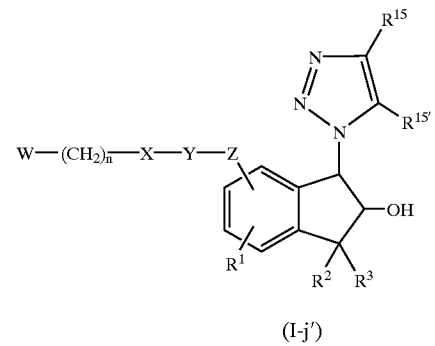

(wherein $R^1$, $R^2$, $R^3$, $R^{15}$, R15', X, Y, Z, W and n have the same meanings as defined above.)

The reaction of the compound of the formula (I-b) with the azido compound may be conducted under conditions similar to those shown in the Reaction Scheme 11.

The compound of the formula (I-j) and the compound of the (I-j') may be produced by reacting the compound of the formula (19) with a compound of formula (26) in an inert solvent.

Solvents usable for this reaction include, for example, sulfoxide solvents such as dimethylsulfoxide; amide solvents such as dimethylformamide or dimethylacetamide; ethereal solvents such as ethyl ether, dimethoxyethane or tetrahydrofuran; halogenated solvents such as dichloromethane, chloroform or dichloroethane; and aromatic solvents such as benzene or toluene. Of these solvents, the aromatic solvents are preferable.

The reaction temperature is normally from 5° C. to 140° C., preferably from 80° C. to 120° C.

Regarding the molar ratio of the starting compounds, the ratio of the compound of the formula (26)/the compound of the formula (19) (by molar ratio) is within the range of from 0.5 to 5.0, preferably from 1.0 to 2.0.

It is preferable to conduct this reaction in a pressure glass tube and an autoclave.

Compounds of the formula (I) in which $R^4$ represents $C_{1-6}$ alkylcarbonyloxy group, namely, compounds of the formula (I-k) may be produced, as shown in Reaction Scheme 18, by reacting the acid chloride of the formula (I-c) with a compound of formula (27) in an inert solvent and in the presence of the base, or by reacting the compound of the formula (I-c) with a carboxylic acid of formula (28) by using a condensation agent.

Reaction Scheme 18

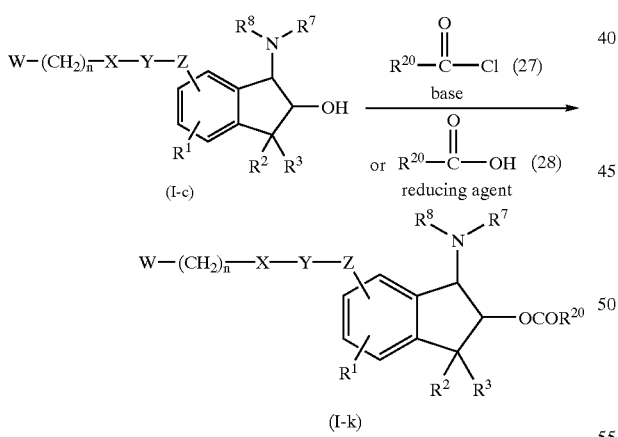

(wherein $R^1$, $R^2$, $R^3$, $R^7$, $R^8$, X, Y, Z, W and n have the same meanings as defined above.)

The reaction of the compound of the formula (I-c) with a compound of formula (27) and the reaction of the compound of the formula (I-c) with an compound of formula (28) may be conducted under conditions similar to those described in the Reaction Scheme 1.

The compound of the formula (1) which is an intermediate compound of the compounds of the formula (I) may be produced by the method as shown in Reaction Scheme 19.

Reaction Scheme 19

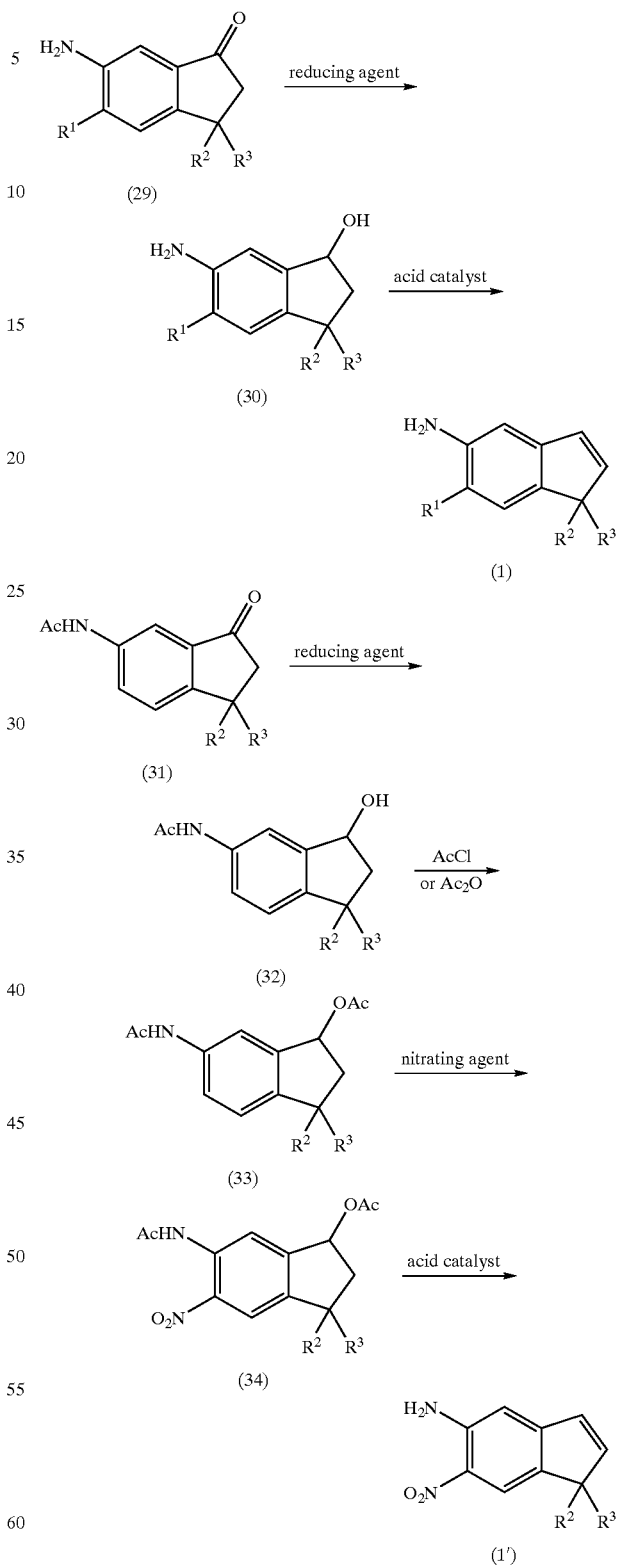

(wherein $R^1$, $R^2$ and $R^3$ have the same meanings as defined above.)

Namely, the compound of the formula (1) may be produced by dehydration-reacting a compound of formula (30)

in the presence of an acid. The acid to be used includes, for example, sulfuric acid, phosphoric acid, potassium hydrogensulfate, oxalic acid, p-toluenesulfonic acid, p-toluenesulfonic acid pyridinium and boron trifluoride ether complex.

Of these acids, sulfuric acid is preferable.

The compound of the formula (30) may be obtained by reducing a compound of formula (29) (the compound of the formula (29) may be synthesized by known methods or according to the methods described by Smith, J. G. et al., *Org. Prep. Proc. Int.*, 123–131, 10, 1978, Buckle, D. R. et al., *J. Med. Chem.*, 919–926, 34, 1991, Stock, L. M. et al., *J. Am. Chem. Soc.*, 4247, 94, 1972 and Japanese Patent Application Laid-open No. Hei 2-141) by using a reducing agent.

The reducing agent to be used include, for example, aliminum reagents such as diisobutyl aluminum hydride, aluminum lithium hydride, lithium trimethoxy aluminum hydride, lithium triethoxy aluminum hydride and lithium tri-t-butoxy aluminum hydride; alkylsilyl reagent such as trimethylsilane and triethylsilane; and boron reagent such as lithium boron hydride, sodium boron hydride, lithum tri-s-butyl boron hydride, potassium tri-s-butyl boron hydride and borane.

Of these reducing agents, sodium boron hydride is preferable.

Compound of formula (1') in which $R^1$ represents nitro group may be synthesized by the following method.

Namely, the compound of the formula (1') may be obtained by dehydration-reacting a compound of formula (34) in the presence of an acid.

The acid to be used includes, for example, sulfuric acid, phosphoric acid, potassium hydrogensulfate, oxalic acid, p-toluenesulfonic acid, p-toluenesulfonic acid pyridinium and boron trifluoride ether complex.

Of these acids, sulfuric acid is preferable.

A compound of formula (34) may be obtained by nitrating a compound of formula (33) by using nitrating agent.

The nitrating agents to be used includes, for example, nitric acid, mixed acid (a mixture of nitric acid and sulfuric acid), sodium nitrate/sulfuric acid, potassium nitrate/sulfuric acid, acetyl nitrate, nitronium trifluoromethane sulfonate, nitronium tetrafluoroborate.

Of these nitrating agents, mixed acid and acetyl nitrate are peferable.

The compound of the formula (33) may be obtained by acetylating the compound of the formula (32) by using acetylating agent such as acetyl chloride and acetic anhydride.

The compound of the formula (32) may be obtained by reducing the compound of the formula (31) (the compound of the formula (31) is already known compound or may be synthesized according to known methods described by Smith, J. G. et al., *Org. Prep. Proc. Int.*, 123–131, 10, 1978, Buckle, D. R. et al., *J. Med. Chem.*, 919–926, 34, 1991, Stock, L. M. et al., *J. Am. Chem. Soc.*, 4247, 94, 1972 and Japanese Patent Application Laid-open No. Hei 2-141) by using a reducing agent.

The reducing agent to be used include, for example, aliminum reagents such as diisobutyl aluminum hydride, aluminum lithium hydride, lithium trimethoxy aluminum hydride, lithium triethoxy aluminum hydride and lithium tri-t-butoxy aluminum hydride; alkylsilyl reagent such as tirmethylsilane and triethylsilane; and boron reagent such as lithium boron hydride, sodium boron hydride, lithum tri-s-butyl boron hydride, potassium tri-s-butyl boron hydride and borane.

Of these reducing agents, sodium boron hydride is preferable.

Of the compounds of the formula (I) of the present invention, optically active isomers may be produced, for example, by methods of optical resolution of racemic modifications (Japanese Patent Application Laid-open No. Hei 3-141286, U.S. Pat. No. 5,097,037, European Patent No. 409165).

Optically active isomers of the compounds of the formula (15) and of the formula (I-b), may be produced, for example, by methods of asymmetric synthesis (Japanese National Publication No. Hei 5-507645, Japanese Patent Application Laid-open No. Hei 5-301878, Japanese Patent Application Laid-open No. Hei 7-285983, European Patent No. 535377 and U.S. Pat. No. 5,420,314).

As mentioned above, the present inventors have found that the compounds of the formula (I) have a strong activity of reducing the heart rate.

The compounds of the present invention have no activity of retarding cardiac functions but rather have an activity of reducing the heart rate. Because of their activities, it is considered that the compounds according to the present invention may reduce the amount of oxygen to be consumed by cardiac muscles to therefore reduce the motility load of cardiac muscles and exert the anti-stenocardiac activity. In addition, it is also considered that they have an activity of prolonging the effective refractory period to thereby exert an anti-arrhythmic activity.

Therefore, it is expected that the compounds of the present invention are useful for curing cardiovascular disorders in consideration of the oxygen consumption, the energy consumption or the metabolism caused by the cardiac motility and also for curing other cardiac disorders essentially in consideration of the activity of the compounds of reducing the heart rate.

For example, the compounds of the present invention are useful as medicines for cardiac insufficiency of mammals including human beings and also as medicines for curing cardiovascular disorders causing cardiac insufficiency of them such as, for example, medicines for curing ischemic cardiopathy, medicines for curing cardiac fluid retention, medicines for curing pulmonary hypertension, medicines for curing valvulitis, medicines for curing congenital cardiac disorders, medicines for curing cardiomuscular disorders, medicines for curing pulmonary edema, medicines for curing angina of effort, medicines for curing myocardial infarction, medicines for curing arrhythmia, and medicines for curing atrial fibrillation.

The present invention provides pharmaceutical compositions or veterinary compositions containing an effective amount of the compounds of the formula (I) for curing these diseases.

The manner of administration of the compounds of the present invention may be parenteral administration by injections (subcutaneous, intraveneous, intramuscular or intraperitoneal injection), ointments, supositories or aerosols, or an oral administration in the form of tablets, capsules, granules, pills, syrups, liquids, emulsions or suspensions.

The above-mentioned pharmaceutical or veterinary compositions of the present invention contain the above-mentioned compounds of the present invention in an amount of from about 0.01 to 99.5%, preferably from about 0.1 to 30%, based on the total weight of the composition.

To the compounds of the present invention or to the compositions containing the compounds of the present invention, other pharmaceutically or veterinarily active compounds may be incorporated.

Further, these compositions may contain a plurality of the compounds of the present invention.

The clinical dose of the compounds of the present invention varies depending upon the age, the body weight, the sensitivity or the sympton, etc. of the patient. In general, however, the effective daily dose is usually from about 0.003 to 1.5 g, preferably from about 0.01 to 0.6 g for an adult. If necessary, however, an amount outside the above-mentioned range may be employed.

The compounds of the invention may be prepared into various suitable formulations depending upon the manner of administration, in accordance with conventional methods commonly employed for the preparations of pharmaceutical formulations.

Namely, tablets, capsules, granules or pills for oral administration may be prepared by using excipients such as white sugar, lactose, glucose, starch or mannitol; binders such as hydroxypropyl cellulose, syrups, arabic gum, gelatin, sorbitol, tragacanth gum, methyl cellulose or polyvinylpyrrolidone; disintegrants such as starch, carboxymethyl cellulose or its calcium salt, crystal cellulose powder or polyethylene glycol; lubricants such as talc, magnesium or calcium stearate, silica; and smoothers such as sodium laurate, glycerol, etc.

The injections, solutions (liquids), emulsions, suspensions, syrups or aerosol may be prepared using a solvent for the active ingredient such as water, ethyl alcohol, isopropyl alcohol, propylene glycol, 1,3-butylene glycol or polyethylene glycol; surfactants such as sorbitan fatty acid esters, polyoxyethylene sorbitan fatty acid esters, polyoxyethylene fatty acid esters, polyoxyethylene ether of hydrogenated castor oil or lecithin; suspending agents such as sodium salt of carboxymethyl, cellulose derivatives such as methyl cellulose or natural rubbers such as tragacanth or arabic gum; or preservatives such as para-hydroxybenzoic acid, benzalkonium chloride or salts of sorbic acid.

Ointments which are an endermic preparation may be prepared by using, e.g., white vaseline, liquid paraffin, higher alcohols, Macrogol ointment, hydrophilic ointment base or hydrogel base, etc.

The suppositories may be prepared by using, e.g., cacao butter, polyethylene glycol, lanolin, fatty acid triglycerides, coconut oil, polysorbate, etc.

BEST MODE FOR CARRYING OUT THE INVENTION

Now, the present invention is explained referring to examples, but it is not to be limited to these examples.

REFERENCE EXAMPLE

Reference Example 1

6-amino-3,3-dimethyl-1-indanol

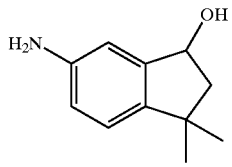

A solution of 6-amino-3,3-dimethyl-1-indanone (said compound is already known and can be synthesized according to a method described by Smith, J., G. and Massicotte, M., P., *Org. Prep. Proc. Int.*, 123–131, 10, 1978) (6.56 g, 37 mmol) in methanol (330 mL) was added with sodium boron hydride (2.1 g, 56 mmol) at 19° C. and stirred at 20° C. for 30 minutes.

After the completion of the reaction, the solvent was distilled off and the residue was added with water and extracted with ethyl acetate.

The organic layer was washed with saturated brine and dried over anhydrous sodium sulfate and then, the solvent was distilled off from the resulting product. The obtained residue was recrystallized from a solution of ethyl acetate-:hexane (=1:5) to obtain 6.17 g of the intended product (yield of 94%) as white crystals.

$^1$H NMR (400 MHz, CDCl$_3$) δ: 1.17 (s, 3H), 1.34 (s, 3H), 1.78 (dd, A part of AB, J=12.9 and 6.1 Hz, 1H), 2.35 (dd, B part of AB, J=12.9 and 7.0 Hz, 1H), 3.50 (br. s, 3H), 5.16 (t, J=7.0 Hz, 1H), 6.62–6.70 (m, 2H), 6.97 (d, J=8.1 Hz, 1H).

MS (EI) m/z 177 [M]$^+$(bp), 144, 120;

mp. 117.8–117.9° C.

Reference Example 2

6-acetamide-3,3-dimethyl-1-indene

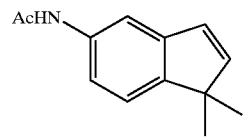

A solution of concentrated sulfuric acid:water (=1:3) (60 mL) was added to 6-amino-3,3-dimethyl-1-indanol (6 g, 34 mmol) and the mixture was stirred at 110° C. for 30 minutes.

After the completion of the reaction, the reaction liquid was neutralized at ice-cooled temperature by using an aqueous solution of 4N-NaOH. After the resulting solution was extracted with ethyl acetate and chloroform, the organic solvent was washed with a saturated aqueous sodium hydrogencarbonate solution and dried over anhydrous sodium sulfate.

The solvent was distilled off from the resulting product to obtain a crude product (7.28 g) of 6-amino-3,3-dimethyl-1-indene.

Subsequently, acetic anhydride (5.2 g, 51 mmol) was added to a solution of the obtained crude product in toluene (27 mL) and stirred at room temperature for 10 minutes. After the completion of the reaction, the reaction liquid was added with a saturated aqueous sodium hydrogencarbonate solution (100 mL) and extracted with toluene. Thereafter, the organic layer was washed with a saturated aqueous sodium chloride solution and dried over anhydrous sodium sulfate.

After the solvent was distilled off from the resulting product, the obtained residue was recrystallized from a solution of ethyl acetate:hexane (=1:11) to obtain 5.66 g of the intended product (yield: 82.7% (two steps)) as white crystals.

$^1$H NMR (400 MHz, CDCl$_3$) δ: 1.29 (s, 6H), 2.17 (s, 3H), 6.38 (d, J=5.3 Hz, 1H), 6.57 (d, J=5.3 Hz, 1H), 7.09–7.18 (m, 3H), 7.50 (d, J=1.4 Hz, 1H).

MS (EI) m/z 201 [M]$^+$, 159, 144 (bp);

mp. 130.7–130.9° C.

Reference Example 3

6-amino-3,3-dimethyl-1-indene

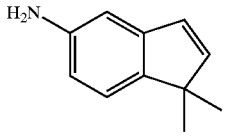

To a solution of 6-acetamide-3,3-dimethyl-1-indene (1.0 g, 4.97 mmol) in ethanol (10 mL) was added a concentrated hydrochloric acid (1 mL) at room temperature and heated at reflux at 90° C. for 8 hours.

After the completion of the reaction, the reaction liquid was neutralized by an aqueous solution of 1N-sodium hydroxide and extracted with ethyl acetate and then, dried over anhydrous sodium sulfate.

After the solvent was distilled off from the resulting product, the obtained residue was purified through a medium-pressure silica-gel column chromatography (hexane:ethyl acetate=3:1) to obtain 653 mg of an intended product (yield: 82%) as colorless oil.

MS (EI) m/z 159 [M]$^+$, 144 (bp).

Reference Example 4

6-acetamide-3,3-dimethyl-1-indanone

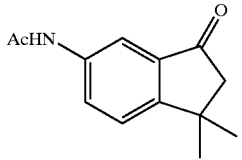

To a solution of 6-amino-3,3-dimethyl-1-indanone (4.2 g, 24 mmol) in toluene (25 mL) was added acetic anhydride (2.7 g, 26.4 mmol) at room temperature and stirred for one hour.

After the completion of the reaction, the reaction liquid was added with water (100 mL) and extracted with toluene (200 mL, 100 mL). The organic layer was washed with an aqueous solution of 1N hydrochloric acid and a saturated aqueous sodium chloride solution and dried over anhydrous sodium sulfate.

The solvent was distilled off from the resulting product to obtain 3.1 g of the intended product (yield: 59.4%) as a white amorphous product.

$^1$H NMR (60 MHz, CDCl$_3$) δ: 1.40 (s, 6H), 2.20 (s, 3H), 2.57 (s, 2H), 7.05–8.00 (m, 3H), 8.87 (brs, 1H).

Reference Example 5

6-acetamide-3,3-dimethyl-1-indanol

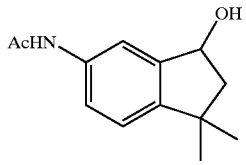

To a solution of the crude 6-acetamide-3,3-dimethyl-1-indanone (1.5 g, 6.9 mmol) obtained in the above-mentioned reaction in methanol solution (75 mL) was added sodium boron hydride (780 mg, 20.7 mmol) at room temperature and stirred for 10 minutes.

After the completion of the reaction, the solvent was distilled off from the reaction liquid by using a rotary evaporator. The residue was added with water (100 mL) and extracted with ethyl acetate (200 mL, 100 mL). The organic layer was washed with a saturated aqueous sodium chloride solution and dried over anhydrous sodium sulfate.

The solvent was distilled off from the resulting product to obtain 1.5 g of the intended product (yield: 99%) as a white amorphous product.

$^1$H NMR (400 MHz, CDCl$_3$) δ: 1.17 (s, 3H), 1.35 (s, 3H), 1.81 (dd, A part of AB, J=13.0 and 6.2 Hz, 1H), 2.13 (s, 3H), 2.34 (dd, B part of AB, J=13.0 and 7.0 Hz, 1H), 2.54 (brs, 1H), 5.18 (m, 1H), 7.10 (d, J=8 Hz, 1H), 7.36–7.38 (m, 1H), 7.49 (s, 1H), 7.68 (brs, 1H);

MS (EI) m/z; 219 [M]$^+$, 205 (bp), 163.

Reference Example 6

6-acetamide-1-acetoxy-3,3-dimethylindane

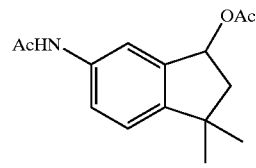

To a solution of 6-acetamide-3,3-dimethyl-1-indanol (1.32 g, 6.02 mmol) in tetrahydrofuran (26 mL) were added N,N-dimethylaminopyridine (about 100 mg), acetic anhydride (1.14 mL, 12.04 mmol) and triethylamine (1.68 mL, 12.04 mmol), and stirred at room temperature for one hour.

After the completion of the reaction, the reaction liquid was added with an aqueous solution of saturated sodium hydrogencarbonate and extracted with ethyl acetate. The organic layer was washed with an aqueous solution of saturated sodium chlorine and dried over anhydrous sodium sulfate.

The solvent was distilled off from the resulting product to obtain 1.59 g of the intended product (yield: 86%) as a white amorphous product.

$^1$H NMR (400 MHz, CDCl$_3$) δ: 1.25 (s, 3H), 1.35 (s, 3H), 1.96 (dd, A part of AB, J=13.7 and 4.2 Hz, 1H), 2.06 (s, 3H), 2.16 (s, 3H), 2.37 (dd, B part of AB, J=13.7 and 7.1 Hz, 1H), 6.12 (dd, J=7.1 and 4.2 Hz, 1H), 7.14 (d, J=8.2 Hz, 1H), 7.43 (d, J=2.0 Hz, 1H), 7.53 (dd, J=8.2 and 2.0 Hz, 1H), 7.61 (brs, 1H);.

MS (EI) m/z; 261 [M]$^+$, 219 (bp), 202, 186, 144.

Reference Example 7

6-acetamide-1-acetone-3,3-dimethyl-5-nitro-indane

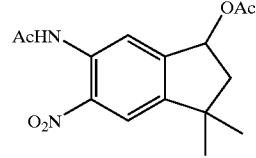

To a solution of 6-acetamide-1-acetone-3,3-dimethylindane (1.55 g, 5.93 mmol) in acetic acid (15.5 mL) was dropwise added fuming nitric acid (3.1 mL), and stirred at 22° C. for 1 hour.

A concentrated sulfuric acid (15 mg) was subsequently added to the mixture and stirred for 30 minutes and then, acetic anhydride (7.8 mL) was added thereto and stirred for 1 hour.

After the completion of the reaction, the reaction liquid was added with a saturated aqueous sodium hydrogencarbonate solution, extracted with an ethyl acetate, washed with a saturated aqueous sodium chloride solution and dried over anhydrous sodium sulfate.

After the solvent was distilled off from the resulting product, the obtained residue was purified through a medium-pressure silica-gel column chromatography (hexane:ethyl acetate=3:1) to obtain 780 mg of the intended product (yield: 42.9%) as yellow oil.

$^1$H NMR (400 MHz, CDCl$_3$) δ: 1.29 (s, 3H), 1.40 (s, 3H), 1.97 (dd, A part of AB, J=13.5 and 7.3 Hz, 1H), 2.12 (s, 3H), 2.28 (s, 3H), 2.50 (dd, B part of AB, J=13.5 and 5.7 Hz, 1H), 6.17 (t, J=6.4 Hz, 1H), 8.00 (s, 1H), 8.65 (s, 1H), 10.25 (brs, 1H);

MS (EI) m/z; 306 [M]$^+$, 261 (bp), 204.

Reference Example 8

6-amino-3,3-dimethyl-5-nitro-1-indene

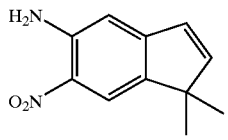

To 6-acetamide-1-acetoxy-3,3-dimethyl-5-nitro-indane (750 mg, 2.45 mmol) was added an aqueous solution of 33% sulfuric acid (15 mL) and heated at reflux at 110° C. for 8 hours.

After the completion of the reaction, the mixture was adjusted to pH13 by using an aqueous solution of 1N-sodium hydroxide, extracted with an ethyl acetate, washed with a saturated aqueous sodium chloride solution and dried over anhydrous sodium sulfate.

After the solvent was distilled off, the resulting product was purified through silica-gel column chromatography (hexane:ethyl acetate=5:1) to obtain 419 mg of the intended product (yield: 83.7%) as brown oil.

$^1$H NMR (400 MHz, CDCl$_3$) δ: 1.32 (s, 6H), 6.18 (brs, 2H), 6.39 (dd, J=5.5 and 0.7 Hz, 1H), 6.64 (d, J=5.5 Hz, 1H), 6.66 (s, 1H), 8.01 (s, 1H);

MS (EI) m/z; 204 [M]$^+$, 189, 158, 143 (bp).

SYNTHESIS EXAMPLE

Synthesis Example 1

6-(4'-methoxybenzylcarboxyamide)-3,3-dimethyl-1-indene

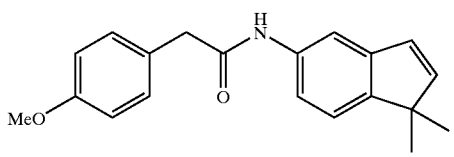

To a solution of 6-amino-3,3-dimethyl-1-indene (653 mg, 4.1 mmol) in chloroform (13 mL) was added 4-methoxyphenylacetic acid chloride (0.94 mL, 6.15 mmol) at room temperature and stirred at room temperature for 1 hour.

Subsequently, diisopropylethylamine (1.07 mL, 6.15 mmol) was added to the mixture and stirred at room temperature for 30 minutes.

After the completion of the reaction, the reaction liquid was added with ethyl acetate, and the organic layer was washed with 1N-hydrochloric acid, an aqueous solution of 1N-sodium hydroxide and a saturated aqueous sodium chloride solution and dried over aqueous sodium sulfate.

After the solvent was distilled off from the resulting product, the obtained residue was purified through a medium-pressure silica-gel column chromatography (hexane:ethyl acetate=3:1) and recrystallized with a solution of ethanol:water (=5:4) to obtain 1.01 g of the intended product (yield: 80%) as white crystals.

$^1$H NMR (400 MHz, CDCl$_3$) δ: 1.26 (s, 6H), 3.68 (s, 3H), 3.82 (s, 3H), 6.35 (d, J=5.5 Hz, 1H), 6.54 (d, J=5.5 Hz, 1H), 6.92 (d, J=8.4 Hz, 2H), 7.1–7.2 (m, 2H), 7.25 (d, J=8.4 Hz, 2H), 7.42 (s, 1H).

MS (EI) m/z 307 [M]$^+$(bp), 278, 149;
mp. 170.6–171.2° C.

Synthesis Example 2

1R*,2S*-6-(4'-methoxybenzylcarboxyamide)-1,2-epoxy-3,3-dimethylindane

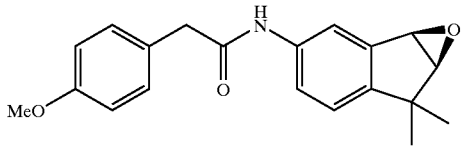

To a solution of 6-(4'-methoxybenzylcarboxylamide)-3,3-dimethyl-1-indene (800 mg, 2.61 mmol) in 1,2-dichloroethane (40 mL) was added 4-(3-phenylpropyl)-pyridineoxide (64 mg, 0.26 mmol) at room temperature and added subsequently (R,S)-salen manganese complex (35):

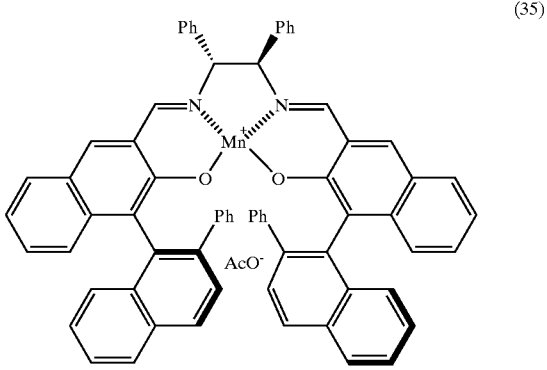

(this compound is a known compound and synthesized according to U.S. Pat. No. 5,420,314) (135 mg, 0.13 mmol) and an aqueous solution of sodium hypochlorite (3.92 mmol, 1.7 mol/kg, 1.5 eq) and stirred at room temperature for 1.5 hours.

After the completion of the reaction, the reaction liquid was added with ethyl acetate and the organic layer was washed with water and a saturated aqueous sodium chloride solution and dried over anhydrous sodium sulfate.

After the solvent was distilled off from the resulting product, the obtained residue was purified through a medium-pressure silica-gel column chromatography (hexane:ethyl acetate=2:1) to obtain 600 mg of the intended product (yield: 71%) as a white amorphous product.

$[α]^{24}_D$ −24.7 (c 0.384, CHCl$_3$).

¹H NMR (400 MHz, CDCl₃) δ: 1.18 (s, 3H), 1.36 (s, 3H), 3.65 (s, 2H), 3.68 (d, J=2.7 Hz, 1H), 3.82 (s, 3H), 4.16 (d, J=2.7 Hz, 1H), 6.92 (d, J=8.6 Hz, 2H), 7.04 (d, J=8.1 Hz, 1H), 7.63 (d, J=1.8 Hz, 1H).

MS (EI) m/z 323 [M]⁺(bp), 293, 175.

Synthesis Example 3

1R*,2S*-6-(4'-methoxybenzylcarboxyamide)-1-cyclopropylamino-3,3-dimethyl-2-indanol

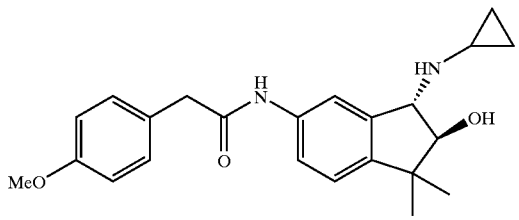

To a solution of 1R*,2S*-6-(4'-methoxybenzylcarboxyamide)-1,2-epoxy-3,3-dimethylindane (250 mg, 0.77 mmol) in 1-propanol (5 ml) was added cyclopropylamine (429 μL, 6.18 mmol) at room temperature and stirred at 80° C. for 9 hours.

After the completion of the reaction, the solvent was distilled off from the resulting product. The obtained residue was purified through a preparative silica-gel thin layer chromatography (chloroform:methanol=10:1) to obtain 252 mg of the intended product (yield: 85.7%) as a white amorphous product.

$[\alpha]^{24}_D$ +1.8 (c 0.944, CHCl₃); ¹H NMR (400 MHz, CDCl₃) δ: 0.41–0.53 (m, 4H), 1.06 (s, 3H), 1.3 (s, 3H), 2.4–2.55 (m, 3H), 3.65 (s, 2H), 3.77 (d, J=8.2 Hz, 1H), 3.81 (s, 3H), 3.92 (d, J=8.2 Hz, 1H), 6.91 (d, J=8.6 Hz, 2H), 7.04 (d, J=8.1 Hz, 1H), 7.16–7.25 (m, 3H), 7.31 (s, 1H), 7.5 (s, 1H)

MS (EI) m/z 380 [M]⁺(bp), 351, 324, 177.

Synthesis Example 4

1S*,2S*-6-(4'-methoxybenzylcarboxyamide)-1-cyclopropylamino-3,3-dimethyl-2-indanol hydrochloride

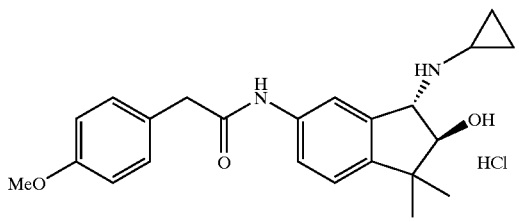

To a solution of 1S*,2S*-6-(4'-methoxybenzylcarboxyamide)-1-cyclopropylamino-3,3-dimethyl-2-indanol (100 mg, 0.263 mmol) in methanol (1 mL) was dropwise added 10% hydrochloric acid-methanol solution (1 mL) at ice-cooled temperature and stirred at 0° C. for 30 minutes.

After the completion of the reaction, the solvent was distilled off from the resulting product to obtain 110 mg of the intended product (yield: 100%) as a white solid.

Synthesis Example 5

6-(4'-methoxybenzylcarboxyamide)-3,3-dimethyl-5-nitro-1-indene

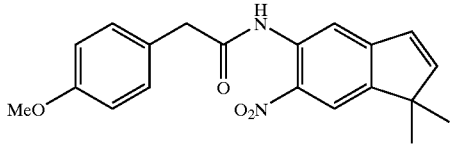

To a solution of 6-amino-3,3-dimethyl-6-nitro-1-indene (400 mg, 1.96 mmol) in chloroform (8 mL) was added diisopropylethylamine (1.0 mL, 5.88 mmol) and 4-methoxyphenylacetic acid chloride (0.9 mL, 5.88 mmol) at 24° C. and stirred at 24° C. for 1 hour.

After the completion of the reaction, the reaction liquid was added with water and extracted with ethyl acetate, and the organic layer was washed with an aqueous solution of 1N-hydrochloric acid, an aqueous solution of 1N-sodium hydroxide and a saturated aqueous sodium chloride solution and dried over anhydrous sodium sulfate.

After the solvent was distilled off from the resulting product, the obtained residue was purified through a silica-gel column chromatography (hexane:ethyl acetate=6:1) to obtain 468 mg of the intended product (yield: 67.8%) as a yellow solid.

¹H NMR (400 MHz, CDCl₃) δ: 1.32 (s, 6H), 3.76 (s, 2H), 3.82 (s, 3H), 6.65 (d, J=5.5 Hz, 1H), 6.69 (d, J=5.5 Hz, 1H), 6.94 (AA'BB' type, J=8.8 and 2.2 Hz, 2H), 7.28 (AA'BB' type, J=8.8 and 2.0 Hz, 2H), 8.07 (s, 1H), 8.67 (s, 1H), 10.53 (s, 1H);

MS (EI) m/z; 352 [M]⁺, 306, 204, 148 (bp), 121.

Synthesis Example 6

(1R*,2S*)-6-(4'-methoxybenzylcarboxyamide)-1,2-epoxy-3,3-dimethyl-5-nitroindane

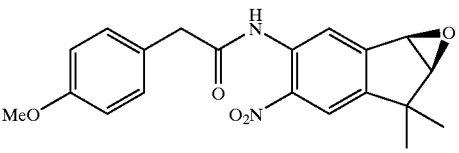

To a solution of 6-(4'-methoxybenzylcarboxyamide)-3,3-dimethyl-5-nitro-1-indene (354 mg, 1.00 mmol) in 1,2-dichloroethane (7.1 mL) was added 4-(3-phenylpropyl)-pyridineoxide (25 mg, 0.10 mmol) at room temperature and added subsequently (R,S)-salen manganese complex (46) (52 mg, 0.05 mmol), an aqueous solution of sodium hypochlorite (882 mg, 1.7 mol/kg, 1.5 mmol) and stirred at room temperature for 1.5 hours.

After the completion of the reaction, the reaction liquid was added with water (50 mL) and ethyl acetate (100 mL) and filtered with sellaite.

Subsequently, the resulting product was extracted with ethyl acetate and the organic layer was washed with a saturated aqueous sodium chloride solution and dried over anhydrous sodium sulfate.

After the solvent was distilled off, the obtained residue was purified through silica-gel column chromatography (hexane:ethyl acetate=5:1) to obtain 281 mg of the intended product (yield: 76.2%) as yellow oil.

¹H NMR (400 MHz, CDCl₃) δ: 1.23 (s, 3H), 1.40 (s, 3H), 3.76 (s, 2H), 3.77 (d, J=2.6 Hz, 1H), 3.83 (s, 3H), 4.25 (d,

J=2.6 Hz, 1H), 6.90–6.99 (m, 2H), 7.25–7.30 (m, 2H), 7.92 (s, 1H), 8.89 (s, 1H), 10.31 (brs, 1H);

MS (EI) m/z; 368 [M]$^+$, 322, 205, 148, 122 (bp), 91.

Synthesis Example 7

(1S*,2S*)-6-(4'-methoxybenzylcarboxyamide)-1-cyclopropylamino-3,3-dimethyl-5-nitro-2-indanol

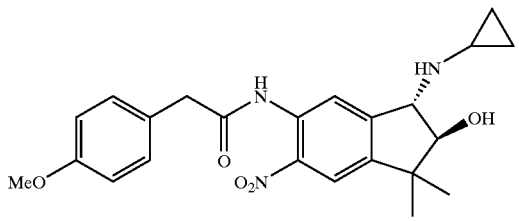

To a solution of (1R*,2S*)-6-(4'-methoxybenzylcarboxyamide)-1,2-epoxy-3,3-dimethyl-5-nitroindane (216 mg, 0.59 mmol) in 1-propanol (4.3 mL) was added cyclopropylamine (325 µL, 4.69 mmol) at room temperature and stirred at 80° C. for 8 hours.

Subsequently, cyclopropylamine (163 µL, 2.35 mmol) was added to the mixture and stirred at 80° C. for 5 hours.

After the completion of the reaction, the solvent was distilled off from the resulting product. The obtained residue was purified through a preparative thin layer chromatography (hexane:ethyl acetate=1:2) to obtain 205 mg of the intended product (yield: 82.2%) as a yellow amorphous product.

$^1$H NMR (400 MHz, CDCl$_3$) δ: 0.45–0.60 (m, 4H), 1.11 (s, 3H), 1.36 (s, 3H), 1.92–2.00 (brs, 2H), 2.50–2.57 (m, 1H), 3.75 (s, 2H), 3.82 (s, 3H), 3.83 (d, J=8.6 Hz, 1H), 4.10 (dd, J=8.6 and 1.3 Hz, 1H), 6.93–7.00 (m, 2H), 7.24–7.28 (m, 2H), 7.92 (s, 1H), 8.76 (s, 1H), 10.32 (s, 1H);

MS (EI) m/z; 425 [M]$^+$, 379, 361, 148, 121 (bp), 91; $[\alpha]^{20}_D$ +37.6 (c 0.68, CHCl$_3$).

Synthesis Example 8

(1S*,2S*)-6-(4'-methoxybenzylcarboxyamide)-1-cyclopropylamino-3,3-dimethyl-5-nitro-2-indanol hydrochloride

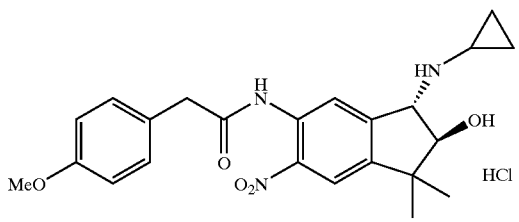

To a solution of (1S*,2S*)-6-(4'-methoxybenzylcarboxyamide)-1-cyclopropylamino-3,3-dimethyl-5-nitro-2-indanol (106 mg, 0.25 mmol) in methanol (1 mL) was dropwise added 10% hydrochloric acid methanol solution (1 mL) at ice-cooled temperature and stirred at 0° C. for 30 minutes.

After the completion of the reaction, the solvent was distilled off from the resulting product to obtain 115 mg of the intended product (yield: 100%) as a yellow solid.

FORMULATION EXAMPLES

Formulation Example 1

Tablets

| | |
|---|---|
| Compound of the Synthesis Example 4 | 10 g |
| Lactose | 260 g |
| Crystal cellulose powder | 600 g |
| Corn Starch | 350 g |
| Hydroxypropyl cellulose | 100 g |
| CMC-Ca | 150 g |
| Magnesium stearate | 30 g |
| Total | 1500 g |

The above-mentioned components were mixed by a usual method and then tabletted to produce 10000 sugar-coated tablets, each containing one mg of the active ingredient.

Formulation Example 2

Capsules

| | |
|---|---|
| Compound of the Synthesis Example 4 | 10 g |
| Lactose | 440 g |
| Crystal cellulose powder | 1000 g |
| Magnesium stearate | 50 g |
| Total | 1500 g |

The above-mentioned components were mixed by a usual method and then packed in gelatin capsules to obtain 10000 capsules, each containing one mg of the active ingredient.

Formulation Example 3

Soft Capsules

| | |
|---|---|
| Compound of the Synthesis Example 4 | 10 g |
| PEG400 | 479 g |
| Saturated fatty acid triglyceride | 1500 g |
| Peppermint oil | 1 g |
| Polysorbate 80 | 10 g |
| Total | 2000 g |

The above-mentioned components were mixed and packed in No. 3 soft gelatin capsules by a usual method to obtain 10000 soft capsules, each containing one mg of the active ingredient.

Formulation Example 4

Ointment

| | |
|---|---|
| Compound of the Synthesis Example 4 | 1.0 g |
| Liquid paraffin | 10.0 g |
| Cetanol | 20.0 g |
| White vaseline | 68.4 g |

| | | | |
|---|---|---|---|
| Ethylparaben | | | 0.1 g |
| L-menthol | | | 0.5 g |
| Total | | | 100.0 g |

The above-mentioned components were mixed by a usual method to obtain 1% ointoment.

Formulation Example 5

Suppositories

| | |
|---|---|
| Compound of the Synthesis Example 4 | 1 g |
| Witepsol H15* | 478 g |
| Witepsol W35* | 520 g |
| Polysorbate 80 | 1 g |
| Total | 1000 g |

(*trade name for triglyceride compound)

The above-mentioned components were melt-mixed by a usual method and poured into suppository containers, followed by cooling for solidification to obtain 1000 suppositories of 1 g, each containing one mg of the active ingredient.

Formulation Example 6

Injection

| | |
|---|---|
| Compound of the Synthesis Example 4 | 1 mg |
| Distilled water for injection | 5 mL |

The formulation is prepared by dissolving the compound in distilled water whenever it is required.

PHARMACOLOGICAL TEST EXAMPLES

Effect on the Heart Rate

Test Method

The heart was taken out from a male Hartley guinea pig, and the right atrium cordis was separated from it in a Krebs Henseleit liquid aerated with 95%—$O_2$/5%—$CO_2$. The specimen was overhung under tension of 1 g in an organ bath filled with a nutrient liquid, which was kept at 31° C.

After the specimens were equilibrated while exchanging the nutrient liquid, isoproterenol was accumulatively applied with the specimens to obtain the maximum reaction of the specimens. After, the isoproterenol applied was washed out, the specimens were again equilibrated for 60 minutes while exchanging the nutrient liquid. Afterwards, the test compounds mentioned below were applied to the specimens, while their reactions were observed.

The relative variation (%) in the heart rate of the specimens due to the addition of the test compounds (10 μM, 30 μM, 100 μM and 300 μM thereto) was obtained, on the basis of the maximum reaction (100%) previously obtained when isoproterenol had been applied.

Results

Compounds of the present invention showed an activity of reducing heart rate which is dependent on the concentration of the compound applied.

| Synthetic Example No. | Activity of Compounds Variation (%) in heart rate | | | |
|---|---|---|---|---|
| | 10 μM | 30 μM | 100 μM | 300 μM |
| 1 | −15 | −100 | −100 | −100 |
| 2 | −3.8 | −5.3 | −10.7 | −81 |
| 4 | −11.6 | −23.9 | −43.5 | −73.9 |

INDUSTRIAL APPLICABILITY

The Compounds of the present invention show strong activity of reducing the heart rate and are useful for improving cardiac functions and therefore, the present invention can provide useful medicines for treating cardiac insufficiency

What is claimed is:

1. Indane compounds of formula (I):

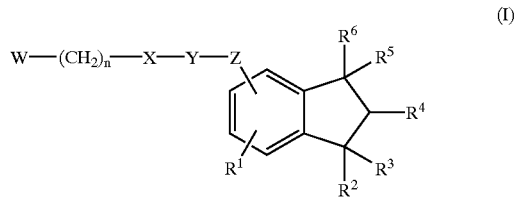

wherein $R^1$ represents hydrogen atom, halogen atom, $C_{1-6}$ alkyl group (said alkyl group is unsubstituted or substituted by halogen atom, carboxyl group, $C_{1-6}$ alkoxy group, $C_{2-6}$ alkoxycarbonyl group, hydroxyl group, formyl group, cyano group or nitro group), $C_{1-6}$ alkoxy group {said alkoxy group is unsubstituted or substituted by halogen atom, carboxyl group, $C_{2-6}$ alkoxycarbonyl group, hydroxyl group, phenyl group (said phenyl group is unsubstituted or substituted by halogen atom, hydroxyl group, $C_{1-4}$ alkyl group or $C_{1-4}$ alkoxy group), formyl group, cyano group or nitro group}, $C_{3-6}$ cycloalkyl group {said cycloalkyl group is unsubstituted or substituted by halogen atom, carboxyl group, $C_{2-6}$ alkoxycarbonyl group, hydroxyl group, $C_{1-6}$ alkoxy group, phenyl group (said phenyl group is unsubstituted or substituted by halogen atom, hydroxyl group, $C_{1-4}$ alkyl group or $C_{1-4}$ alkoxy group), formyl group, cyano group or nitro group}, nitro group, cyano group, formyl group, carboxyl group, hydroxyl group, formamide group, cyanamide group, amino group, $C_{1-6}$ alkylamino group, di $C_{1-6}$ alkylamino group (said alkylamino group and di $C_{1-6}$ alkylamino group is unsubstituted or substituted by halogen atom, carboxyl group, $C_{2-6}$ alkoxycarbonyl group, hydroxyl group, formyl group, cyano group or nitro group), $C_{1-6}$ alkylcarbonylamino group, $C_{1-6}$ alkylsulfonylamino group, aminocarbonyl group, $C_{1-6}$ alkylaminocarbonyl group, di $C_{1-6}$ alkylaminocarbonyl group, $C_{1-6}$ alkylcarbonyl group, $C_{1-6}$ alkoxycarbonyl group, $C_{1-6}$ alkylcarbonyloxy group, $C_{1-6}$ alkylurea group, $C_{1-6}$ alkylthiourea group, aryl $C_{1-6}$ alkylamino group, di(aryl $C_{1-6}$ alkyl)amino group, arylcarbonylamino group, aryl $C_{1-6}$ alkylcarbonylamino group, arylsulfonylamino group, aryl $C_{1-6}$ alkylsulfonylamino group, aryl $C_{1-6}$ alkylaminocarbonyl group, di(aryl $C_{1-6}$ alkyl)aminocarbonyl group, arylcarbonyl group, aryl $C_{1-6}$ alkylcarbonyl group, aryloxycarbonyl group, aryl $C_{1-6}$ alkyloxycarbonyl group, arylcarbonyloxy group, aryl $C_{1-6}$ alkylcarbonyloxy group, arylurea group, aryl $C_{1-6}$ alkylurea group, arylthiourea group or aryl $C_{1-6}$ alkylthiourea group {all of said aryl $C_{1-6}$ alkylamino group, di(aryl $C_{1-6}$ alkyl)amino group, arylcarbonylamino group, aryl $C_{1-6}$ alkylcarbonylamino group, arylsulfonylamino group, aryl $C_{1-6}$ alkylsulfonylamino group, aryl $C_{1-6}$ alkylaminocarbonyl group, di(aryl $C_{1-6}$ alkyl) aminocarbonyl group, arylcarbonyl group, aryl $C_{1-6}$ alkylcarbonyl group, aryloxycarbonyl group, aryl $C_{1-6}$ alkyloxycarbonyl group, arylcarbonyloxy group, aryl $C_{1-6}$ alkylcarbonyloxy group, arylurea group, aryl $C_{1-6}$ alkylurea group, arylthiourea group and aryl $C_{1-6}$ alkylthiourea group are unsubstituted or substituted by halogen atom, carboxyl group, $C_{2-6}$ alkoxycarbonyl group, hydroxyl group, $C_{1-6}$ alkoxy group, phenyl group (said phenyl group is unsubstituted or substituted by halogen atom, hydroxyl group, $C_{1-4}$ alkyl group or $C_{1-4}$ alkoxy group), formyl group, cyano group or nitro group};

$R^2$ and $R^3$ each independently represent $C_{1-6}$ alkyl group (said alkyl group is unsubstituted or substituted by halogen atom, $C_{1-6}$ alkoxy group or hydroxyl group), or $R^2$ and $R^3$ taken together with the carbon atom to which they are bonded form $C_{3-6}$ cycloalkyl group;

$R^4$ represents hydroxyl group or $C_{1-6}$ alkylcarbonyloxy group, or form a bond together with $R^5$, or represents oxygen atom together with $R^5$;

$R^5$ represents hydrogen atom, or forms a bond together with $R^4$, or represents oxygen atom together with $R^4$;

$R^6$ represents hydrogen atom, hydroxyl group, $C_{1-6}$ alkoxy group, $C_{1-6}$ alkylcarbonyloxy group or $NR^7R^8$, wherein $R^7$ and $R^8$ taken together represent 1,4-butylene, 1,5-pentylene (said butylene and pentylene are each unsubstituted or substituted by $C_{1-4}$ alkyl group, phenyl group (said phenyl group is unsubstituted or substituted by halogen atom, hydroxyl group, $C_{1-4}$ alkyl group or $C_{1-4}$ alkoxy group), halogen atom, hydroxyl group, $C_{1-4}$ alkoxy group or $C_{1-6}$ alkylcarbonyloxy group) or $(CH_2)_1X^1(CH_2)_p$ (1 and p each mean 1, 2 or 3 while the sum of them becomes 3, 4 or 5; $X^1$ represents oxygen atom, sulfur atom or $NR^{14}$ ($R^{14}$ is unsubstituted or substituted by hydrogen atom, $C_{1-4}$ alkyl group or phenyl group (said phenyl group is unsubstituted or substituted by halogen atom, hydroxyl group, $C_{1-4}$ alkyl group or $C_{1-4}$ alkoxy group))), n means 0 or an integer of 1 to 4;

X represents C=O;

Y represents $NR^{17}$, wherein $R^{17}$ is hydrogen;

Z is absent when Y represents $NR^{17}$;

W represents

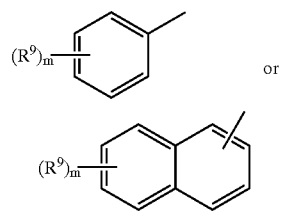

or wherein $R^9$ represents hydrogen atom, halogen atom, $C_{1-6}$ alkyl group (said alkyl group is unsubstituted or substituted by halogen atom or $C_{1-6}$ alkoxy group), $C_{1-6}$ alkoxy group (said alkoxy group is unsubstituted or substituted by halogen atom), phenyl group (said phenyl group is unsubstituted or substituted by halogen atom, hydroxyl group, $C_{1-4}$ alkyl group or $C_{1-4}$ alkoxy group), hydroxyl group, nitro group, cyano group, formyl group, formamide group, amino group, $C_{1-6}$ alkylamino group, di $C_{1-6}$ alkylamino group, $C_{1-6}$ alkylcarbonylamino group, $C_{1-6}$ alkylsulfonylamino group, aminocarbonyl group, $C_{1-6}$ alkylaminocarbonyl group, di $C_{1-6}$ alkylaminocarbonyl group, $C_{1-6}$ alkylcarbonyl group, $C_{1-6}$ alkoxycarbonyl group, aminosulfonyl group, $C_{1-6}$ alkylsulfonyl group, carboxyl group or arylcarbonyl group; and m is an integer of 1 to 3; and $R^9$ may be the same or different when m is 2 or 3; or pharmaceutically acceptable salt thereof.

2. Indane compounds of the formula (I) as claimed in claim 1, wherein both $R^2$ and $R^3$ represent methyl group and the combination of —X—Y—Z— is —C(O)—NH—, —C(O)—NMe—, —CH$_2$—NH—, —SO$_2$—NH— or —NH—C(O)—NH—, or pharmaceutically acceptable salt thereof.

3. Indane compounds or pharmaceutically acceptable salt thereof as claimed in claim 2, wherein W represents

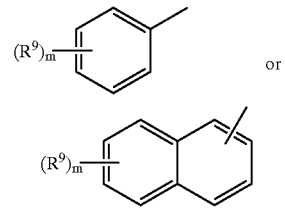

or $R^9$ represents hydrogen atom, halogen atom, $C_{1-6}$ alkyl group, $C_{1-6}$ alkoxy group (said alkoxy group is unsubstituted or substituted by halogen atom), hydroxyl group, nitro group, cyano group, formyl group, amino group, $C_{1-6}$ alkylamino group, di $C_{1-6}$ alkylamino group, $C_{1-6}$ alkylcarbonylamino group, $C_{1-6}$ alkylsulfonylamino group, aminocarbonyl group, $C_{1-6}$ alkylaminocarbonyl group, di $C_{1-6}$ alkylaminocarbonyl group, $C_{1-6}$ alkylcarbonyl group, $C_{1-6}$ alkoxycarbonyl group, aminosulfonyl group, $C_{1-6}$ alkylsulfonyl group or carboxyl group.

4. Indane compounds or pharmaceutically acceptable salt thereof as claimed in claim 3, wherein $R^1$ represents hydrogen atom or nitro group.

5. Indane compounds or pharmaceutically acceptable salt thereof as claimed in claim 4, wherein $R^4$ forms a bond together with $R^5$; or $R^4$ represents oxygen atom together with $R^5$; or $R^4$ represents hydroxyl group, $R^5$ represents hydrogen atom and $R^6$ represents amino group, $C_{1-6}$ alkylamino group, di $C_{1-6}$ alkylamino group {said alkylamino group and di $C_{1-6}$ alkylamino group are unsubstituted or substituted by halogen atom, carboxyl group, $C_{2-6}$ alkoxycarbonyl group, hydroxyl group, formyl group, cyano group or nitro group}, $C_{1-6}$ cycloalkylamino group, aryl $C_{1-6}$ alkylamino group, di(aryl $C_{1-6}$ alkyl)amino group {both said aryl $C_{1-6}$ alkylamino group and di(aryl $C_{1-6}$ alkyl)amino group are unsubstituted or substituted by $R^{19}$ (said $R^{19}$ is unsubstituted or substituted by halogen atom, carboxyl group, $C_{2-6}$ alkoxycarbonyl group, hydroxyl group, $C_{1-6}$ alkoxy group, phenyl group (said phenyl group is unsubstituted or substituted by halogen atom, hydroxyl group, $C_{1-4}$ alkyl group or $C_{1-4}$ alkoxy group), formyl group, cyano group, or nitro group)}, 1-pyrrolidinyl group, 1-imidazolidinyl group, 1-piperidyl group, 1-piperazinyl group or 1-morpholino group.

6. Indane compounds or pharmaceutically acceptable salt thereof as claimed in claim 5, wherein $R^9$ represents hydrogen atom, halogen atom, $C_{1-6}$ alkyl group, $C_{1-6}$ alkoxy group (said alkoxy group is unsubstituted or substituted by halogen atom), hydroxyl group, nitro group, cyano group, formyl group, amino group, $C_{1-6}$ alkylamino group, di $C_{1-6}$ alkylamino group, $C_{1-6}$ alkylcarbonyl group, $C_{1-6}$ alkoxycarbonyl group or carbonyl group.

7. Indane compounds or pharmaceutically acceptable salt thereof as claimed in claim 6, wherein $R^4$ forms a bond together with $R^5$.

8. Indane compounds or pharmaceutically acceptable salt thereof as claimed in claim 6, wherein $R^4$ represents hydroxyl group, $R^5$ represents hydrogen atom and $R^6$ represents amino group, $C_{1-6}$ alkylamino group, di $C_{1-6}$ alkylamino group {said alkylamino group and di $C_{1-6}$ alkylamino group are unsubstituted or substituted by halogen atom, carboxyl group, $C_{2-6}$ alkoxycarbonyl group, hydroxyl group, formyl group, cyano group or nitro group} or $C_{1-6}$ cycloalkylamino group.

9. Indane compounds or pharmaceutically acceptable salt thereof as claimed in claim 7, wherein W represents 4-methoxyphenyl group.

10. Indane compounds or pharmaceutically acceptable salt thereof as claimed in claim 8, wherein $R^6$ represents isopropylamino group or cyclopropylamino group, and W represents 4-methoxyphenyl group.

11. A pharmaceutical composition comprising a therapeutically effective amount of at least one compound as claimed in claim 1 and one or more pharmaceutically acceptable excipients.

12. A method for treating cardiac insufficiency comprising administering to a subject in need thereof a therapeutically effective amount of at least one indane compound as claimed in claim 1 and one or more pharmaceutically acceptable excipients.

* * * * *